(12) United States Patent
Booker et al.

(10) Patent No.: US 7,820,665 B2
(45) Date of Patent: Oct. 26, 2010

(54) IMIDAZOPYRIDAZINE INHIBITORS OF PI3 KINASE FOR CANCER TREATMENT

(75) Inventors: Shon Booker, Thousand Oaks, CA (US); Tae-Seong Kim, Thousand Oaks, CA (US); Hongyu Liao, Thousand Oaks, CA (US); Longbin Liu, Thousand Oaks, CA (US); Mark H. Norman, Thousand Oaks, CA (US); Emily Anne Peterson, Cambridge, MA (US); Markian Stec, Moorpark, CA (US); Nuria A. Tamayo, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 7 days.

(21) Appl. No.: 12/317,166

(22) Filed: Dec. 18, 2008

(65) Prior Publication Data

US 2009/0163489 A1    Jun. 25, 2009

Related U.S. Application Data

(60) Provisional application No. 61/008,430, filed on Dec. 19, 2007.

(51) Int. Cl.
*A61K 31/4188* (2006.01)
*A61K 31/5025* (2006.01)
*C07D 487/04* (2006.01)

(52) U.S. Cl. .................................. 514/248; 544/236
(58) Field of Classification Search .................. None
See application file for complete search history.

(56) References Cited

U.S. PATENT DOCUMENTS

| 3,725,428 A | 4/1973 | Janiak |
| 2003/0153568 A1 | 8/2003 | Cusack |
| 2009/0098086 A1 | 4/2009 | Zask et al. |
| 2009/0181963 A1 | 7/2009 | Dehnhardt et al. |
| 2009/0192176 A1 | 7/2009 | Zask et al. |

FOREIGN PATENT DOCUMENTS

| WO | WO 2004/007491 A1 | 1/2004 |
| WO | WO 2004/010995 A1 | 2/2004 |
| WO | WO 2004/098494 A2 | 11/2004 |
| WO | WO 2005/003127 A1 | 1/2005 |
| WO | WO 2005/070920 A1 | 8/2005 |
| WO | WO 2006/039718 A2 | 4/2006 |
| WO | WO 2006/040318 A2 | 4/2006 |
| WO | WO 2006/044732 A2 | 4/2006 |
| WO | WO2006/046031 A1 | 5/2006 |
| WO | WO 2006/051270 A1 | 5/2006 |
| WO | WO 2006/052913 * | 5/2006 |
| WO | WO 2007/016392 A2 | 2/2007 |
| WO | WO 2007/076092 A2 | 7/2007 |
| WO | WO 2007/095588 * | 8/2007 |
| WO | WO 2007/095588 A1 | 8/2007 |
| WO | WO 2007/129044 A1 | 11/2007 |
| WO | WO 2007/129052 A1 | 11/2007 |
| WO | WO2007/132171 A1 | 11/2007 |
| WO | WO 2007/134828 A1 | 11/2007 |
| WO | WO 2007/135398 A1 | 11/2007 |
| WO | WO 2008/003856 A1 | 1/2008 |
| WO | WO 2008/012326 A1 | 1/2008 |
| WO | WO 2008/016131 A1 | 2/2008 |
| WO | WO 2008/025821 A1 | 3/2008 |
| WO | WO 2008/037477 A1 | 4/2008 |
| WO | WO 2008/052733 A1 | 5/2008 |
| WO | WO2008/070740 A1 | 6/2008 |
| WO | WO2008/073785 A2 | 6/2008 |
| WO | WO2008/101979 A1 | 8/2008 |
| WO | WO2008/115974 A2 | 9/2008 |

(Continued)

OTHER PUBLICATIONS

Dorwald F. A. Side Reactions in Organic Synthesis, 2005, Wiley: VCH, Weinheim, preface and relevant pages attached.*

(Continued)

*Primary Examiner*—Golam M. M. Shameem
*Assistant Examiner*—Alicia L Fierro
(74) *Attorney, Agent, or Firm*—Todd M. Crissey

(57) ABSTRACT

The present invention relates to imidazopyridazine compounds of Formula I, such as representative structure A, or a pharmaceutically acceptable salt thereof, that inhibit phosphoinositide 3-kinase;

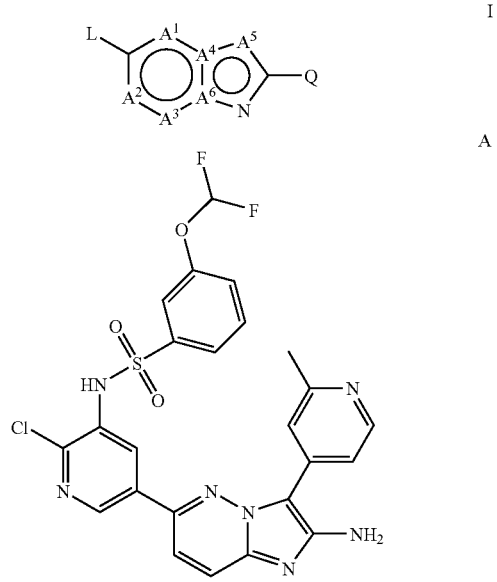

methods of treating diseases or conditions, such as cancer, using the compounds; and pharmaceutical compositions containing the compounds.

9 Claims, No Drawings

FOREIGN PATENT DOCUMENTS

| WO | WO 2008/116129 A2 | 9/2008 |
|---|---|---|
| WO | WO 2008/133192 A1 | 11/2008 |
| WO | WO 2008/138834 A1 | 11/2008 |
| WO | WO 2008/138889 A2 | 11/2008 |
| WO | WO2008/141065 A1 | 11/2008 |
| WO | WO 2008/144463 A1 | 11/2008 |
| WO | WO 2008/144464 A1 | 11/2008 |
| WO | WO 2008/144465 A1 | 11/2008 |
| WO | WO 2008/150827 A1 | 12/2008 |
| WO | WO2008/152387 A1 | 12/2008 |
| WO | WO 2008/152387 A1 | 12/2008 |
| WO | WO2008/152390 A1 | 12/2008 |
| WO | WO2008/152394 A1 | 12/2008 |
| WO | WO 2008/157191 A2 | 12/2008 |
| WO | WO 2009/000832 A2 | 12/2008 |
| WO | WO2009/008748 A1 | 1/2009 |
| WO | WO 2009/010530 A1 | 1/2009 |
| WO | WO 2009/017822 A1 | 2/2009 |
| WO | WO2009/053715 A1 | 4/2009 |
| WO | WO2009/053716 A1 | 4/2009 |
| WO | WO2009/055418 A1 | 4/2009 |
| WO | WO2009/068482 A1 | 6/2009 |
| WO | WO2009/070524 A1 | 6/2009 |
| WO | WO2009/081105 A2 | 7/2009 |
| WO | WO2009/097446 A1 | 8/2009 |

OTHER PUBLICATIONS

Kubinyi ed. 3D QSAR in Drug Design: Ligand-Protein Interactions and Molecular Similarity, vol. 2-3, Springer, 1998, 800 pages, relevant portion attached.*

Altland H.W., et al., A Facile Synthesis of 2-Aminothiazolo[5,4-b]- and 2-Aminothiazolo [4,5-c] pyridines, Journal of Heterocyclic Chemistry, Jan. 1, 1977, pp. 129-134, vol. 14, Heterocorporation. Provo, US.

P. Garay et al., Synthese et etude des activites antiparasitaires et molliscicides de derives polycycliques de la pyridine, European Journal Medicinal Chemistry, 1978, pp. 171-175, vol. 13, No. 2.

P. Garay et al., Synthese et etude des activites antiparasitaires et molliscicides de derives polycycliques de la pyridine, European Journal Medicinal Chemistry, 1978, pp. 171-175, vol. 13, No. 2. (English_Translation).

Patil V.H., et al., Synthesis of some sulphanilamido-benzothiazolyl thiazole derivatives as antibacterial agents, Journal of the Indian Chemical Society, Dec. 1, 1979, pp. 1243-1245, vol. 56, No. 12, The Indian Chemical Society, Calcutta, IN.

Patil V.H., et al., Synthesis of 2-arylamino-4- not 2'-(P-Acetamido-Benzenesulphonamido)-6'-Benzothiazolyl 3/4 Thiazoles & 2-Arylamino-4-(2'-Sulphanilamido-6' -Benzothiazolyl)Thiazoles, Indian Journal of Chemistry, Section B: Organic, Incl. Medicinal, Jan. 1, 1979, pp. 519-521, vol. 17B, No. 5, Publications & Informations Directorate, New Delhi, IN.

Cosulich et al., New Thiazole Pyridine Sulfonamides as Orally Bioavailable Highly Potent PI3 Kinase Inhibitors, Cancer and Infection Research Area. AstraZeneca, Alderley Park, Cheshire, UK. Keystone Conference Presentation, New Mexico, Feb. 15-20, 2007.

Camps et al., Blockade of PI3K gamma Suppresses Joint Inflammation and Damage in Mouse Models of Rheumatoid Arthritis, Nature Medicine, Sep. 2005, pp. 936-943, vol. 11, No. 9.

Hayakawa, et al., Synthesis and Biological Evaluation of Imidazo[1,2-alpha]pyridine derivatives as novel PI3 kinase p110alpha Inhibitors, Bioorganic and Medical Chemistry, 2007, pp. 403-412, vol. 15.

Knight, et al., A Pharmacological Map of the PI3-K Family Defines a Role for p110alpha in Insulin Signaling, Cell, May 19, 2006. pp. 733-747, vol. 125.

Knight, et al., Supplemental Data—A Pharmacological Map of the PI3-K Family Defines a Role for p110alpha in Insulin Signaling, Cell, May 19, 2006, pp. 733-747, vol. 125.

Partial International Search Report, International Application No. PCT/US2008/013940.

International Search Report, International Application No. PCT/US2008/009312.

* cited by examiner

IMIDAZOPYRIDAZINE INHIBITORS OF PI3 KINASE FOR CANCER TREATMENT

CROSS-REFERENCE TO RELATED APPLICATION

This application claims priority to U.S. provisional patent application No. 61/008,430, filed Dec. 19, 2007, which is herein incorporated by reference in its entirety.

FIELD OF THE INVENTION

The present invention relates to compounds that inhibit phosphoinositide 3-kinase (PI3K); methods of treating diseases or conditions, such as cancer, using the compounds; and pharmaceutical compositions containing the compounds.

BACKGROUND OF THE INVENTION

PI3 kinases are a family of lipid kinases that have been found to play a key role in the regulation of many cellular processes including proliferation, survival, carbohydrate metabolism, and motility. PI3Ks are considered to have an important role in intracellular signal transduction. In particular, the PI3Ks generate and convey signals that have important roles in cancer. PI3Ks are ubiquitously expressed, are activated by a high proportion of cell surface receptors, especially those linked to tyrosine kinases, and influence a variety of cellular functions and events. Although some PI3K activity is likely to be essential for cellular health, PI3Ks are a diverse group of enzymes for which there is increasing evidence of functional specialization. This opens up the possibility of developing isoform-selective inhibitors that can be used to treat cancer.

The primary enzymatic activity of PI3K is the phosphorylation of inositol lipids (phosphoinositides) on the 3-position of the inositol headgroup. PI3 kinases catalyze the addition of phosphate to the 3'-OH position of the inositol ring of inositol lipids generating phosphatidyl inositol monophosphate, phosphatidyl inositol diphosphate and phosphatidyl inositol triphosphate.

There are a total of eight mammalian PI3Ks, which have been divided into three main classes on the basis of sequence homology, in vitro substrate preference, and method of activation and regulation. Enzymes of a first class (Class I) have a broad substrate specificity and phosphorylate phosphatidylinositiol (PtdIns), PtdIns(4)P and PtdIns(4,5)P$_2$. Class I PI3 kinases include mammalian p110α, p110β, p110δ and p110γ. Different members of the PI3-kinase family generate different lipid products. To date, four 3-phosphorylated inositol lipids have been identified in vivo. These lipids are bound by proteins that contain the appropriate lipid recognition module and which either act as effectors or transmit the PI3K signal onwards. The most familiar form of PI3K is a heterodimeric complex, consisting of a 110 kDa catalytic subunit now known as pI110α and an 85 kDa regulatory/adapter subunit, p85α.

Phosphatidylinositol 3-kinase-alpha (PI3Kα), a dual specificity lipid and protein kinase, is composed of an 85 kDa regulatory subunit and a 110 kDa catalytic subunit. The protein includes a catalytic subunit, which uses ATP to phosphorylate PtdIns, PtdIns(4)P and PtdIns(4,5)P$_2$. PTEN, a tumor suppressor, can dephosphorylate phosphatidylinositol (3,4,5)-trisphosphate (PIP3), the major product of PI3 kinase Class I. PIP3, in turn, is required for translocation of protein kinase B (AKT1, PKB) to the cell membrane, where it is phosphorylated and activated by upstream kinases. The effect of PTEN on cell death is mediated through the PI3Kα/AKT1 pathway.

PI3Kα has been implicated in the control of cytoskeletal reorganization, apoptosis, vesicular trafficking and proliferation and differentiation processes. Increased copy number and expression of the p110α gene (PIK3CA) is associated with a number of cancers such as ovarian cancer, cervical cancer, breast cancer, colon cancer, rectal cancer, endometrial cancer, stomach cancer, liver cancer, lung cancer, thyroid cancer, acute myelogenous leukemia (AML), chronic myelogenous leukemia (CML), and glioblastomas. In view of the important role of PI3Kα in biological processes and disease states, inhibitors of this kinase are desirable. The present invention provides PI3K inhibitors, particularly PI3Kα inhibitors, which are useful for treating PI3Kα-mediated diseases and conditions.

SUMMARY OF THE INVENTION

The invention provides compounds of Formula I

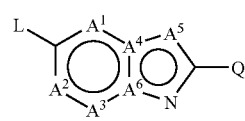

or the pharmaceutically acceptable salts thereof, wherein
Q is —NR$^1$R$^1$, —NR$^1$C(=O)R$^1$, —S(=O)$_2$NR$^1$R$^1$, —S(=O)$_2$R$^1$, —NR$^1$S[(=O)$_2$R$^1$], —C(=O)NR$^1$R$^1$, —C(=O)R$^1$, —C(=O)OR$^1$, —NR$^1$C(=O)NR$^1$R$^1$, —NR$^1$C(=O)OR$^1$, or —NR$^1$S(=O)$_2$NR$^1$R$^1$;

each R$^1$ is independently hydrogen, C$_1$-C$_8$ alkyl, substituted C$_1$-C$_8$ alkyl, C$_2$-C$_8$ alkenyl, substituted C$_2$-C$_8$ alkenyl, C$_2$-C$_8$ alkynyl, substituted C$_2$-C$_8$ alkynyl, C$_3$-C$_8$cycloalkyl, substituted C$_3$-C$_8$cycloalkyl, heterocycloalkyl, substituted heterocycloalkyl, aryl, substituted aryl, heteroaryl or substituted heteroaryl;

L is

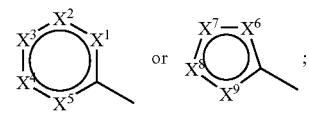

X$^1$, X$^2$, X$^3$, X$^4$ and X$^5$ are each independently CR, CR$^2$ or N, provided that no more than three of X$^1$, X$^2$, X$^3$, X$^4$ and X$^5$ are N and one of X$^1$, X$^2$, X$^3$, X$^4$ and X$^5$ is CR$^2$;

X$^6$, X$^7$, X$^8$ and X$^9$ are each independently CR, CR$^2$, N, O or S, provided that no more than three of X$^6$, X$^7$, X$^8$ and X$^9$ are N, O or S and one of X$^6$, X$^7$, X$^8$ and X$^9$ is CR$^2$;

each R$^2$ is independently —SR$^1$, —OR$^1$—S(=O)$_2$R$^1$, —NR$^1$[S(=O)$_2$R$^1$],

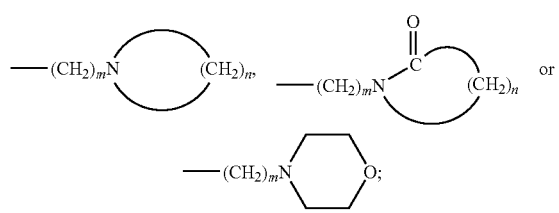

each n is independently 2 to 5;
each m is independently 0 to 6;
A$^1$, A$^2$, A$^3$ and A$^5$ are each independently CR or N;

$A^4$ and $A^6$ are each independently C or N, provided that no more than three of $A^1$, $A^2$, $A^3$, $A^4$, $A^5$ and $A^6$ are N; and each R is independently halogen, hydrogen, cyano, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, —O$C_1$-$C_8$ alkyl, —O(substituted $C_1$-$C_8$ alkyl); $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl.

In an embodiment of the compounds of Formula I, or the pharmaceutically acceptable salts thereof, either alone or in combination with any of the above or below embodiments, $A^1$ and $A^4$ are N; $A^2$, $A^3$ and $A^5$ are CR; and $A^6$ is C.

In another embodiment of the compounds of Formula I, or the pharmaceutically acceptable salts thereof, either alone or in combination with any of the above or below embodiments, $A^1$, $A^2$, $A^3$ and $A^5$ are CR; $A^4$ is N; and $A^6$ is C.

In another embodiment of the compounds of Formula I, or the pharmaceutically acceptable salts thereof, either alone or in combination with any of the above or below embodiments, $A^1$ and $A^4$ are N; $A^2$, $A^3$ and $A^5$ are CR; $A^6$ is C; and Q is —$NR^1R^1$, —$NR^1C(=O)R^1$, —$NR^1[S(=O)_2R^1]$, —$C(=O)NR^1R^1$, —$C(=O)R^1$, —$C(=O)OR^1$, —$NR^1C(=O)NR^1R^1$, —$NR^1C(=O)OR^1$, or —$NR^1S(=O)_2NR^1R^1$.

In another embodiment of the compounds of Formula I, or the pharmaceutically acceptable salts thereof, either alone or in combination with any of the above or below embodiments, $A^1$, $A^2$, $A^3$ and $A^5$ are CR; $A^4$ is N; $A^6$ is C; and Q is —$NR^1R^1$, —$NR^1C(=O)R^1$, —$NR^1[S(=O)_2R^1]$, —$C(=O)NR^1R^1$, —$C(=O)R^1$, —$C(=O)OR^1$, —$NR^1C(=O)NR^1R^1$, —$NR^1C(=O)OR^1$, or —$NR^1S(=O)_2NR^1R^1$.

In another embodiment of the compounds of Formula I, or the pharmaceutically acceptable salts thereof, either alone or in combination with any of the above or below embodiments, Q is —$NR^1C(=O)R^1$.

In another embodiment of the compounds of Formula I, or the pharmaceutically acceptable salts thereof, either alone or in combination with any of the above or below embodiments, Q is —$NHC(=O)CH_3$.

In another embodiment of the compounds of Formula I, or the pharmaceutically acceptable salts thereof, either alone or in combination with any of the above or below embodiments, Q is —$NHC(=O)CH_3$; $A^1$ and $A^4$ are N; $A^2$, $A^3$ and $A^5$ are CH; and $A^6$ is C.

In another embodiment of the compounds of Formula I, or the pharmaceutically acceptable salts thereof, either alone or in combination with any of the above or below embodiments, Q is —$NHC(=O)CH_3$; $A^1$, $A^2$, $A^3$ and $A^5$ are CH; $A^4$ is N; and $A^6$ is C.

In another embodiment of the compounds of Formula I, or the pharmaceutically acceptable salts thereof, either alone or in combination with any of the above or below embodiments, L is

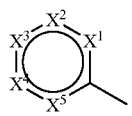

$X^4$ is N; and $X^1$, $X^3$ and $X^5$ are CR; and $X^2$ is $CR^2$.

In another embodiment of the compounds of Formula I, or the pharmaceutically acceptable salts thereof, either alone or in combination with any of the above or below embodiments, L is

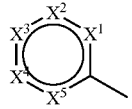

$X^1$, $X^3$, $X^4$ and $X^5$ are CR; and $X^2$ is $CR^2$.

In another embodiment of the compounds of Formula I, or the pharmaceutically acceptable salts thereof, either alone or in combination with any of the above or below embodiments, L is

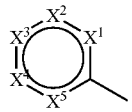

$X^1$, $X^3$, $X^4$ and $X^5$ are CH; and $X^2$ is $CR^2$.

In another embodiment of the compounds of Formula I, or the pharmaceutically acceptable salts thereof, either alone or in combination with any of the above or below embodiments, L is

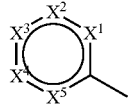

$X^1$ and $X^3$ are N; $X^4$ and $X^5$ are CR; and $X^2$ is $CR^2$.

In another embodiment of the compounds of Formula I, or the pharmaceutically acceptable salts thereof, either alone or in combination with any of the above or below embodiments, $A^1$ and $A^4$ are N; $A^2$, $A^3$ and $A^5$ are CH; $A^6$ is C;

L is

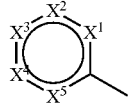

$X^4$ is N; $X^1$, $X^3$ and $X^5$ are CH; $X^2$ is $CR^2$; Q is —$NHC(=O)CH_3$; and $R^2$ is —$S(=O)_2R^1$ or —$NR^1[S(=O)_2R^1]$.

In another embodiment of the compounds of Formula I, or the pharmaceutically acceptable salts thereof, either alone or in combination with any of the above or below embodiments, $A^1$ and $A^4$ are N; $A^2$, $A^3$ and $A^5$ are CH; $A^6$ is C;

L is

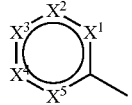

$X^1$, $X^3$, $X^4$ and $X^5$ are CH; $X^2$ is $CR^2$; Q is —NHC(=O)CH$_3$; and $R^2$ is —S(=O)$_2R^1$ or —NR[S(=O)$_2R^1$].

In another embodiment of the compounds of Formula I, or the pharmaceutically acceptable salts thereof, either alone or in combination with any of the above or below embodiments, $A^4$ is N; $A^1$, $A^2$, $A^3$ and $A^5$ are CH; $A^6$ is C;

L is

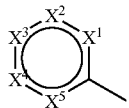

$X^4$ is N; $X^1$, $X^3$ and $X^5$ are CH; $X^2$ is $CR^2$; Q is —NHC(=O)CH$_3$; and $R^2$ is —S(=O)$_2R^1$ or —NR$^1$[S(=O)$_2R^1$].

In another embodiment of the compounds of Formula I, or the pharmaceutically acceptable salts thereof, either alone or in combination with any of the above or below embodiments, $A^4$ is N; $A^1$, $A^2$, $A^3$ and $A^5$ are CH; $A^6$ is C;

L is

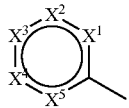

$X^1$, $X^3$, $X^4$ and $X^5$ are CH; $X^2$ is $CR^2$; Q is —NHC(=O)CH$_3$; and $R^2$ is —S(=O)$_2R^1$ or —NR$^1$[S(=O)$_2R^1$].

In another embodiment of the compounds of Formula I, or the pharmaceutically acceptable salts thereof, either alone or in combination with any of the above or below embodiments, L is

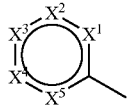

and $X^2$ is $CR^2$.

The invention provides the compounds:
N-(6-(3-(4-methylphenylsulfonamido)phenyl)imidazo[1,2-b]pyridazin-2-yl)acetamide;
N-(6-(3-(N,4-dimethylphenylsulfonamido)phenyl)imidazo[1,2-b]pyridazin-2-yl)acetamide;
N-(6-(2-fluoropyridin-4-yl)imidazo[1,2-b]pyridazin-2-yl)acetamide;
N-(6-(2-(2-fluorophenylthio)pyridin-4-yl)imidazo[1,2-b]pyridazin-2-yl)acetamide;
N-(6-(3-(isoquinoline-5-sulfonamido)phenyl)imidazo[1,2-b]pyridazin-2-yl)acetamide;
N-(6-(3-(naphthalene-1-sulfonamido)phenyl)imidazo[1,2-b]pyridazin-2-yl)acetamide;
N-(6-(5-(methylthio)pyridin-3-yl)imidazo[1,2-b]pyridazin-2-yl)acetamide;
N-(6-(3-(methylthio)phenyl)imidazo[1,2-b]pyridazin-2-yl)acetamide;
N-(6-(5-(methylsulfonyl)pyridin-3-yl)imidazo[1,2-b]pyridazin-2-yl)acetamide;
N-(6-(5-(4-fluorophenylsulfonamido)pyridin-3-yl)imidazo[1,2-a]pyridazin-2-yl)acetamide;
N-(6-(2-(4-methoxy-N-methylphenylsulfonamido)pyridin-4-yl)H-imidazo[1,2-a]pyridin-2-yl)acetamide;
N-(6-(5-(4-fluorophenylsulfonamido)pyridin-3-yl)H-imidazo[1,2-a]pyridin-2-yl)acetamide;
N-(6-(5-(cyclopropanesulfonamido)pyridin-3-yl)H-imidazo[1,2-a]pyridin-2-yl)acetamide;
N-(6-(5-(methylsulfonamido)pyridin-3-yl)H-imidazo[1,2-a]pyridin-2-yl)acetamide;
N-(5-(6-phenyl-[1,2,4]triazolo[4,3-b]pyridazin-3-yl)pyridin-3-yl)benzenesulfonamide;
N-(6-(6-chloro-5-(4-fluorophenylsulfonamido)pyridin-3-yl)imidazo[1,2-b]pyridazin-2-yl)acetamide;
N-(6-(5-(4-methylphenylsulfonamido)pyridin-3-yl)imidazo[1,2-a]pyrazin-2-yl)acetamide;
N-(6-(5-(isopropylamino)-6-(2-morpholinoethylamino)pyridin-3-yl)imidazo[1,2-b]pyridazin-2-yl)acetamide;
N-(6-(5-(dimethylamino)-6-(2-morpholinoethoxy)pyridin-3-yl)imidazo[1,2-b]pyridazin-2-yl)acetamide;
1-(6-(6-chloro-4-isopropoxypyridin-3-yl)H-imidazo[1,2-a]pyridin-2-yl)-3-(2-(piperidin-1-yl)ethyl)urea;
N-(6-(5-(isopropylamino)-6-(trifluoromethyl)pyridin-3-yl)imidazo[1,2-b]pyridazin-2-yl)acetamide;
N-(6-(5-(dimethylamino)-6-(2-morpholinoethylamino)pyridin-3-yl)imidazo[1,2-b]pyridazin-2-yl)acetamide;
1-(6-(6-chloro-5-(dimethylamino)pyridin-3-yl)imidazo[1,2-b]pyridazin-2-yl)-3-(2-(piperidin-1-yl)ethyl)urea;
1-(6-(4-isopropoxy-6-methoxypyridin-3-yl)H-imidazo[1,2-a]pyridin-2-yl)-3-(2-(piperidin-1-yl)ethyl)urea;
1-(6-(6-cyano-5-isopropoxypyridin-3-yl)imidazo[1,2-b]pyridazin-2-yl)-3-(2-(piperidin-1-yl)ethyl)urea;
N-(6-(6-chloro-5-(4-(trifluoromethyl)phenylsulfonamido)pyridin-3-yl)imidazo[1,2-b]pyridazin-2-yl)acetamide;
N-(6-(5-(4-tert-butylphenylsulfonamido)-6-cyanopyridin-3-yl)imidazo[1,2-b]pyridazin-2-yl)acetamide;
N-(6-(5-(4-tert-butylphenylsulfonamido)-6-chloropyridin-3-yl)imidazo[1,2-b]pyridazin-2-yl)acetamide; or
N-(6-(5-(4-tert-butylphenylsulfonamido)-6-ethynylpyridin-3-yl)imidazo[1,2-b]pyridazin-2-yl)acetamide, or a pharmaceutically acceptable salt thereof.

The invention also provides pharmaceutical compositions comprising:

A) a compound of Formula I

or a pharmaceutically acceptable salt thereof, wherein

Q is —NR$^1R^1$, —NR$^1$C(=O)R$^1$, —S(=O)$_2$NR$^1R^1$, —S(=O)$_2R'$, —NR$^1$[S(=O)$_2R^1$], —C(=O)NR$^1R^1$, —C(=O)R$^1$, —C(=O)OR$^1$, —NR$^1$C(=O)NR$^1R^1$, —NR$^1$C(=O)OR$^1$, or —NR$^1$S(=O)$_2$NR$^1R^1$;

each $R^1$ is independently hydrogen, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl;

L is

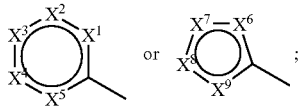

$X^1$, $X^2$, $X^3$, $X^4$ and $X^5$ are each independently CR, $CR^2$ or N, provided that no more than three of $X^1$, $X^2$, $X^3$, $X^4$ and $X^5$ are N and one of $X^1$, $X^2$, $X^3$, $X^4$ and $X^5$ is $CR^2$;

$X^6$, $X^7$, $X^8$ and $X^9$ are each independently CR, $CR^2$, N, O or S, provided that no more than three of $X^6$, $X^7$, $X^8$ and $X^9$ are N, O or S and one of $X^6$, $X^7$, $X^8$ and $X^9$ is $CR^2$ each $R^2$ is independently —$SR^1$, —$OR^1$—$S(=O)_2R^1$, —$NR^1[S(=O)_2R^1]$,

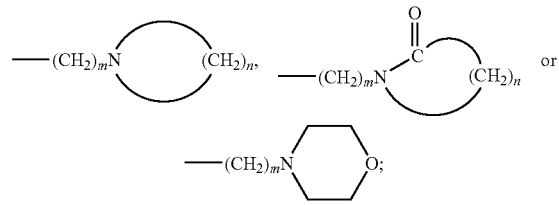

each n is independently 2 to 5;
each m is independently 0 to 6;
$A^1$, $A^2$, $A^3$ and $A^5$ are each independently CR or N;
$A^4$ and $A^6$ are each independently C or N, provided that no more than three of $A^1$, $A^2$, $A^3$, $A^4$, $A^5$ and $A^6$ are N; and each R is independently halogen, hydrogen, cyano, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, —$OC_1$-$C_8$ alkyl, —O(substituted $C_1$-$C_8$ alkyl); $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl; and B) a pharmaceutically acceptable excipient.

The invention also provides methods of treating melanoma, ovarian cancer, cervical cancer, breast cancer, colon cancer, rectal cancer, endometrial cancer, pancreatic cancer, lung cancer, stomach cancer, glioblastoma, liver cancer, prostate cancer, acute lyelogeous leukemia, chronic lyelogenous leukemia, or thyroid cancer, the methods comprising administering to a patient in need thereof a therapeutically effective amount of a compound of Formula I

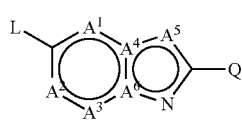

or a pharmaceutically acceptable salt thereof, wherein

Q is —$NR^1R^1$, —$NR^1C(=O)R^1$, —$S(=O)_2NR^1R^1$, —$S(=O)_2R^1$, —$NR^1[S(=O)_2R^1]$, —$C(=O)NR^1R^1$, —$C(=O)R^1$, —$C(=O)OR^1$, —$NR^1C(=O)NR^1R^1$, —$NR^1C(=O)OR^1$, or —$NR^1S(=O)_2NR^1R^1$;

each $R^1$ is independently hydrogen, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl;

L is

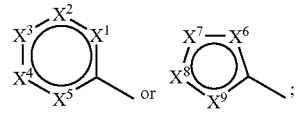

$X^1$, $X^2$, $X^3$, $X^4$ and $X^1$ are each independently CR, $CR^2$ or N, provided that no more than three of $X^1$, $X^2$, $X^3$, $X^4$ and $X^5$ are N and one of $X^1$, $X^2$, $X^3$, $X^4$ and $X^5$ is $CR^2$;

$X^6$, $X^7$, $X^8$ and $X^9$ are each independently CR, $CR^2$, N, O or S, provided that no more than three of $X^6$, $X^7$, $X^8$ and $X^9$ are N, O or S and one of $X^6$, $X^7$, $X^8$ and $X^9$ is $CR^2$;

each $R^2$ is independently —$SR^1$, —$OR^1$—$S(=O)_2R^1$, —$NR^1[S(=O)_2R^1]$, each n is independently 2 to 5;
each m is independently 0 to 6;
$A^1$, $A^2$, $A^3$ and $A^5$ are each independently CR or N;
$A^4$ and $A^6$ are each independently C or N, provided that no more than three of $A^1$, $A^2$, $A^3$, $A^4$, $A^5$ and $A^6$ are N; and each R is independently halogen, hydrogen, cyano, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, —$OC_1$-$C_8$ alkyl, —O(substituted $C_1$-$C_8$ alkyl); $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl.

In an embodiment of the methods, the compounds of Formula I are:

N-(6-(3-(4-methylphenylsulfonamido)phenyl)imidazo[1,2-b]pyridazin-2-yl)acetamide;

N-(6-(3-(N,4-dimethylphenylsulfonamido)phenyl)imidazo[1,2-b]pyridazin-2-yl)acetamide;

N-(6-(2-fluoropyridin-4-yl)imidazo[1,2-b]pyridazin-2-yl)acetamide;

N-(6-(2-(2-fluorophenylthio)pyridin-4-yl)imidazo[1,2-b]pyridazin-2-yl)acetamide;

N-(6-(3-(isoquinoline-5-sulfonamido)phenyl)imidazo[1,2-b]pyridazin-2-yl)acetamide;

N-(6-(3-(naphthalene-1-sulfonamido)phenyl)imidazo[1,2-b]pyridazin-2-yl)acetamide;

N-(6-(5-(methylthio)pyridin-3-yl)imidazo[1,2-b]pyridazin-2-yl)acetamide;

N-(6-(3-(methylthio)phenyl)imidazo[1,2-b]pyridazin-2-yl)acetamide;

N-(6-(5-(methylsulfonyl)pyridin-3-yl)imidazo[1,2-b]pyridazin-2-yl)acetamide;

N-(6-(5-(4-fluorophenylsulfonamido)pyridin-3-yl)imidazo[1,2-b]pyridazin-2-yl)acetamide;

N-(6-(2-(4-methoxy-N-methylphenylsulfonamido)pyrimidin-4-yl)H-imidazo[1,2-a]pyridin-2-yl)acetamide;
N-(6-(5-(4-fluorophenylsulfonamido)pyridin-3-yl)H-imidazo[1,2-a]pyridin-2-yl)acetamide;
N-(6-(5-(cyclopropanesulfonamido)pyridin-3-yl)H-imidazo[1,2-a]pyridin-2-yl)acetamide;
N-(6-(5-(methylsulfonamido)pyridin-3-yl)H-imidazo[1,2-a]pyridin-2-yl)acetamide;
N-(5-(6-phenyl-[1,2,4]triazolo[4,3-b]pyridazin-3-yl)pyridin-3-yl)benzenesulfonamide;
N-(6-(6-chloro-5-(4-fluorophenylsulfonamido)pyridin-3-yl)imidazo[1,2-b]pyridazin-2-yl)acetamide;
N-(6-(5-(4-methylphenylsulfonamido)pyridin-3-yl)imidazo[1,2-a]pyrazin-2-yl)acetamide;
N-(6-(5-(isopropylamino)-6-(2-morpholinoethylamino)pyridin-3-yl)imidazo[1,2-b]pyridazin-2-yl)acetamide;
N-(6-(5-(dimethylamino)-6-(2-morpholinoethoxy)pyridin-3-yl)imidazo[1,2-b]pyridazin-2-yl)acetamide;
1-(6-(6-chloro-4-isopropoxypyridin-3-yl)H-imidazo[1,2-a]pyridin-2-yl)-3-(2-(piperidin-1-yl)ethyl)urea;
N-(6-(5-(isopropylamino)-6-(trifluoromethyl)pyridin-3-yl)imidazo[1,2-b]pyridazin-2-yl)acetamide;
N-(6-(5-(dimethylamino)-6-(2-morpholinoethylamino)pyridin-3-yl)imidazo[1,2-b]pyridazin-2-yl)acetamide;
1-(6-(6-chloro-5-(dimethylamino)pyridin-3-yl)imidazo[1,2-b]pyridazin-2-yl)-3-(2-(piperidin-1-yl)ethyl)urea;
1-(6-(4-isopropoxy-6-methoxypyridin-3-yl)H-imidazo[1,2-a]pyridin-2-yl)-3-(2-(piperidin-1-yl)ethyl)urea;
1-(6-(6-cyano-5-isopropoxypyridin-3-yl)imidazo[1,2-b]pyridazin-2-yl)-3-(2-(piperidin-1-yl)ethyl)urea;
N-(6-(6-chloro-5-(4-(trifluoromethyl)phenylsulfonamido)pyridin-3-yl)imidazo[1,2-b]pyridazin-2-yl)acetamide;
N-(6-(5-(4-tert-butylphenylsulfonamido)-6-cyanopyridin-3-yl)imidazo[1,2-b]pyridazin-2-yl)acetamide;
N-(6-(5-(4-tert-butylphenylsulfonamido)-6-chloropyridin-3-yl)imidazo[1,2-b]pyridazin-2-yl)acetamide; or
N-(6-(5-(4-tert-butylphenylsulfonamido)-6-ethynylpyridin-3-yl)imidazo[1,2-b]pyridazin-2-yl)acetamide, or the pharmaceutically acceptable salts thereof.

In another embodiment of the methods, an additional pharmaceutically active compound is administered to the patient, which compound is selected from the group consisting of antineoplastic agents; anti-angiogenic agents; chemotherapeutic agents and peptidal cancer therapy agents.

In another embodiment of the methods with an additional pharmaceutically active compound, the additional pharmaceutically active compound is an antineoplastic agent and the antineoplastic agent is selected from the group consisting of antibiotic-type agents; alkylating agents; antimetabolite agents; hormonal agents; immunological agents; interferon-type agents; and kinase inhibitors.

In an alternative embodiment, the invention provides compounds of Formula I

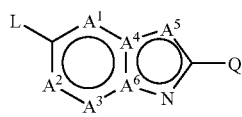

I or a pharmaceutically acceptable salt thereof, wherein
Q is —$NR^1R^1$, —$NR^1C(=O)R^1$, —$S(=O)_2NR^1R^1$, —$S(=O)_2R^1$, —$NR^1[S(=O)_2R^1]$, —$C(=O)NR^1R^1$, —$C(=O)R^1$, —$C(=O)OR^1$, —$NR^1C(=O)NR^1R^1$, —$NR^1C(=O)OR^1$, or —$NR^1S(=O)_2NR^1R^1$ (where $R^1R^1$ of $NR^1R^1$, where it occurs, can join together with the nitrogen atom to which they are attached to form a $C_3$-$C_8$ heterocycloalkyl ring);

each $R^1$ is independently hydrogen, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, $C_3$-$C_8$ cycloalkyl, substituted $C_3$-$C_8$ cycloalkyl, heterocycloalkyl, substituted heterocycloalkyl, aryl, substituted aryl, heteroaryl or substituted heteroaryl;

L is

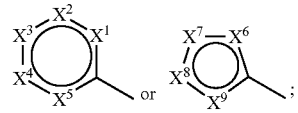

$X^1$, $X^2$, $X^3$, $X^4$ and $X^5$ are each independently CR, $CR^2$ or N, provided that no more than three of $X^1$, $X^2$, $X^3$, $X^4$ and $X^5$ are N and one of $X^1$, $X^2$, $X^3$, $X^4$ and $X^5$ is $CR^2$;

$X^6$, $X^7$, $X^8$ and $X^9$ are each independently CR, $CR^2$, N, O or S, provided that no more than three of $X^6$, $X^7$, $X^8$ and $X^9$ are N, O or S and one of $X^6$, $X^7$, $X^8$ and $X^9$ is $CR^2$;

each $R^2$ is independently halogen, —$SR^1$, —$OR^1$—$S(=O)_2R^1$, —$NR^1[S(=O)_2R^1]$, or —$NR^1S(=O)_2NR^1R^1$ (where $R^1R^1$ of $NR^1R^1$, where it occurs, can join together with the nitrogen atom to which they are attached to form a $C_3$-$C_8$ heterocycloalkyl ring),

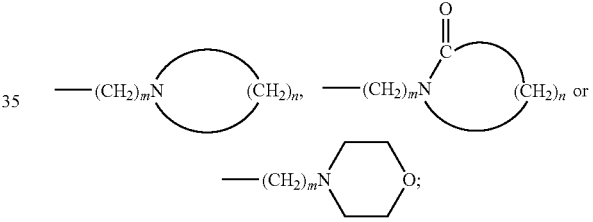

each n is independently 2 to 5;
each m is independently 0 to 6;
$A^1$, $A^2$ and $A^3$ are each independently CR or N;
$A^5$ is CR, N, or NR;
$A^4$ and $A^6$ are each independently C or N, provided that no more than three of $A^1$, $A^2$, $A^3$, $A^4$, $A^5$ and $A^6$ are N or NR; and
each R is independently halogen, hydrogen, cyano, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, —$OC_1$-$C_8$ alkyl, —O(substituted $C_1$-$C_8$ alkyl); $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl.

In another embodiment of the compounds of Formula I, or the pharmaceutically acceptable salts thereof, either alone or in combination with any of the above or below embodiments $A^2$, $A^3$ and $A^5$ are CR; and $A^6$ is C.

In another embodiment of the compounds of Formula I, or the pharmaceutically acceptable salts thereof, either alone or in combination with any of the above or below embodiments $A^1$, $A^2$, $A^3$ and $A^5$ are CR; $A^4$ is N; and $A^6$ is C.

In another embodiment of the compounds of Formula I, or the pharmaceutically acceptable salts thereof, either alone or in combination with any of the above or below embodiments, $A^1$ and $A^4$ are N; $A^2$, $A^3$ and $A^5$ are CR; $A^6$ is C; and Q is —$NR^1R^1$, —$NR^1C(=O)R^1$, —$NR^1[S(=O)_2R^1]$, —$C(=O)$ $NR^1R^1$, —C(=O)$R^1$, —C(=O)O$R^1$, —$NR^1$C(=O)$NR^1R^1$, —$NR^1$C(=O)O$R^1$, or —$NR^1$S(=O)$_2NR^1R^1$.

In another embodiment of the compounds of Formula I, or the pharmaceutically acceptable salts thereof, either alone or in combination with any of the above or below embodiments $A^1, A^2, A^3$ and $A^5$ are CR; $A^4$ is N; $A^6$ is C; and Q is —$NR^1R^1$, —$NR^1$C(=O)$R^1$, —$NR^1$[S(=O)$_2R^1$], —C(=O)$NR^1R^1$, —C(=O)$R^1$, —C(=O)O$R^1$, —$NR^1$C(=O)$NR^1R^1$, —$NR^1$C(=O)O$R^1$, or —$NR^1$S(=O)$_2NR^1R^1$.

In another embodiment of the compounds of Formula I, or the pharmaceutically acceptable salts thereof, either alone or in combination with any of the above or below embodiments Q is —$NR^1$C(=O)$R^1$.

In another embodiment of the compounds of Formula I, or the pharmaceutically acceptable salts thereof, either alone or in combination with any of the above or below embodiments Q is —NHC(=O)CH$_3$.

In another embodiment of the compounds of Formula I, or the pharmaceutically acceptable salts thereof, either alone or in combination with any of the above or below embodiments Q is —NHC(=O)CH$_3$; $A^1$ and $A^4$ are N; $A^2$, $A^3$ and $A^5$ are CH; and $A^6$ is C.

In another embodiment of the compounds of Formula I, or the pharmaceutically acceptable salts thereof, either alone or in combination with any of the above or below embodiments Q is —NHC(=O)CH$_3$; $A^1$, $A^2$, $A^3$ and $A^5$ are CH; $A^4$ is N; and $A^6$ is C.

In another embodiment of the compounds of Formula I, or the pharmaceutically acceptable salts thereof, either alone or in combination with any of the above or below embodiments L is $X^4$ is N; and $X^1$, $X^3$ and $X^5$ are CR; and $X^2$ is $CR^2$.

In another embodiment of the compounds of Formula I, or the pharmaceutically acceptable salts thereof, either alone or in combination with any of the above or below embodiments L is $X^1$, $X^3$, $X^4$ and $X^5$ are CR; and $X^2$ is $CR^2$.

In another embodiment of the compounds of Formula I, or the pharmaceutically acceptable salts thereof, either alone or in combination with any of the above or below embodiments L is $X^1$, $X^3$, $X^4$ and $X^5$ are CH; and $X^2$ is $CR^2$.

In another embodiment of the compounds of Formula I, or the pharmaceutically acceptable salts thereof, either alone or in combination with any of the above or below embodiments L is $X^1$ and $X^3$ are N; $X^4$ and $X^5$ are CR; and $X^2$ is $CR^2$.

In another embodiment of the compounds of Formula I, or the pharmaceutically acceptable salts thereof, either alone or in combination with any of the above or below embodiments $A^1$ and $A^4$ are N; $A^2$, $A^3$ and $A^5$ are CH; $A^6$ is C;

L is $X^4$ is N; $X^1$, $X^3$ and $X^5$ are CH; $X^2$ is $CR^2$; Q is —NHC(=O)CH$_3$; and $R^2$ is —S(=O)$_2R^1$, —$NR^1$[S(=O)$_2R^1$], or —$NR^1$S(=O)$_2NR^1R^1$.

In another embodiment of the compounds of Formula I, or the pharmaceutically acceptable salts thereof, either alone or in combination with any of the above or below embodiments $A^1$ and $A^4$ are N; $A^2$, $A^3$ and $A^5$ are CH; $A^6$ is C;

L is $X^1$, $X^3$, $X^4$ and $X^5$ are CH; $X^2$ is $CR^2$; Q is —NHC(=O)CH$_3$; and $R^2$ is —S(=O)$_2R^1$, —NR[S(=O)$_2R^1$], or —$NR^1$S(=O)$_2NR^1R^1$.

In another embodiment of the compounds of Formula I, or the pharmaceutically acceptable salts thereof, either alone or in combination with any of the above or below embodiments $A^4$ is N; $A^1$, $A^2$, $A^3$ and $A^5$ are CH; $A^6$ is C;

L is $X^4$ is N; $X^1$, $X^3$ and $X^5$ are CH; $X^2$ is $CR^2$; Q is —NHC(=O)CH$_3$; and $R^2$ is —S(=O)$_2R^1$, or —$NR^1$[S(=O)$_2R^1$], or —$NR^1$S(=O)$_2NR^1R^1$.

In another embodiment of the compounds of Formula I, or the pharmaceutically acceptable salts thereof, either alone or in combination with any of the above or below embodiments $A^4$ is N; $A^1$, $A^2$, $A^3$ and $A^5$ are CH; $A^6$ is C;

L is

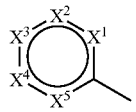

$X^1$, $X^3$, $X^4$ and $X^5$ are CH; $X^2$ is $CR^2$; Q is —NHC(=O)CH$_3$; and $R^2$ is —S(=O)$_2$R$^1$, —NR$^1$[S(=O)$_2$R$^1$], or —NR$^1$S(=O)$_2$NR$^1$R$^1$.

In another embodiment of the compounds of Formula I, or the pharmaceutically acceptable salts thereof, either alone or in combination with any of the above or below embodiments L is

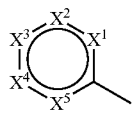

and $X^2$ is $CR^2$.

The present invention provides the compounds:

N-(6-(6-chloro-5-(methylsulfonamido)pyridin-3-yl)imidazo[1,2-b]pyridazin-2-yl)acetamide;

N-(6-(5,6-dimethoxypyridin-3-yl)imidazo[1,2-b]pyridazin-2-yl)acetamide;

N-(6-(6-chloro-5-(methylsulfonamido)pyridin-3-yl)-3-iodoimidazo[1,2-b]pyridazin-2-yl)acetamide;

N-(6-(6-chloro-5-(methylsulfonamido)pyridin-3-yl)-3-(3-fluorophenyl)imidazo[1,2-b]pyridazin-2-yl)acetamide;

N-(5-(2-amino-3-(3-fluorophenyl)imidazo[1,2-b]pyridazin-6-yl)-2-chloropyridin-3-yl)methanesulfonamide;

N-(6-(6-chloro-5-(methylsulfonamido)pyridin-3-yl)-3-(4-fluoro-3-(morpholine-4-carbonyl)phenyl)imidazo[1,2-b]pyridazin-2-yl)acetamide;

5-(2-amino-6-(6-chloro-5-(methylsulfonamido)pyridin-3-yl)imidazo[1,2-b]pyridazin-3-yl)-2-fluorobenzoic acid;

N-(6-(6-chloro-5-(methylsulfonamido)pyridin-3-yl)-3-(pyridin-4-yl)imidazo[1,2-b]pyridazin-2-yl)acetamide;

N-(5-(2-amino-3-(pyridin-4-yl)imidazo[1,2-b]pyridazin-6-yl)-2-chloropyridin-3-yl)methanesulfonamide;

N-(6-(6-chloro-5-(4-fluorophenylsulfonamido)pyridin-3-yl)imidazo[1,2-a]pyridin-2-yl)acetamide;

N-(5-(2-aminoimidazo[1,2-a]pyridin-6-yl)-2-chloropyridin-3-yl)-4-fluorobenzenesulfonamide;

N-(5-(6-chloro-5-(4-fluorophenylsulfonamido)pyridin-3-yl)-1H-benzo[d]imidazol-2-yl)acetamide;

N-(5-(2-amino-1-(pyridin-2-yl)-1H-benzo[d]imidazol-6-yl)-2-chloropyridin-3-yl)-4-fluorobenzenesulfonamide;

N-(6-(6-chloro-5-(4-fluorophenylsulfonamido)pyridin-3-yl)-1-(pyridin-2-yl)-1H-benzo[d]imidazol-2-yl)acetamide;

N-(6-(6-chloro-5-(3-(difluoromethoxy)phenylsulfonamido)pyridin-3-yl)imidazo[1,2-b]pyridazin-2-yl)acetamide;

N-(6-(6-chloro-5-(2-chloro-6-methylphenylsulfonamido)pyridin-3-yl)imidazo[1,2-b]pyridazin-2-yl)acetamide;

N-(6-(6-chloro-5-(4-(2-hydroxypropan-2-yl)phenylsulfonamido)pyridin-3-yl)imidazo[1,2-b]pyridazin-2-yl)acetamide;

N-(5-(2-aminoimidazo[1,2-b]pyridazin-6-yl)-2-chloropyridin-3-yl)-4-fluorobenzenesulfonamide;

N-(6-(6-chloro-5-(4-(1-(methylamino)ethyl)phenylsulfonamido)pyridin-3-yl)imidazo[1,2-b]pyridazin-2-yl)acetamide (mixture of isomers);

N-(6-(6-chloro-5-(4-(1-(methylamino)ethyl)phenylsulfonamido)pyridin-3-yl)imidazo[1,2-b]pyridazin-2-yl)acetamide (Enantiomer 1);

N-(6-(6-chloro-5-(4-(1-(methylamino)ethyl)phenylsulfonamido)pyridin-3-yl)imidazo[1,2-b]pyridazin-2-yl)acetamide (Enantiomer 2);

N-(6-(6-chloro-5-(2-chloro-4-fluorophenylsulfonamido)pyridin-3-yl)imidazo[1,2-b]pyridazin-2-yl)acetamide;

N-(6-(6-chloro-5-(morpholine-4-sulfonamido)pyridin-3-yl)imidazo[1,2-b]pyridazin-2-yl)acetamide;

N-(6-(6-chloro-5-(4-methylphenylsulfonamido)pyridin-3-yl)imidazo[1,2-b]pyriadazin-2-yl)acetamide;

N-(6-(3,4-dimethoxyphenyl)imidazo[1,2-b]pyridazin-2-yl)acetamide;

N-(6-(6-Chloro-5-(3-(difluoromethoxy)phenylsulfonamido)pyridin-3-yl)-3-(pyridin-4-yl)imidazo[1,2-b]pyridazin-2-yl)acetamide;

N-(5-(2-amino-3-(pyridin-4-yl)imidazo[1,2-b]pyridazin-6-yl)-2-chloropyridin-3-yl)-3-(difluoromethoxy)benzenesulfonamide;

N-(6-(6-chloro-5-(3-(difluoromethoxy)phenylsulfonamido)pyridin-3-yl)-3-(2-methylpyridin-4-yl)imidazo[1,2-b]pyridazin-2-yl)acetamide;

N-(5-(2-amino-3-(2-methylpyridin-4-yl)imidazo[1,2-b]pyridazin-6-yl)-2-chloropyridin-3-yl)-3-(difluoromethoxy)benzenesulfonamide;

N-(6-(6-chloro-5-(4-fluorophenylsulfonamido)pyridin-3-yl)-3-(pyridin-4-yl)imidazo[1,2-b]pyridazin-2-yl)acetamide;

N-(6-(6-chloro-5-(3-(difluoromethoxy)phenylsulfonamido)pyridin-3-yl)-3-(pyridin-3-yl)imidazo[1,2-b]pyridazin-2-yl)acetamide;

N-(5-(2-amino-3-(pyridin-3-yl)imidazo[1,2-b]pyridazin-6-yl)-2-chloropyridin-3-yl)-3-(difluoromethoxy)benzenesulfonamide;

N-(5-(2-amino-3-(1,2,3,6-tetrahydropyridin-4-yl)imidazo[1,2-b]pyridazin-6-yl)-2-chloropyridin-3-yl)-3-(difluoromethoxy)benzenesulfonamide;

N-(6-(6-chloro-5-(4-fluorophenylsulfonamido)pyridazin-3-yl)imidazo[1,2-b]pyridazin-2-yl)acetamide; or N-(6-(2-chloropyrimidin-4-yl)H-imidazo[1,2-a]pyridin-2-yl)acetamide, or the pharmaceutically acceptable salts thereof.

The invention also provides pharmaceutical composition comprising:

B) a compound of Formula I

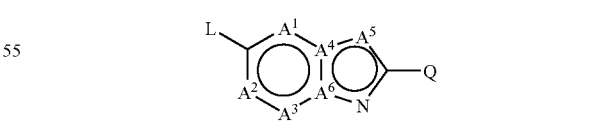

I or a pharmaceutically acceptable salt thereof, wherein
Q is —NR$^1$R$^1$, —NR$^1$C(=O)R$^1$, —S(=O)$_2$NR$^1$R$^1$, —S(=O)$_2$R$^1$, —NR$^1$[S(=O)$_2$R$^1$], —C(=O)NR$^1$R$^1$, —C(=O)R$^1$, —C(=O)OR$^1$, —NR$^1$C(=O)NR$^1$R$^1$, —NR$^1$C(=O)OR$^1$, or —NR$^1$S(=O)$_2$NR$^1$R$^1$ (where R$^1$R$^1$ of NR$^1$R$^1$, where it occurs, can join together with the nitrogen atom to which they are attached to form a C$_3$-C$_8$ heterocycloalkyl ring);

each $R^1$ is independently hydrogen, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl;

L is

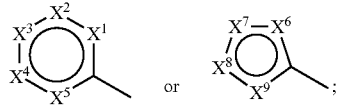

$X^1$, $X^2$, $X^3$, $X^4$ and $X^5$ are each independently CR, $CR^2$ or N, provided that no more than three of $X^1$, $X^2$, $X^3$, $X^4$ and $X^5$ are N and one of $X^1$, $X^2$, $X^3$, $X^4$ and $X^5$ is $CR^2$;

$X^6$, $X^7$, $X^8$ and $X^9$ are each independently CR, $CR^2$, N, O or S, provided that no more than three of $X^6$, $X^7$, $X^8$ and $X^9$ are N, O or S and one of $X^6$, $X^7$, $X^8$ and $X^9$ is $CR^2$;

each $R^2$ is independently halogen, —$SR^1$, —$OR^1$—$S(=O)_2R^1$, —$NR^1[S(=O)_2R^1]$, —$NR^1S(=O)_2NR^1R^1$ (where $R^1R^1$ of $NR^1R^1$, where it occurs, can join together with the nitrogen atom to which they are attached to form a $C_3$-$C_8$ heterocycloalkyl ring),

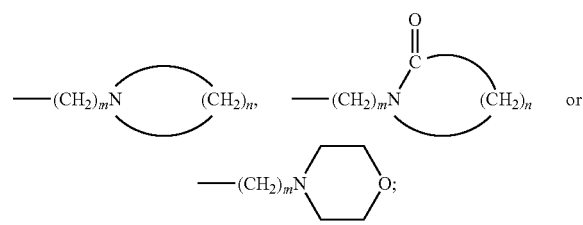

each n is independently 2 to 5;
each m is independently 0 to 6;
$A^1$, $A^2$ and $A^3$ are each independently CR or N;
$A^5$ is CR, N, or NR;
$A^4$ and $A^6$ are each independently C or N, provided that no more than three of $A^1$, $A^2$, $A^3$, $A^4$, $A^5$ and $A^6$ are N or NR; and
each R is independently halogen, hydrogen, cyano, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, —$OC_1$-$C_8$ alkyl, —O(substituted $C_1$-$C_8$ alkyl); $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl; and B) a pharmaceutically acceptable excipient.

The invention also provides methods of treating melanoma, ovarian cancer, cervical cancer, breast cancer, colon cancer, rectal cancer, endometrial cancer, pancreatic cancer, lung cancer, stomach cancer, glioblastoma, liver cancer, prostate cancer, acute lyelogeous leukemia, chronic lyelogenous leukemia, or thyroid cancer, the method comprising administering to a patient in need thereof a therapeutically effective amount of a compound of Formula I

or a pharmaceutically acceptable salt thereof, wherein
Q is —$NR^1R^1$, —$NR^1C(=O)R^1$, —$S(=O)_2NR^1R^1$, —$S(=O)_2R^1$, —$NR^1[S(=O)_2R^1]$, —$C(=O)NR^1R^1$, —$C(=O)R^1$, —$C(=O)OR^1$, —$NR^1C(=O)NR^1R^1$, —$NR^1C(=O)OR^1$, or —$NR^1S(=O)_2NR^1R^1$ (where $R^1R^1$ of $NR^1R^1$, where it occurs, can join together with the nitrogen atom to which they are attached to form a $C_3$-$C_8$ heterocycloalkyl ring);

each $R^1$ is independently hydrogen, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl;

L is

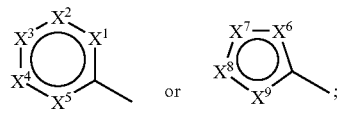

$X^1$, $X^2$, $X^3$, $X^4$ and $X^5$ are each independently CR, $CR^2$ or N, provided that no more than three of $X^1$, $X^2$, $X^3$, $X^4$ and $X^5$ are N and one of $X^1$, $X^2$, $X^3$, $X^4$ and $X^5$ is $CR^2$;

$X^6$, $X^7$, $X^8$ and $X^9$ are each independently CR, $CR^2$, N, O or S, provided that no more than three of $X^6$, $X^7$, $X^8$ and $X^9$ are N, O or S and one of $X^6$, $X^7$, $X^8$ and $X^9$ is $CR^2$;

each $R^2$ is independently halogen, —$SR^1$, —$OR^1$—$S(=O)_2R^1$, —$NR^1[S(=O)_2R^1]$, or —$NR^1S(=O)_2NR^1R^1$ (where $R^1R^1$ of $NR^1R^1$, where it occurs, can join together with the nitrogen atom to which they are attached to form a $C_3$-$C_8$ heterocycloalkyl ring),

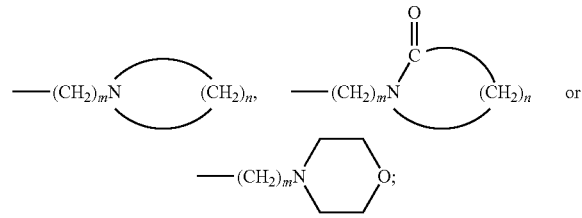

each n is independently 2 to 5;
each m is independently 0 to 6;
$A^1$, $A^2$ and $A^3$ are each independently CR or N;
$A^5$ is CR, N, or NR;
$A^4$ and $A^6$ are each independently C or N, provided that no more than three of $A^1$, $A^2$, $A^3$, $A^4$, $A^5$ and $A^6$ are N or NR; and
each R is independently halogen, hydrogen, cyano, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, —$OC_1$-$C_8$ alkyl, —O(substituted $C_1$-$C_8$ alkyl); $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl.

In one embodiment of the methods, the compound of Formula I is:

N-(6-(6-chloro-5-(methylsulfonamido)pyridine-3-yl)imidazo[1,2-b]pyridazin-2-yl)acetamide;

N-(6-(5,6-dimethoxypyridin-3-yl)imidazo[1,2-b]pyridazin-2-yl)acetamide;

N-(6-(6-chloro-5-(methylsulfonamido)pyridine-3-yl)-3-iodoimidazo[1,2-b]pyridazin-2-yl)acetamide;

N-(6-(6-chloro-5-(methylsulfonamido)pyridine-3-yl)-3-(3-fluorophenyl)imidazo[1,2-b]pyridazin-2-yl)acetamide;

N-(5-(2-amino-3-(3-fluorophenyl)imidazo[1,2-b]pyridazin-6-yl)-2-chloropyridin-3-yl)methanesulfonamide;
N-(6-(6-chloro-5-(methylsulfonamido)pyridine-3-yl)-3-(4-fluoro-3-(morpholine-4-carbonyl)phenyl)imidazo[1,2-b]pyridazin-2-yl)acetamide;
5-(2-amino-6-(6-chloro-5-(methylsulfonamido)pyridine-3-yl)imidazo[1,2-b]pyridazin-3-yl)-2-fluorobenzoic acid;
N-(6-(6-chloro-5-(methylsulfonamido)pyridine-3-yl)-3-(pyridine-4-yl)imidazo[1,2-b]pyridazin-2-yl)acetamide;
N-(5-(2-amino-3-(pyridine-4-yl)imidazo[1,2-b]pyridazin-6-yl)-2-chloropyridin-3-yl)methanesulfonamide;
N-(6-(6-chloro-5-(4-fluorophenylsulfonamido)pyridine-3-yl)imidazo[1,2-a]pyridine-2-yl)acetamide;
N-(5-(2-aminoimidazo[1,2-a]pyridine-6-yl)-2-chloropyridin-3-yl)-4-fluorobenzenesulfonamide;
N-(5-(6-chloro-5-(4-fluorophenylsulfonamido)pyridine-3-yl)-1H-benzo[d]imidazol-2-yl)acetamide;
N-(5-(2-amino-1-(pyridine-2-yl)-1H-benzo[d]imidazol-6-yl)-2-chloropyridin-3-yl)-4-fluorobenzenesulfonamide;
N-(6-(6-chloro-5-(4-fluorophenylsulfonamido)pyridine-3-yl)-1-(pyridine-2-yl)-1H-benzo[d]imidazol-2-yl)acetamide;
N-(6-(6-chloro-5-(3-(difluoromethoxy)phenylsulfonamido)pyridin-3-yl)imidazo[1,2-b]pyridazin-2-yl)acetamide;
N-(6-(6-chloro-5-(2-chloro-6-methylphenylsulfonamido)pyridin-3-yl)imidazo[1,2-b]pyridazin-2-yl)acetamide;
N-(6-(6-chloro-5-(4-(2-hydroxypropan-2-yl)phenylsulfonamido)pyridin-3-yl)imidazo[1,2-b]pyridazin-2-yl)acetamide;
N-(5-(2-aminoimidazo[1,2-b]pyridazin-6-yl)-2-chloropyridin-3-yl)-4-fluorobenzenesulfonamide;
N-(6-(6-chloro-5-(4-(1-(methylamino)ethyl)phenylsulfonamido)pyridine-3-yl)imidazo[1,2-b]pyridazin-2-yl)acetamide (mixture of isomers);
N-(6-(6-chloro-5-(4-(1-(methylamino)ethyl)phenylsulfonamido)pyridine-3-yl)imidazo[1,2-b]pyridazin-2-yl)acetamide (Enantiomer 1);
N-(6-(6-chloro-5-(4-(1-(methylamino)ethyl)phenylsulfonamido)pyridine-3-yl)imidazo[1,2-b]pyridazin-2-yl)acetamide (Enantiomer 2);
N-(6-(6-chloro-5-(2-chloro-4-fluorophenylsulfonamido)pyridin-3-yl)imidazo[1,2-b]pyridazin-2-yl)acetamide;
N-(6-(6-chloro-5-(morpholine-4-sulfonamido)pyridin-3-yl)imidazo[1,2-b]pyridazin-2-yl)acetamide;
N-(6-(6-chloro-5-(4-methylphenylsulfonamido)pyridin-3-yl)imidazo[1,2-b]pyriadazin-2-yl)acetamide;
N-(6-(3,4-dimethoxyphenyl)imidazo[1,2-b]pyridazin-2-yl)acetamide;
N-(6-(6-chloro-5-(3-(difluoromethoxy)phenylsulfonamido)pyridine-3-yl)-3-(pyridine-4-yl)imidazo[1,2-b]pyridazin-2-yl)acetamide;
N-(5-(2-amino-3-(pyridine-4-yl)imidazo[1,2-b]pyridazin-6-yl)-2-chloropyridin-3-yl)-3-(difluoromethoxy)benzenesulfonamide;
N-(6-(6-chloro-5-(3-(difluoromethoxy)phenylsulfonamido)pyridine-3-yl)-3-(2-methylpyridin-4-yl)imidazo[1,2-b]pyridazin-2-yl)acetamide;
N-(5-(2-amino-3-(2-methylpyridin-4-yl)imidazo[1,2-b]pyridazin-6-yl)-2-chloropyridin-3-yl)-3-(difluoromethoxy)benzenesulfonamide;
N-(6-(6-chloro-5-(4-fluorophenylsulfonamido)pyridine-3-yl)-3-(pyridine-4-yl)imidazo[1,2-b]pyridazin-2-yl)acetamide;
N-(6-(6-chloro-5-(3-(difluoromethoxy)phenylsulfonamido)pyridine-3-yl)-3-(pyridine-3-yl)imidazo[1,2-b]pyridazin-2-yl)acetamide;
N-(5-(2-amino-3-(pyridine-3-yl)imidazo[1,2-b]pyridazin-6-yl)-2-chloropyridin-3-yl)-3-(difluoromethoxy)benzenesulfonamide;
N-(5-(2-amino-3-(1,2,3,6-tetrahydropyridin-4-yl)imidazo[1,2-b]pyridazin-6-yl)-2-chloropyridin-3-yl)-3-(difluoromethoxy)benzenesulfonamide;
N-(6-(6-chloro-5-(4-fluorophenylsulfonamido)pyridazin-3-yl)imidazo[1,2-b]pyridazin-2-yl)acetamide; or
N-(6-(2-chloropyrimidin-4-yl)H-imidazo[1,2-a]pyridin-2-yl)acetamide, or a pharmaceutically acceptable salt thereof.

In another embodiment of the methods, an additional pharmaceutically active compound is administered to the patient, which compound is selected from the group consisting of antineoplastic agents; anti-angiogenic agents; chemotherapeutic agents and peptidal cancer therapy agents.

In a further embodiment of the methods, the additional pharmaceutically active compound is an antineoplastic agent and the antineoplastic agent is selected from the group consisting of antibiotic-type agents; alkylating agents; antimetabolite agents; hormonal agents; immunological agents; interferon-type agents; and kinase inhibitors.

In another embodiment of the compounds of Formula I, or the pharmaceutically acceptable salts thereof, either alone or in combination with any of the above or below embodiments, $A^1$, $A^2$ and $A^3$ are CR; $A^4$ and $A^6$ are C; and $A^5$ is NR.

In another embodiment of the compounds of Formula I, or the pharmaceutically acceptable salts thereof, either alone or in combination with any of the above or below embodiments Q is —$NR^1C(=O)R^1$.

DETAILED DESCRIPTION OF THE INVENTION

The present invention relates to compounds of Formula I

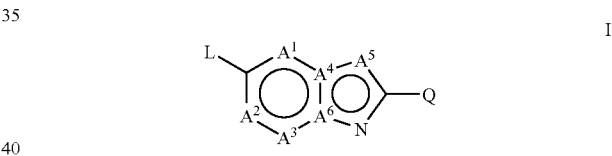

or a pharmaceutically acceptable salt thereof, wherein
Q is —$NR^1R^1$, —$NR^1C(=O)R^1$, —$S(=O)_2NR^1R^1$, —$S(=O)_2R^1$, —$NR^1[S(=O)_2R^1]$, —$C(=O)NR^1R^1$, —$C(=O)R^1$, —$C(=O)OR^1$, —$NR^1C(=O)NR^1R^1$, —$NR^1C(=O)OR^1$, or —$NR^1S(=O)_2NR^1R^1$ (where $R^1R^1$ of $NR^1R^1$, where it occurs, can join together with the nitrogen atom to which they are attached to form a $C_3$-$C_8$ heterocycloalkyl ring);

each $R^1$ is independently hydrogen, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl;

L is

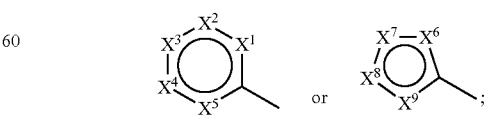

$X^1$, $X^2$, $X^3$, $X^4$ and $X^5$ are each independently CR, $CR^2$ or N, provided that no more than three of $X^1$, $X^2$, $X^3$, $X^4$ and $X^5$ are N and one of $X^1$, $X^2$, $X^3$, $X^4$ and $X^5$ is $CR^2$;

$X^6$, $X^7$, $X^8$ and $X^9$ are each independently CR, $CR^2$, N, O or S, provided that no more than three of $X^6$, $X^7$, $X^8$ and $X^9$ are N, O or S and one of $X^6$, $X^7$, $X^8$ and $X^9$ is $CR^2$;

each $R^2$ is independently halogen, —$SR^1$, —$OR^1$ —S(=O)$_2R^1$, —$NR^1[S(=O)_2R^1]$, —$NR^1S(=O)_2NR^1R^1$ (where $R^1R^1$ of $NR^1R^1$, where it occurs, can join together with the nitrogen atom to which they are attached to form a $C_3$-$C_8$ heterocycloalkyl ring),

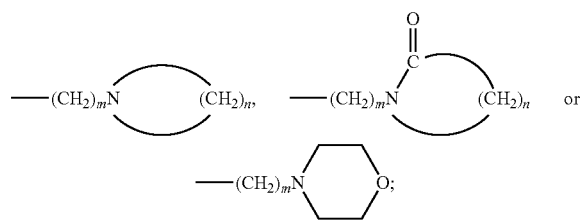

each n is independently 2 to 5;
each m is independently 0 to 6;
$A^1$, $A^2$ and $A^3$ are each independently CR or N;
$A^5$ is CR, N, or NR;
$A^4$ and $A^6$ are each independently C or N, provided that no more than three of $A^1$, $A^2$, $A^3$, $A^4$, $A^5$ and $A^6$ are N or NR; and each R is independently halogen, hydrogen, cyano, $C_1$-$C_8$ alkyl, substituted $C_1$-$C_8$ alkyl, $C_2$-$C_8$ alkenyl, substituted $C_2$-$C_8$ alkenyl, $C_2$-$C_8$ alkynyl, substituted $C_2$-$C_8$ alkynyl, —O$C_1$-$C_8$ alkyl, —O(substituted $C_1$-$C_8$ alkyl); $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_1$-$C_8$ alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_1$-$C_8$alkoxy.

The term "halogen" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_2$-$C_8$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_2$-$C_8$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_3$-$C_8$ cycloalkyl groups.

The term "perfluoroalkyl" means an alkyl group in which all of the hydrogen atoms have been replaced with fluorine atoms. Common perfluoroalkyl groups are $C_1$-$C_8$perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 3 heteroatoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom selected from the following: halogen, $C_1$-$C_8$alkyl, hydroxyl, $C_1$-$C_8$alkoxy, —$NR^xR^x$, nitro, cyano, halo or perhalo$C_1$-$C_8$alkyl, $C_2$-$C_8$alkenyl, $C_2$-$C_8$alkynyl, —$SR^x$, —$SO_2R^x$, —$C(=O)OR^x$, —$C(=O)R^x$, wherein each $R^x$ is independently hydrogen, $C_1$-$C_8$ alkyl, or heterocycloalkyl. It is noted that when the substituent is —$NR^xR^x$, the $R^x$ groups may be joined together with the nitrogen atom to form a ring. Moreover, the substituents may also be substituted. For example, a $C_1$-$C_8$alkyl group may be substituted with a hydroxyl group or an amine. Likewise, an alkoxy group may be substituted with a halogen. Any group or molecule that may be substituted can have one or more substituents that can be the same or different.

A group or atom that replaces a hydrogen atom is also called a substituent. Any particular molecule or group can have one or more substituent depending on the number of hydrogen atoms that can be replaced.

The symbol "-" represents a covalent bond and can also be used in a group to indicate the point of attachment of a radical to another group. It is also common in organic chemistry to use this symbol to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula I, a salt of a compound of Formula I, a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active agents, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic add functional group, a prodrug can comprise an ester formed by the replacement of the hydrogen atom of the add group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water, ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the imidazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^{18}$F, and $^{36}$Cl.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

The compounds of the present invention are useful for the treatment of PI3K mediated diseases and disorders including melanomas, carcinomas, and other cancers. In one embodiment of the invention, there is provided a method of modulating a PI3K enzyme in a patient, the method comprising administering to a patient in need thereof a therapeutically effective amount of a compound of Formula I or a pharmaceutically acceptable salt thereof. The present invention also concerns the use of a compound of Formula I for the manufacture of a medicament for the treatment of a PI3K mediated disease such as cancer.

The term "patient in need thereof" means a patient who has or is at risk of having a PI3K mediated disease or condition.

The term "cancer" means a physiological condition in mammals that is characterized by unregulated cell growth. General classes of cancers include carcinomas, lymphomas, sarcomas, and blastomas.

The compounds of the present invention can be used to treat cancer. The methods of treating a cancer comprise administering to a patient in need thereof a therapeutically effective amount of a compound of Formula I or a pharmaceutically acceptable salt thereof.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, chronic lyelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with a compound of the present invention include endometrial cancer, head and neck cancer, glioblastoma, malignant ascites, and hematopoietic cancers.

The compounds of the present invention cal also be used to treat hyperproliferative disorders such as thyroid hyperplasia (especially Grave's disease), and cysts (such as hypervascularity of ovarian stroma, characteristic of polycystic ovarian syndrome (Stein-Leventhal syndrome)).

The compounds of Formula I may also be administered in combination with one or more additional pharmaceutically active compounds/agents. In a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; paclitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Additional pharmaceutically active agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

The compounds of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, the compounds of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflomithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofuran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SD01 (Amgen); galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar. It is noted that the agents recited above may also be administered as pharmaceutically acceptable salts when appropriate.

The compounds of the present invention may also be used in combination with radiation therapy, hormone therapy, surgery and immunotherapy, which therapies are well know to those skilled in the art.

The compounds of the present invention can be used in the manufacture of a medicament for the treatment of the diseases or conditions receited herein.

All patents and other publications recited herein are hereby incorporated by reference.

This application, including the claims, contains listings of species and groups using the language like "selected from . . . and . . . " and "is . . . or . . . " (sometimes referred to as a Markush group). When this language is used in this application, it is meant to include the group as a whole, any single member thereof, or any subgroup thereof. The use of this language is for brevity and is not meant in any way to limit the deletion of single members or subgroups.

EXAMPLES

The examples presented below illustrate specific embodiments of the present invention. These examples are meant to be representative and are not intended to limit the scope of the claims in any manner.

Analytical Methods:

Unless otherwise indicated, HPLC analyses were run on an Agilent Model 1100 system with an Agilent Technologies Zorbax SB-$C_8$ (5μ) reverse phase column (4.6×150 mm) run at 30° C. with a flow rate of about 1.50 mL/min (Agilent Technologies, Santa Clara, Calif.). The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush). It is noted that all percents (%) used herein are by volume with respect to the total volume. Alternatively, still using the Agilent Model 1100 system, a Synergy MAX-RP, 5 m, 50×2.0 mm column with the same solvent system, a flow rate of 0.8 ml/min, and a gradient of 10% to 100% B for the first two minutes, then 100% B for 1.8 minutes, and then a return to 10% B over 0.2 minutes can be used.

LC-MS Methods:

Samples were run on an Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (ACN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Methods:

Where indicated, compounds of the present invention were purified via reverse phase HPLC using a Gilson workstation (Gilson, Middleton, Wis.) utilizing one of the following two columns and methods: (A) Using a 50×100 mm column (Waters, Exterra, C18, 5μ) (Waters, Milford, Mass.) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a 10 min gradient from 40% to 100% solvent B followed by a 5 min flow of 100% solvent B. The gradient was followed by a 2 min return to 40% solvent B. (B) Using a 20×50 mm column at 20 mL/min. The mobile phase used was a mixture of solvent A ($H_2O$/0.1% TFA) and solvent B (ACN/0.1% TFA) with a 10 min gradient from 5% to 100% solvent B. The gradient is followed by a 2 min return to 5% ACN.

Proton NMR Spectra:

Unless otherwise indicated, all $^1H$ NMR spectra were run on a Varian (Varian, Palo Alto, Calif.) series Mercury 300 MHz instrument or a Bruker (Bruker, Bilerica, Mass.) series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method. Compounds having an isotopic atom, such as bromine and the like, are reported according to the detected isotopic pattern, as appreciated by those skilled in the art.

The following abbreviations are used:
ACN acetonitrile
TFA trifluoroacetic acid
TFAA trifluoroacetic anhydride
Ts tosyl
DTT dithiothreitol
ATP adenosine 5'-triphosphate
PIP2 phosphatidylinositol bisphosphate
FBS fetal bovine serum
Ac$_2$O acetic anhydride
DMAP dimethyl aminopyridine
rt or RT room temperature
LCMS or LC-MS liquid chromatography mass spectroscopy
NMR nuclear magnetic resonance
aq aqueous
py or pyr pyridine
TsCl para-toluene sulfonyl chloride
MS mass spectra
ESI electrospray ionization
m/z mass divided by charge
TS toluene sulfonyl
iPr$_2$NEt N-ethyl diisopropylamine
HPLC high pressure liquid chromatography
TMS tetramethylsilane
iPrOH isopropyl alcohol
PG protecting group
DCM dichloromethane
DMSO dimethyl sulfoxide
DMF N,N-dimethylformamide
THF tetrahydrofuran
Et$_2$O diethyl ether
EtOAc ethyl acetate
MeOH methyl alcohol
EtOH ethyl alcohol
MeCN acetonitrile
MeI iodomethane
NMP 1-methyl-2-pyrrolidinone
DCM dichloromethane
TFA trifluoroacetic acid
Sat. saturated
h hour
min minutes
mL milliliters
g grams
mg milligrams
HOAc acetic acid
conc concentrated
DIEA N,N-Diisopropylethylamine
TEA Triethylamine
ee enantiomeric excess
DME Dimethyl ether
MPLC Medium pressure liquid chromatography General Synthetic Scheme

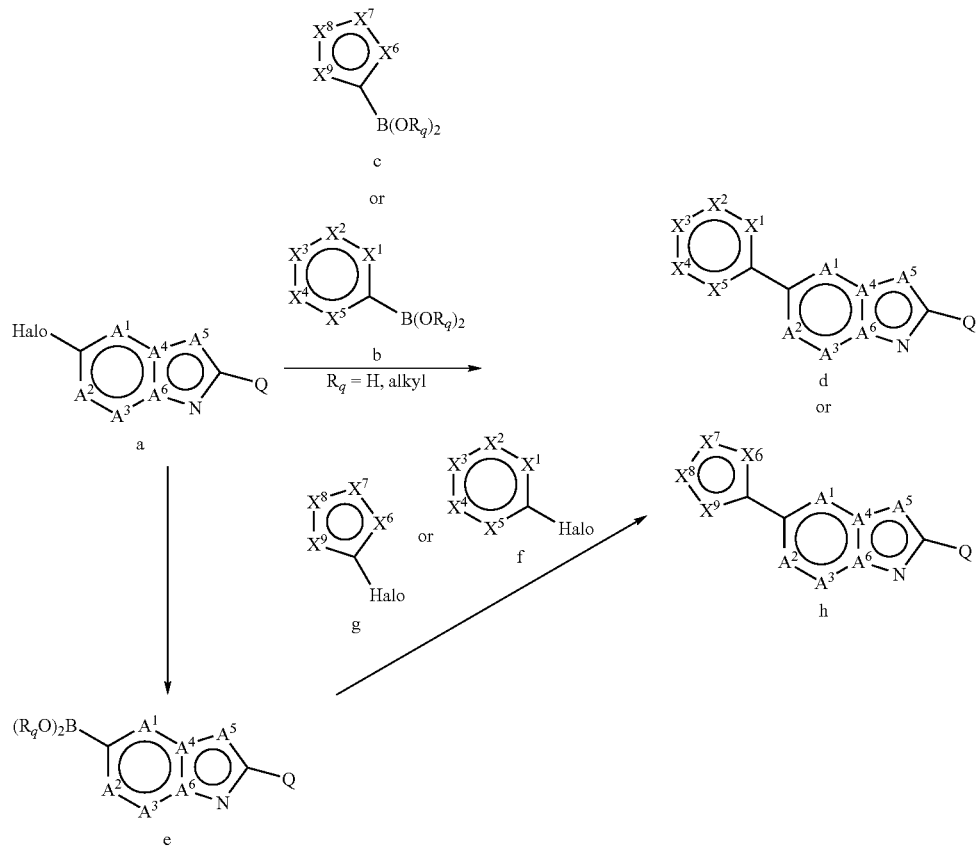

Scheme A

In general the compounds of the present invention can be made in accordance with Scheme A above. For example, a compound of Formula a or e can be coupled with an appropriate group b, c, g or f to form compounds d and h using the Suzuki Coupling procedure. The Suzuki Coupling and variations thereof are well known to those skilled in the art. It is noted that the variables used in Scheme A are as defined herein.

Imidazopyridazines—Exemplary Syntheses

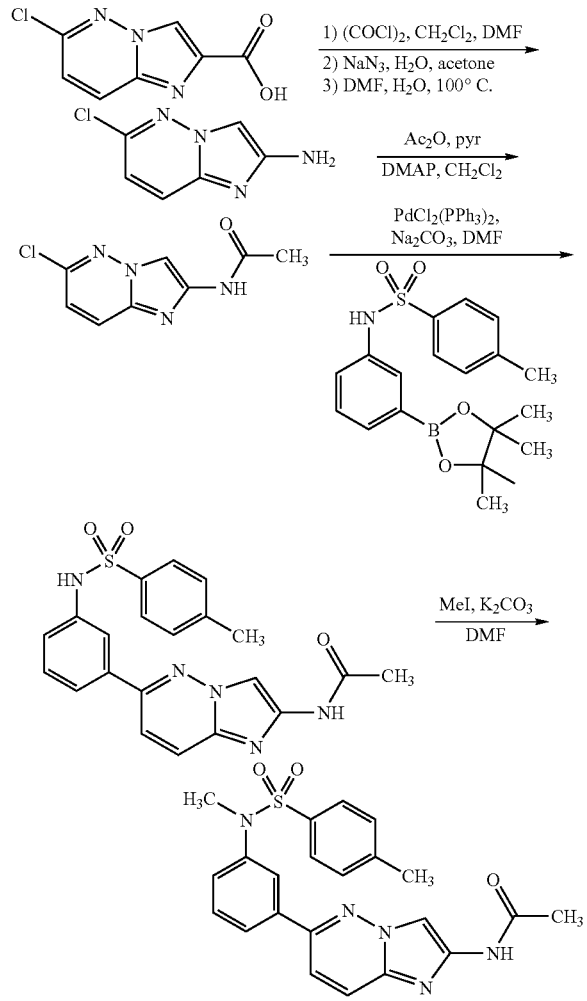

Example 1

N-(6-(3-(4-Methylphenylsulfonamido)phenyl)imidazo[1,2-b]pyridazin-2-yl)acetamide

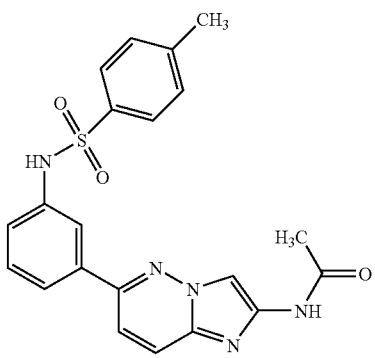

Step 1.
6-Chloroimidazo[1,2-b]pyridazine-2-carbonyl chloride

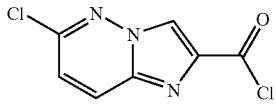

To a 250-mL, round-bottomed flask was added 6-chloroimidazo[1,2-b]pyridazine-2-carboxylic acid (2.0 g, 10 mmol, Maybridge, Cornwall, UK) and $CH_2Cl_2$ (40 mL). To the mixture was added oxalyl chloride (20 mL, 40 mmol, 2 M in $CH_2Cl_2$) and DMF (8.0 μL, 0.10 mmol). The mixture was stirred for 1.5 h at 25° C. Toluene (10 mL) was added and the mixture was concentrated to afford the title compound which was taken on to the next step without further purification.

Step 2. Azido(6-chloroimidazo[1,2-b]pyridazin-2-yl)methanone

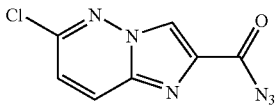

To a solution of 6-chloroimidazo[1,2-b]pyridazine-2-carbonyl chloride from Step 1 (2.2 g, 10 mmol) in acetone (40 mL) was added sodium azide (0.43 g, 6.6 mmol, solution in 1.5 mL $H_2O$). The mixture was stirred at 25° C. for 1 h then poured into aq. $NaHCO_3$. The solid precipitate was collected by careful filtration. The filtercake was not allowed to go dry (solvent-free). The filtercake was washed with benzene (2×50 mL) and then transferred to a 150-mL, round-bottomed flask. To azeotropically remove residual water, the solid was suspended in benzene (75 mL) and then concentrated to one-third its volume. Then once again the material was suspended in benzene (75 mL) and concentrated to near dryness to provide the title compound, which was taken on to the next step without further purification.

Step 3. 6-Chloroimidazo[1,2-b]pyridazin-2-amine

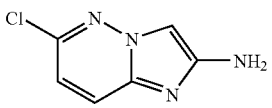

To a 100-mL, round-bottomed flask was added azido(6-chloroimidazo[1,2-b]pyridazin-2-yl)methanone from Step 2 (2.3 g, 10 mmol) and DMF (40 mL). The solution was heated to 100° C. and $H_2O$ (1.8 mL, 100 mmol) was added. The mixture was stirred for 45 min and then allowed to cool to room temperature. The mixture was poured into water (150 mL) and then concentrated in vacuo. The solid residue was dissolved in 1:2 MeOH/$CH_2Cl_2$ (900 mL) and concentrated onto silica. Purification by silica gel chromatography (1 to 5% MeOH (2 M in $NH_3$)/$CH_2Cl_2$) afforded the title compound as a yellow-green solid (0.71 g, 42% yield). MS (ESI positive ion) m/z: 169 (M+1). ¹H NMR (400 MHz, DMSO-d₆): δ ppm 7.69 (d, J=9.2 Hz, 1H), 7.37 (s, 1H), 7.05 (d, J=9.2 Hz, 1H), 5.74 (broad s, 2H).

Step 4.
N-(6-Chloroimidazo[1,2-b]pyridazin-2-yl)acetamide

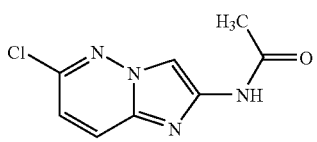

To a 250-mL, round-bottomed flask was added 6-chloroimidazo[1,2-b]pyridazin-2-amine from Step 3 (0.67 g, 4.0 mmol), CH₂Cl₂ (60 mL), acetic anhydride (0.45 mL, 4.8 mmol), pyridine (0.49 mL, 6.0 mmol), and 4-(dimethylamino)pyridine (4.9 mg, 0.040 mmol). The mixture was stirred at 25° C. for 24 h. The reaction mixture was concentrated and then diluted with aq. NaHCO₃ and extracted with 25% iPrOH/CHCl₃ (3×100 mL). The combined extracts were washed with brine (100 mL), dried (Na₂SO₄) and concentrated onto silica. Purification by silica gel chromatography (0 to 4% MeOH (2 M in NH₃)/CH₂Cl₂) afforded the title compound as a yellow solid (0.62 g, 74%). MS (ESI positive ion) m/z: 211 (M+1). ¹H NMR (400 MHz, DMSO-d₆) δ ppm 2.10 (s, 3H), 7.33 (d, J=9.4 Hz, 1H), 8.06 (d, J=9.4 Hz, 1H), 8.26 (s, 1H), 10.95 (s, 1H).

Alternatively, (6-chloroimidazo[1,2-b]pyridazin-2-yl)acetamide can be made as follows:

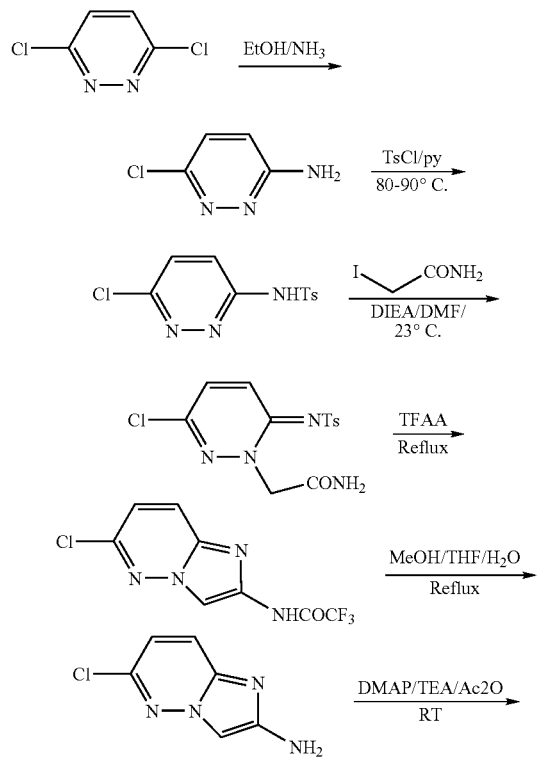

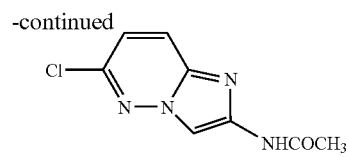

Step A. 6-Chloro-pyridazin-3-ylamine

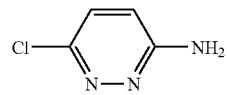

3,6-Dichloropyridazine (85 g, 0.57 mol, Aldrich, St. Louis, Mo.) was taken up in 750 mL ethanolic ammonia and stirred at 125° C. in a closed vessel for 8 h. The solvent was evaporated and the residue was recrystallized from ethyl acetate to afford the title compound (56 g, 75%). ¹H NMR (DMSO-d₆, 300 MHz): δ 6.65 (s, 1H), 6.88 (d, 1H), 7.35 (d, 2H).

Step B. N-(6-chloropyridazin-3-yl)-4-methylbenzenesulfonamide

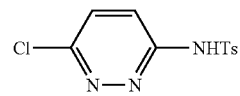

6-Chloro-pyridazin-3-ylamine (7 g, 54 mmol) was taken up in pyridine (54 mL) and TsCl (11.34 g, 59 mmol) was added. The solution was heated at 80-90° C. for 24 h. The solution was concentrated and the residue was diluted with water and extracted with ethyl acetate. The organic layer was washed with brine (2×50 mL), dried over sodium sulfate and concentrated. Purification by silica gel chromatography (ethyl acetate/hexane) afforded the title compound (4 g, 26%). ¹H NMR (DMSO-d₆, 300 MHz): δ 2.4 (s, 3H), 7.4 (d, 3H), 7.54 (d, 1H), 7.8 (m, 3H), 12.5 (br, 1H)

Step C. 2-(3-chloro-6-(tosylimino)pyridazin-1(6H)-yl)acetamide

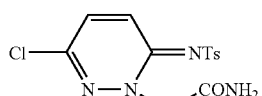

N,N-Diisopropylethylamine (10.4 mL, 81 mmol) was added to a suspension of N-(6-chloropyridazin-3-yl)-4-methylbenzenesulfonamide (21 g, 74 mmol) in dry DMF (100 mL) under argon. To the resulting solution was added 2-iodoacetamide (15 g, 81 mmol, Aldrich, St. Louis, Mo.) and the mixture was stirred for 24 h at rt. The reaction mixture was diluted with water and precipitated solid was filtered off to afford the title compound (17 g, 68%). ¹H NMR (DMSO-d₆, 300 MHz): δ 2.4 (s, 3H), 4.8 (s, 2H), 7.3 (d, 2H), 7.6-7.8 (m, 4H), 7.95 (d, 1H).

Step D. N-(6-chloroimidazo[1,2-b]pyridazin-2-yl)-2,2,2-trifluoroacetamide

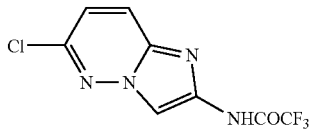

To a solution of 2-(3-chloro-6-(tosylimino)pyridazin-1(6H)-yl)acetamide (80 mg, 0.23 mmol) in 5 mL dry DCM was added TFAA (0.8 mL) and the solution was refluxed for 3 h. The solution was concentrated and the residue was taken up in ethyl acetate and washed with sat. sodium bicarbonate. The organic layer was dried over sodium sulfate and concentrated to afford the title compound (60 mg, 61%). $^1$H NMR (CDCl$_3$, 300 MHz): δ 7.18 (d, 1H), 7.8 (d, 1H), 8.5 (s, 1H), 10.4 (br, 1H).

Step E. 6-chloroimidazo[1,2-b]pyridazin-2-amine

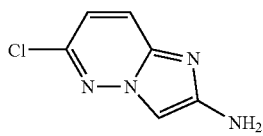

To a solution of N-(6-chloroimidazo[1,2-b]pyridazin-2-yl)-2,2,2-trifluoroacetamide (80 mg, 0.30 mmol) in a THF:methanol:water (1 mL each) mixture was added anhydrous potassium carbonate (400 mg, 3 mmol). The reaction mixture was refluxed for 8 hrs. After cooling to rt, the reaction mixture diluted with ethyl acetate and water. The phases were separated and the organic layer was washed with brine (2×5 mL), dried over sodium sulfate and concentrated to afford the title compound (45 mg, 90%). $^1$H NMR (DMSO-d$_6$, 300 MHz): δ 5.65 (s, 2H), 7.02 (d, 1H), 7.7 (d, 1H).

Step F. N-(6-Chloro-imidazo[1,2-b]pyridazin-2-yl)-acetamide

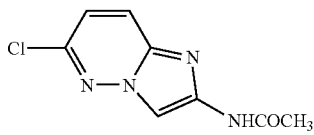

To a solution of 6-chloroimidazo[1,2-b]pyridazin-2-amine (18 g, 106.5 mmol) in DCM (180 mL) was added triethylamine (10.8 g, 106.5 mmol), DMAP (1.32 g, 1.06 mmol), and acetic anhydride (6 g, 106.5 mmol) sequentially at rt. The reaction mixture was stirred for 5 h at rt and the precipitate was filtered and washed with 50 mL of methanol to afford the title compound (15 g, 66%). $^1$H NMR (DMSO-d$_6$, 300 MHz): δ 7.3 (d, 1H), 8.02 (d, 1H), 8.25 (s, 1H). LCMS (M+1) 211 (99%).

Step 5. N-(6-(3-(4-Methylphenylsulfonamido)phenyl)imidazo[1,2-b]pyridazin-2-yl)acetamide

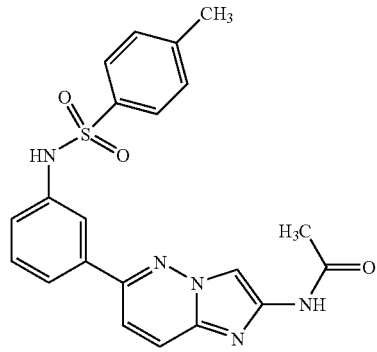

To a 10-mL, round-bottomed flask was added N-(6-chloroimidazo[1,2-b]pyridazin-2-yl)acetamide from Step 4 (0.060 g, 0.28 mmol), 4-methyl-N-(3-(4,4,5,5-tetramethyl-1,3,2-dioxaborolan-2-yl)phenyl)benzenesulfonamide (0.19 g, 0.51 mmol, Aldrich, St. Louis, Mo.), DMF (3.0 mL), and aq. sodium carbonate (0.85 mL, 1.7 mmol, 2 M). The mixture was carefully evacuated and backfilled with N$_2$. Bis(triphenylphosphine)palladium(II) chloride (20 mg, 0.028 mmol, Strem Chemical, Inc., Newburyport, Mass.) was added. Once again, the mixture was carefully evacuated and backfilled with N$_2$. The mixture was stirred at 100° C. for 2 h and then allowed to cool to room temperature. The mixture was poured into water (75 mL) and extracted with EtOAc (3×75 mL). The combined extracts were washed with water (2×50 mL) and brine (50 mL) then dried (Na$_2$SO$_4$) and concentrated onto silica. Purification by silica gel chromatography (1 to 5% MeOH (2 M in NH$_3$)/CH$_2$Cl$_2$) afforded the title compound as an off-white solid. MS (ESI positive ion) m/z: 422 (M+1). $^1$H NMR (400 MHz, DMSO-d$_6$): δ ppm 10.92 (s, 1H), 10.44 (s, 1H), 8.26 (s, 1H), 8.05 (d, J=9.6 Hz, 1H), 7.77 (t, J=1.8 Hz, 1H), 7.67-7.71 (m, 3H), 7.61 (d, J=9.6 Hz, 1H), 7.40 (t, J=7.9 Hz, 1H), 7.35 (d, J=8.0 Hz, 2H), 7.19 (dd, J=8.0 Hz, 1.4 Hz, 1H), 2.32 (s, 3H), 2.11 (s, 3H).

Example 2

N-(6-(3-(N,4-Dimethylphenylsulfonamido)phenyl)imidazo[1,2-b]pyridazin-2-yl)acetamide

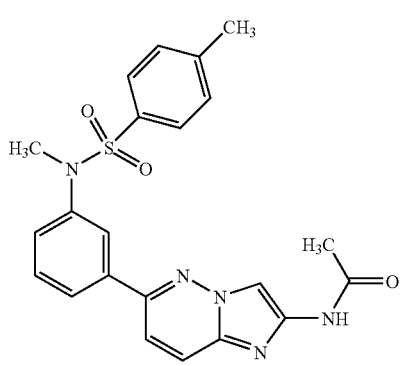

To a round-bottomed flask was added N-(6-(3-(4-methylphenylsulfonamido)phenyl)imidazo[1,2-b]pyridazin-2-yl)acetamide (from Example 1, Step 5) (0.027 g, 0.064 mmol), potassium carbonate (0.013 g, 0.096 mmol), DMF (1.0 mL) and iodomethane (0.0044 mL, 0.071 mmol). The mixture was stirred at 25° C. for 14 h, then poured into water and extracted with EtOAc (3×30 mL). The combined extracts were washed with water (2×50 mL) and brine (50 mL) then dried (Na$_2$SO$_4$) and concentrated onto silica. Purification by silica gel chromatography (0 to 3% MeOH (2 M in NH$_3$)/CH$_2$Cl$_2$) afforded the title compound as a light-yellow solid. MS (ESI positive ion) m/z: 436 (M+1). $^1$H NMR (400 MHz, DMSO-d$_6$): δ ppm 10.92 (s, 1H), 8.27 (s, 1H), 8.07 (d, J=9.6 Hz, 1H), 7.97 (d, J=8.4 Hz, 1H), 7.75 (t, J=1.9 Hz, 1H), 7.70 (d, J=9.6 Hz, 1H), 7.52 (t, J=7.9 Hz, 1H), 7.39-7.47 (m, 4H), 7.23 (dd, J=8.0 Hz, 1.4 Hz, 1H), 3.20 (s, 3H), 2.41 (s, 3H), 2.12 (s, 3H).

Example 3

N-(6-(2-Fluoropyridin-4-yl)imidazo[1,2-b]pyridazin-2-yl)acetamide

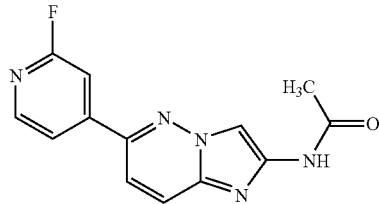

Following the procedure described for N-(6-(3-(4-methylphenylsulfonamido)phenyl)imidazo[1,2-b]pyridazin-2-yl)acetamide (Example 1), N-(6-chloroimidazo[1,2-b]pyridazin-2-yl)acetamide (Example 1, Step 4) (0.040 g, 0.19 mmol) was reacted with 2-fluoropyridin-4-ylboronic acid (0.054 g, 0.38 mmol, Synthonix, Wake Forest, N.C.) to afford the title compound as a yellow solid. MS (ESI positive ion) m/z: 272 (M+1). $^1$H NMR (400 MHz, DMSO-d$_6$): δ pp, 11.00 (s, 1H), 8.43 (d, J=5.3 Hz, 1H), 8.18 (d, J=10.0 Hz, 1H), 8.05 (t, J=1.6 Hz, 0.5H), 8.04 (t, J=1.6 Hz, 0.5H), 7.96 (d, J=9.4 Hz, 1H), 7.86 (s, 1H), 2.13 (s, 3H).

Example 4

N-(6-(2-(2-Fluorophenylthio)pyridin-4-yl)imidazo[1,2-b]pyridazin-2-yl)acetamide

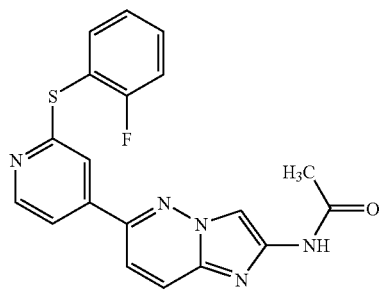

To a 10-mL, round-bottomed flask was added N-(6-(2-fluoropyridin-4-yl)imidazo[1,2-b]pyridazin-2-yl)acetamide (Example 3) (0.034 g, 0.13 mmol), DMF (2.0 mL), 2-fluorothiophenol (0.045 mL, 0.42 mmol, Aldrich, St. Louis, Mo.), and sodium hydride (17 mg, 0.45 mmol, 60% dispersion in mineral oil, Aldrich, St. Louis, Mo.). The mixture was stirred at 110° C. for 42 h. The mixture was poured into water and extracted with EtOAc (3×30 mL). The combined extracts were washed with water (2×30 mL) and brine (30 mL) then dried (Na$_2$SO$_4$), and concentrated onto silica. Purification by silica gel chromatography (0 to 3.5% MeOH (2 M in NH$_3$)/CH$_2$Cl$_2$), followed by further purification by preparative HPLC (Phenomenex Synergi 4μ MAX-RP 150×21.2 mm, 2 to 100% CH$_3$CN/H$_2$O, 0.1% TFA, over 15 min) (Phenomenex, Torrance, Calif.) and conversion to the free base by elution of the isolated material through an SCX cartridge (Radleys Discovery Technologies, Essex, UK) with MeOH (2 M in NH$_3$)/CH$_2$Cl$_2$ afforded the title compound as a yellow solid. MS (ESI positive ion) m/z: 380 (M+1). $^1$H NMR (400 MHz, DMSO-d$_6$): δ ppm 10.99 (s, 1H), 8.53 (d, J=5.0 Hz, 1H), 8.28 (s, 1H), 8.13 (d, J=9.5 Hz, 1H), 7.82-7.84 (m, 3H), 7.71 (t, J=7.3 Hz, 1H), 7.62 (q, J=6.7 Hz, 1H), 7.43 (t, J=8.8 Hz, 1H), 7.35 (t, J=7.5 Hz, 1H), 2.11 (s, 3H).

Example 5

N-(6-(3-Aminophenyl)imidazo[1,2-b]pyridazin-2-yl)acetamide

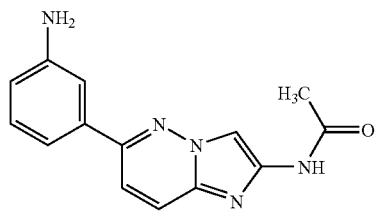

Following the procedure described for compound N-(6-(3-(4-methylphenylsulfonamido)phenyl)imidazo[1,2-b]pyridazin-2-yl)acetamide (Example 1), N-(6-chloroimidazo[1,2-b]pyridazin-2-yl)acetamide (Example 1, Step 4) (0.071 g, 0.34 mmol) was reacted with 3-aminobenzeneboronic acid (0.094 g, 0.60 mmol, Alfa Aesar, Avocado Organics, Ward Hill, Mass.) to afford the title compound as a yellow solid. MS (ESI positive ion) m/z: 268 (M+1). $^1$H NMR (400 MHz, DMSO-d$_6$): δ ppm 10.87 (s, 1H), 8.24 (s, 1H), 8.00 (d, J=9.4 Hz, 1H), 7.62 (d, J=9.4 Hz, 1H), 7.25 (t, J=1.9 Hz, 1H), 7.12-7.19 (m, 2H), 6.69-6.71 (m, 1H), 5.30 (s, 2H), 2.11 (s, 3H).

Example 6

N-(6-(3-(Isoquinoline-5-sulfonamido)phenyl)imidazo[1,2-b]pyridazin-2-yl)acetamide (TFA Salt)

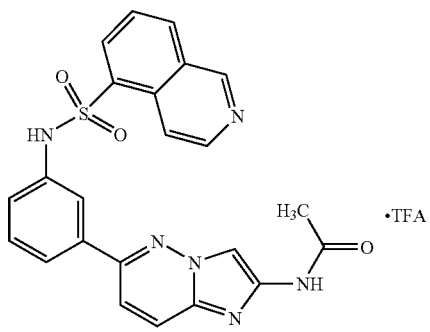

To a 10-mL, round-bottomed flask was added N-(6-(3-aminophenyl)imidazo[1,2-b]pyridazin-2-yl)acetamide (Example 5) (0.032 g, 0.12 mmol), DMF (2.0 mL), pyridine (0.015 mL, 0.180 mmol), and isoquinoline-5-sulfonyl chloride hydrochloride (0.0395 g, 0.150 mmol, Toronto Research Chemicals, Ottawa, Ontario). The mixture was stirred at 25° C. for 5 h then concentrated under reduced pressure. The residue was purified by preparative HPLC (Phenomenex Synergi 4μ MAX-RP 150×21.2 mm, 2 to 100% $CH_3CN/H_2O$, 0.1% TFA, over 15 min) (Phenomenex, Torrance, Calif.) to afford the title compound as a light-yellow solid. MS (ESI positive ion) m/z: 459 (M+1). $^1$H NMR (400 MHz, DMSO-$d_6$): δ ppm 11.03 (s, 1H), 10.91 (s, 1H), 9.50 (s, 1H), 8.75 (d, J=6.5 Hz, 1H), 8.58 (d, J=6.0 Hz, 1H), 8.53 (d, J=7.0 Hz, 1H), 8.45 (d, J=8.0 Hz, 1H), 8.25 (s, 1H), 8.02 (d, J=9.5 Hz, 1H), 7.84 (t, J=7.8 Hz, 1H), 7.71 (s, 1H), 7.62 (d, J=7.5 Hz, 1H), 7.56 (d, J=9.5 Hz, 1H), 7.34 (t, J=7.8 Hz, 1H), 7.16 (d, J=8.0 Hz, 1H), 2.11 (s, 3H).

Example 7

N-(6-(3-(Naphthalene-1-sulfonamido)phenyl)imidazo[1,2-b]pyridazin-2-yl)acetamide (TFA Salt)

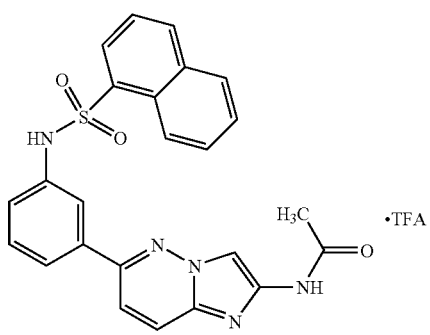

Following the procedure for compound N-(6-(3-(isoquinoline-5-sulfonamido)phenyl)imidazo[1,2-b]pyridazin-2-yl)acetamide (Example 6), N-(6-(3-aminophenyl)imidazo[1,2-b]pyridazin-2-yl)acetamide (Example 5) (0.032 g, 0.12 mmol) was reacted with 1-naphthalenesulfonyl chloride (0.034 g, 0.15 mmol, Aldrich, St. Louis, Mo.) to afford the title compound as a white solid. MS (ESI positive ion) m/z: 458 (M+1). $^1$H NMR (400 MHz, DMSO-$d_6$): δ ppm 10.92 (s, 1H), 10.91 (s, 1H), 8.77 (d, J=8.6 Hz, 1H), 8.30 (d, J=7.4 Hz, 1H), 8.21-8.24 (m, 2H), 8.07 (d, J=8.0 Hz, 1H), 8.02 (d, J=9.4 Hz, 1H), 7.74-7.78 (m, 1H), 7.62-7.70 (m, 3H), 7.58 (d, J=7.8 Hz, 1H), 7.53 (d, J=9.4 Hz, 1H), 7.32 (t, J=7.9 Hz, 1H), 7.16 (dd, J=8.0 Hz, 1.6 Hz, 1H), 2.11 (s, 3H).

Example 8

N-(6-(5-(Methylthio)pyridin-3-yl)imidazo[1,2-b]pyridazin-2-yl)acetamide

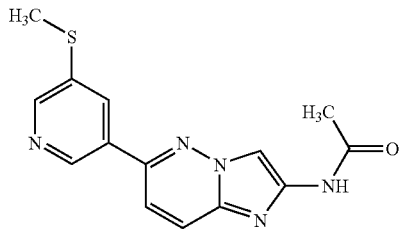

Following the procedure described for N-(6-(3-(4-methylphenylsulfonamido)phenyl)imidazo[1,2-b]pyridazin-2-yl)acetamide (Example 1), N-(6-chloroimidazo[1,2-b]pyridazin-2-yl)acetamide (Example 1, Step 4) (0.075 g, 0.36 mmol) was reacted with 5-(methylthio)pyridin-3-ylboronic acid (0.11 g, 0.64 mmol, Combi-Blocks, San Diego, Calif.) to afford the title compound as a white solid. MS (ESI positive ion) m/z: 300 (M+1). $^1$H NMR (400 MHz, DMSO-$d_6$): δ ppm 10.94 (s, 1H), 9.00 (d, J=2.0 Hz, 1H), 8.60 (d, J=2.2 Hz, 1H), 8.34 (s, 1H), 8.27 (t, J=2.2 Hz, 1H), 8.12 (d, J=9.4 Hz, 1H), 7.90 (d, J=9.4 Hz, 1H), 2.64 (s, 3H), 2.12 (s, 3H).

Example 9

N-(6-(3-(Methylthio)phenyl)imidazo[1,2-b]pyridazin-2-yl)acetamide

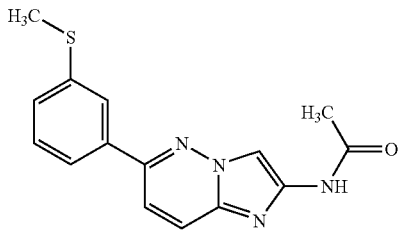

Following the procedure described for compound N-(6-(3-(4-methylphenylsulfonamido)phenyl)imidazo[1,2-b]pyridazin-2-yl)acetamide (Example 1), N-(6-chloroimidazo[1,2-b]pyridazin-2-yl)acetamide (Example 1, Step 4) (0.075 g, 0.36 mmol) was reacted with 3-(methylthio)phenylboronic acid (0.11 g, 0.64 mmol, Alfa Aesar, Ward Hill, Mass.) to afford the title compound as a yellow solid. MS (ESI positive ion) m/z: 299 (M+1). $^1$H NMR (400 MHz, DMSO-d$_6$): δ ppm 10.91 (s, 1H), 8.30 (s, 1H), 8.06 (d, J=9.6 Hz, 1H), 7.90 (s, 1H), 7.80-7.82 (m, 2H), 7.49 (t, J=7.8 Hz, 1H), 7.40-7.42 (m, 1H), 2.57 (s, 3H), 2.11 (s, 3H).

Example 10

N-(6-(5-(Methylsulfonyl)pyridin-3-yl)imidazo[1,2-b]pyridazin-2-yl)acetamide

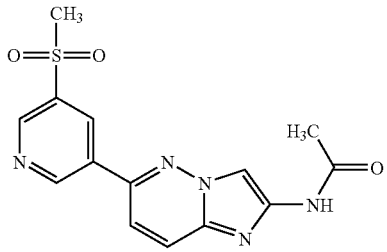

Following the procedure described for compound N-(6-(3-(4-methylphenylsulfonamido)phenyl)imidazo[1,2-b]pyridazin-2-yl)acetamide (Example 1), N-(6-chloroimidazo[1,2-b]pyridazin-2-yl)acetamide (Example 1, Step 4) (0.084 g, 0.40 mmol) was reacted with 5-(methylsulfonyl)pyridin-3-ylboronic acid (0.14 g, 0.72 mmol, Combi-Blocks, San Diego, Calif.) to afford the title compound as a yellow solid. MS (ESI positive ion) m/z: 332 (M+1). $^1$H NMR (400 MHz, DMSO-d$_6$): δ ppm 10.97 (s, 1H), 9.56 (d, J=2.2 Hz, 1H), 9.19 (d, J=2.2 Hz, 1H), 8.89 (t, J=2.2 Hz, 1H), 8.39 (s, 1H), 8.19 (d, J=9.4 Hz, 1H), 8.00 (d, J=9.4 Hz, 1H), 3.31 (s, 3H), 2.12 (s, 3H).

Example 11

N-(6-(5-(4-Fluorophenylsulfonamido)pyridin-3-yl)imidazo[1,2-b]pyridazin-2-yl)acetamide

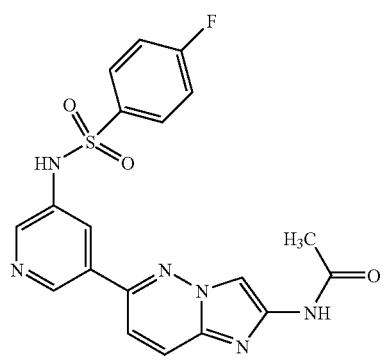

To a round-bottomed flask was added 5-bromopyridin-3-amine (0.80 g, 4.6 mmol, Matrix Scientific, Columbia, S.C.), ethanol (15 mL) and 4-fluorobenzenesulfonyl chloride (2.2 g, 12 mmol, Fluka (Sigma-Aldrich) Buchs, Switzerland). The mixture was allowed to stir at ambient temperature overnight. The mixture was diluted with CH$_2$Cl$_2$ and sat. NaHCO$_3$ and then the solution was extracted with CH$_2$Cl$_2$ (3×25 mL). The combined extracts were dried over Na$_2$SO$_4$, filtered and concentrated. Purification by silica gel chromatography (10-30% EtOAc/CH$_2$Cl$_2$) afforded N-(5-bromopyridin-3-yl)-4-fluorobenzenesulfonamide as an off-white crystalline solid (0.35 g, 23% yield). MS (ESI pos. ion) m/z: 333 (M+1). $^1$H NMR (400 MHz, MeOH-d$_4$) δ ppm 8.35 (s, 1H), 8.22 (s, 1H), 7.83-7.89 (m, 2H), 7.76-7.81 (m, 1H), 7.25-7.32 (m, 2H).

To a 25-mL, round-bottomed flask was added N-(5-bromopyridin-3-yl)-4-fluorobenzenesulfonamide (0.15 g, 0.45 mmol), bis(pinacolato)diboron (0.17 g, 0.68 mmol), potassium acetate (0.18 g, 1.8 mmol) and 1,4-dioxane (4.0 mL). The mixture was carefully evacuated and backfilled with N$_2$. To this mixture was added dichloro[1,1'-bis(diphenylphosphino)ferrocene]palladium(II)dichloromethane adduct (0.033 g, 0.045 mmol, Strem Chemicals, Inc., Newburyport, Mass.). The mixture was carefully evacuated and backfilled with N$_2$. The mixture was stirred at 90° C. for 19 h then allowed to cool to room temperature. To the solution was added DMF (4.0 mL), N-(6-chloroimidazo[1,2-b]pyridazin-2-yl)acetamide (Example 1, Step 4) (0.075 g, 0.36 mmol) and aq. Na$_2$CO$_3$ (0.89 mL, 1.8 mmol, 2 M). The mixture was carefully evacuated and backfilled with N$_2$. To the mixture was added trans-dichlorobis(triphenylphosphine)palladium (II) (0.025 g, 0.036 mmol, Strem Chemical, Inc., Newburyport, Mass.). Once again the mixture was carefully evacuated and backfilled with N$_2$. The mixture was stirred at 90° C. for 2 h and then was allowed to cool to room temperature. The solution was poured into water (100 mL), extracted with 25% iPrOH/CHCl$_3$ (3×75 mL) and the combined extracts were washed with brine, dried (Na$_2$SO$_4$) and concentrated onto silica. Purification by silica gel chromatography (2 to 8% MeOH (2 M in NH$_3$)/CH$_2$Cl$_2$) afforded the title compound as a tan solid. MS (ESI pos. ion) m/z: 427 (M+1). $^1$H NMR (400 MHz, DMSO-d$_6$): δ 10.95 (s, 1H), 10.84 (s, 1H), 8.92 (d, J=1.8 Hz, 1H), 8.41 (d, J=2.5 Hz, 1H), 8.31 (s, 1H), 8.09-8.13 (m, 2H), 7.88-7.91 (m, 2H), 7.76 (d, J=9.4 Hz, 1H), 7.42 (d, J=8.8 Hz, 2H), 2.12 (s, 3H).

Example 12

N-(6-(6-chloro-5-(4-fluorophenylsulfonamido)pyridin-3-yl)imidazo[1,2-b]pyridazin-2-yl)acetamide;

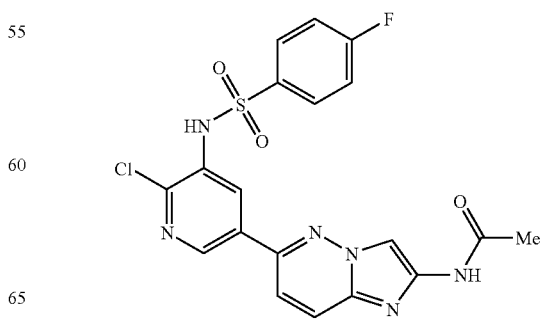

Step 1. N-(5-bromo-2-chloropyridin-3-yl)-4-fluorobenzenesulfonamide

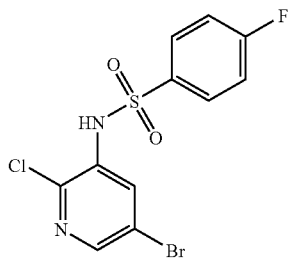

To a 50-mL, round-bottomed flask was added 3-amino-5-bromo-2-chloropyridine (0.50 g, 2.4 mmol, Asymchem, Morrisville, N.C.), pyridine (10 mL, 120 mmol) and 4-fluorobenzenesulfonyl chloride (2.0 g, 10 mmol, Fluka, Buchs, Switzerland). The mixture was stirred at 25° C. After 18 hours, the mixture was concentrated in vacuo. To the residue was added methanol (10 mL), 1,4-dioxane (10 mL) and potassium carbonate (3.4 g, 25 mmol). The mixture was stirred at 60° C. After 16 hours, the mixture was poured into water (100 mL) and the pH was adjusted to ~7 with 1 N HCl. The solution was extracted with EtOAc (3×75 mL) and the combined extracts were washed with water (100 mL), brine (100 mL) and then dried ($Na_2SO_4$) and concentrated onto silica. Purification by silica gel chromatography (2.0 to 30% EtOAc/hexane) afforded the title compound as a white solid (0.53 g, 58% yield). MS (ESI pos. ion) m/z: 367 (M+1). $^1$H NMR (400 MHz, DMSO-$d_6$) δ ppm 10.63 (br. s, 1H), 8.42 (d, J=2.3 Hz, 1H), 7.94 (d, J=2.3 Hz, 1H), 7.77-7.84 (m, 2H), 7.40-7.47 (m, 2H).

Step 2. N-(6-(6-chloro-5-(4-fluorophenylsulfonamido)pyridin-3-yl)imidazo[1,2-b]pyridazin-2-yl)acetamide

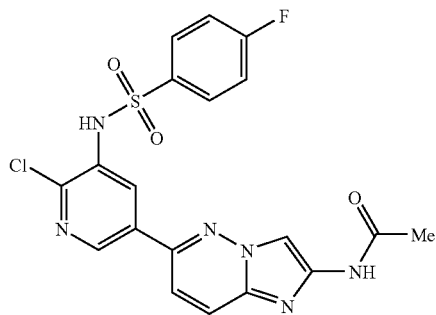

To a 25-mL, round-bottomed flask was added N-(5-bromo-2-chloropyridin-3-yl)-4-fluorobenzenesulfonamide (0.15 g, 0.41 mmol), bis(pinacolato)diboron (0.16 g, 0.62 mmol), potassium acetate (0.16 g, 1.6 mmol) and 1,4-dioxane (4.0 mL). The mixture was carefully evacuated and backfilled with $N_2$. To the solution was added dichloro[1,1'-bis(diphenylphosphino)ferrocene]palladium(II)dichloromethane adduct (0.030 g, 0.041 mmol). The mixture was carefully evacuated and backfilled with $N_2$ again then stirred at 90° C. for 6 h. The reaction mixture was cooled to rt and treated with DMF (4.0 mL, 52 mmol), N-(6-chloroimidazo[1,2-b]pyridazin-2-yl)acetamide (0.055 g, 0.26 mmol) and 2.0 M aq. sodium carbonate (0.78 mL, 1.6 mmol). The mixture was carefully evacuated and backfilled with $N_2$. To the solution was added trans-dichlorobis(triphenylphosphine)palladium (II) (0.018 g, 0.026 mmol) and then the solution was carefully evacuated and backfilled with $N_2$ again. The mixture was stirred at 90° C. for 16 hours then poured into aq. NaCl (100 mL) and extracted with 25% iPrOH/CHCl$_3$ (3×75 mL). The combined extracts were dried ($Na_2SO_4$) and concentrated in vacuo to remove the DMF. The solution was then taken up in MeOH/$CH_2Cl_2$ and concentrated onto silica. Purification by silica gel chromatography (0.5 to 5.0% MeOH (2 M in $NH_3$)/$CH_2Cl_2$) afforded the title compound as a yellow solid. MS (ESI pos. ion) m/z: 461 (M+1). $^1$H NMR (400 MHz, DMSO-$d_6$) δ ppm 10.96 (s, 1H), 10.57 (s, 1H), 8.92 (d, J=2.2 Hz, 1H), 8.31-8.36 (m, 2H), 8.13 (d, J=9.4 Hz, 1H), 7.80-7.88 (m, 3H), 7.39-7.48 (m, 2H), 2.13 (s, 3H).

An alternative procedure for making N-(6-(6-chloro-5-(4-fluorophenylsulfonamido)pyridin-3-yl)imidazo[1,2-b]pyridazin-2-yl)acetamide is set forth below.

To a 250 mL round-bottomed flask was added N-(6-chloroimidazo[1,2-b]pyridazin-2-yl)acetamide (2.50 g, 11.9 mmol), N-(2-chloro-5-(4,4,5,5-tetramethyl-1,3,2-dioxaborolan-2-yl)pyridin-3-yl)-4-fluorobenzenesulfonamide (5.39 g, 13.1 mmol) (from Step 2 of Example 48), DMSO (50.0 mL, 705 mmol) and aq sodium carbonate (26.7 mL, 53.4 mmol, 2 M). The mixture was carefully evacuated and backfilled with $N_2$. To the mixture was added trans-dichlorobis(triphenylphosphine)palladium (II) (0.667 g, 0.950 mmol, Strem Chemical, Inc., Newburyport, Mass.). Again, the mixture was carefully evacuated and backfilled with $N_2$. The mixture was stirred at 90° C. The mixture was allowed to cool to rt and then was poured into a solution of pH 4.8 buffer (300 mL, 3 M sodium acetate solution pH adjusted to 4.8, Teknova, Hollister, Mass.) and water (300 mL). A precipitate formed and the solution was allowed to sit overnight and then filtered. The filtercake was washed with pH 4.8 buffer (Teknova, 3 M sodium acetate solution pH adjusted to 4.8), then pure water and then was dried by passing air through the filter. 7.05 grams of a brown solid were isolated. The solid was dissolved in DMF (125 mL) and treated with Siliabond-TAAcONa (11.0 grams, 5 equiv. relative to mmol of Pd catalyst used, loading=0.43 mmol/gram, Silicycle brand palladium scavenger, Silicycle, Quebec City, Quebec, Canada). The mixture was heated at 50° C. for 19 h. The solution was then filtered through Celite® (diatomaceous earth), diluted with diethylamine, filtered through a 0.45 um poly(tetrafluoroethylene) syringe filter and purified by preparative HPLC (Chiralpak ASH (21×250 mm, 5 um) column, 25% B, hold for 0.5 min, ramp up to 45% B at 4% B/min and then ramp up to 60% B at 50% B/min; hold for 2 min and reequilibrate for 1.1 min. Total flow was 50 mL/min, outlet pressure was 100 bar, column temperature was 35° C. A=supercritical $CO_2$, B=methanol with 0.2% diethylamine). A portion of the purified material (1.195 g) was dissolved in water (100 mL) and then treated with AcOH (0.51 mL). A precipitate formed. This was stirred for 15 min and then allowed to sit for 2 h. The solution was then filtered and the filtercake was washed with water (3×15 mL) and then dried by letting air pass through the fritted funnel and then the material was dried under vacuum (250 mtor, 45° C., 16 h) to afford a light brown solid 0.962 g.

Imidazopyridines—Exemplary Syntheses

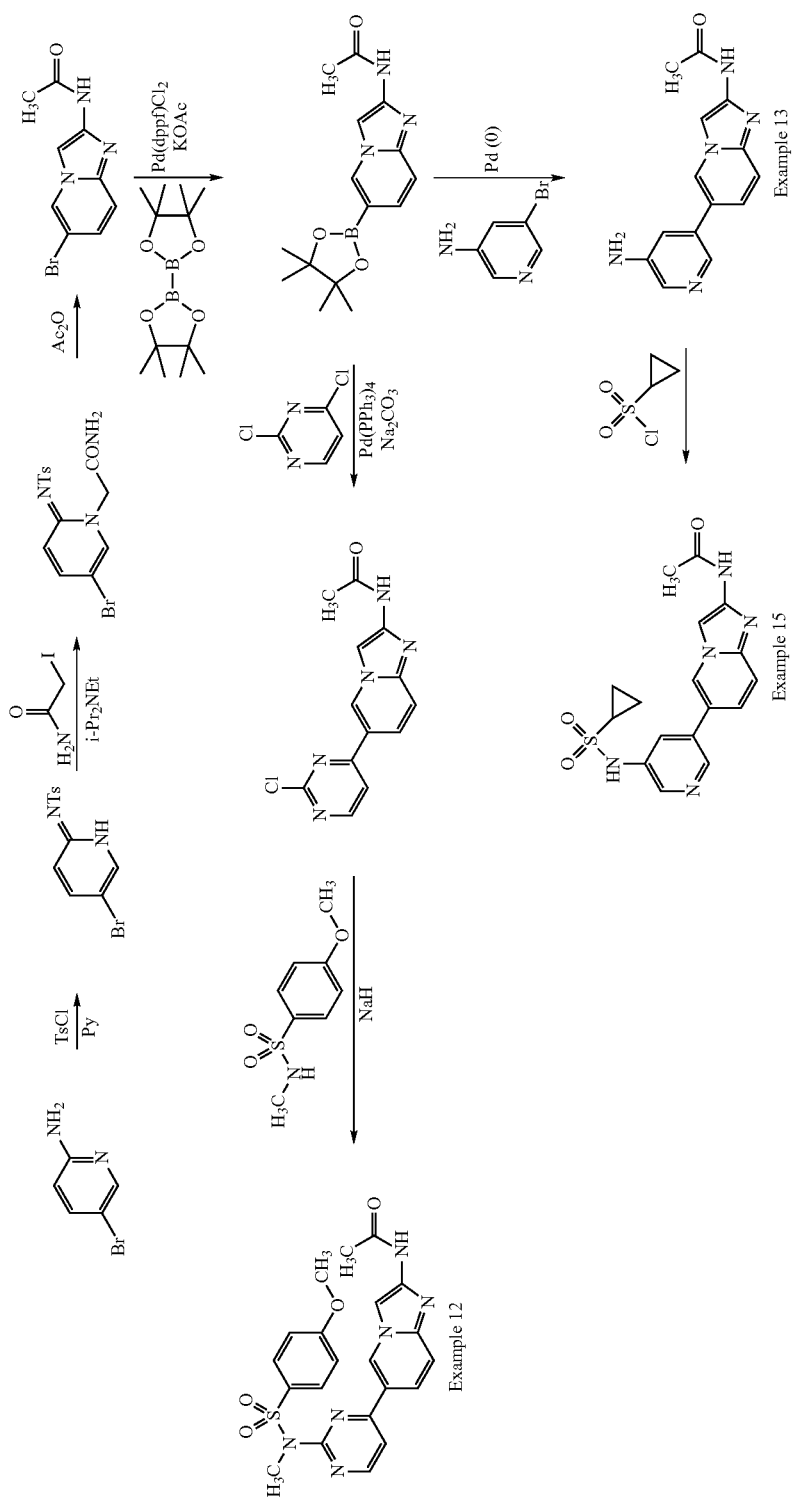

Example 13

N-(6-(2-(4-Methoxy-N-methylphenylsulfonamido) pyrimidin-4-yl)H-imidazo[1,2-a]pyridin-2-yl)acetamide

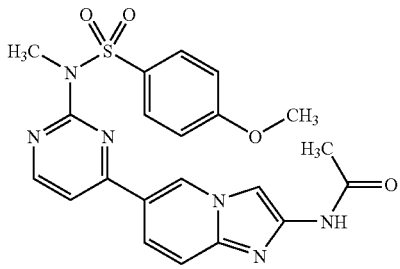

Step 1. N-(5-Bromopyridin-2(1H)-ylidene)-4-methylbenzenesulfonamide

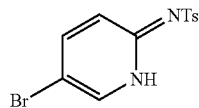

To a solution of 5-bromopyridin-2-amine (10.4 g, 60 mmol, Aldrich, St. Louis, Mo.) in pyridine (50 mL) was added p-toluenesulfonyl chloride (13 g, 66 mmol). The mixture was heated to 85° C. for 12 h. The solvent was removed under reduced pressure and the residue was taken up in 1 L of water and stirred for 1.5 h. The solid was collected by filtration and recrystallized from EtOAc to afford N-(5-bromopyridin-2(1H)-ylidene)-4-methylbenzenesulfonamide (11.3 g, 57% yield) as a white powder. $^1$H NMR (400 MHz, DMSO-$d_6$): δ ppm 11.23 (s, 1H), 8.27 (d, J=2.5 Hz, 1H), 7.89 (dd, J=8.8 Hz, 2.4 Hz, 1H), 7.79 (d, J=8.2 Hz, 2H), 7.37 (d, J=8.2 Hz, 2H), 7.03 (d, J=8.8 Hz, 1H), 2.35 (s, 3H).

Step 2. 2-(5-Bromo-2-(4-methylphenylsulfonamido) pyridin-1(2H)-yl)acetamide

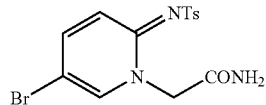

To a suspension of N-(5-bromopyridin-2(1H)-ylidene)-4-methylbenzenesulfonamide (step 1) (11.3 g, 34.5 mmol) in DMF (70 mL) was added Huenig's base (N-ethyldiisopropyl amine) (6.62 mL, 38.0 mmol) and 2-iodoacetamide (7.03 g, 38.0 mmol). The mixture was stirred at room temperature for 15 h. The mixture was poured into 750 mL of water. The mixture was stirred for 90 min and the solid precipitate was collected by filtration. The filter-cake was washed with water and then ether, and then dried at 70° C. under vacuum for 1 h to afford 2-(5-bromo-2-(4-methylphenylsulfonamido)pyridin-1(2H)-yl)acetamide (13.0 g, 98.0% yield) as a white solid. $^1$H NMR (400 MHz, DMSO-$d_6$): δ ppm 8.37 (d, J=2.2 Hz, 1H), 7.88 (dd, J=9.7 Hz, 2.5 Hz, 1H), 7.79 (s, 1H), 7.65 (d, J=8.2 Hz, 2H), 7.39 (s, 1H), 7.29 (t, J=9.3 Hz, 3H), 4.79 (s, 2H), 2.34 (s, 3H).

Step 3. N-(6-BromoH-imidazo[1,2-a]pyridin-2-yl)acetamide

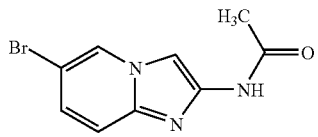

A mixture of 2-(5-bromo-2-(4-methylphenylsulfonamido) pyridin-1(2H)-yl)acetamide (step 2) (13.0 g, 34 mmol) and Ac$_2$O (30 mL, 318 mmol) was heated to 135° C. for 2.5 h and cooled to room temperature. The cooled mixture was diluted with hexane-ether (10:1, 100 mL), stirred and decanted. The residue was further washed with ether and decanted, and then treated with NaOH (1 N, 30 mL), the solid precipitate was collected by filtration, the filter-cake was washed with acetone-H$_2$O (1:3), EtOAc-hexane (1:1), and hexane-CH$_2$Cl$_2$ (5:1) to give the title product (2.7 g, 32% yield) as a tan solid. MS (ESI positive ion) m/z: 254 (M+1). $^1$H NMR (400 MHz, DMSO-$d_6$): δ ppm 10.74 (s, 1H), 8.87 (d, J=1.17 Hz, 1H), 8.10 (s, 1H), 7.40 (d, J=9.59 Hz, 1H), 7.30 (d, J=9.39 Hz, 1H), 2.07 (s, 3H).

Step 4. N-(6-(4,4,5,5-Tetramethyl-1,3,2-dioxaborolan-2-yl)H-imidazo[1,2-a]pyridin-2-yl)acetamide

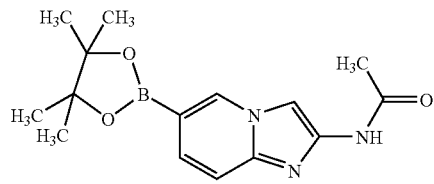

A mixture of N-(6-bromoH-imidazo[1,2-a]pyridin-2-yl)acetamide (step 3) (510 mg, 2.0 mmol), 4,4,5,5-tetramethyl-2-(4,4,5,5-tetramethyl-1,3,2-dioxaborolan-2-yl)-1,3,2-dioxaborolane (560 mg, 2.2 mmol), potassium acetate (591 mg, 6.0 mmol), Pd(dppf)Cl$_2$ (88.0 mg, 0.1 mmol) in dioxane/DMF (4 mL/1 mL) was purged with nitrogen for 5 min. The mixture was heated to 105° C. for 3 h and cooled to room temperature. The reaction mixture was quenched with H$_2$O (15 mL), the solid precipitate was collected by filtration to provide N-(6-(4,4,5,5-tetramethyl-1,3,2-dioxaborolan-2-yl) H-imidazo[1,2-a]pyridin-2-yl)acetamide as a tan solid, which was used for next step without further purification.

Step 5. N-(6-(2-Chloropyrimidin-4-yl)H-imidazo[1,2-a]pyridin-2-yl)acetamide

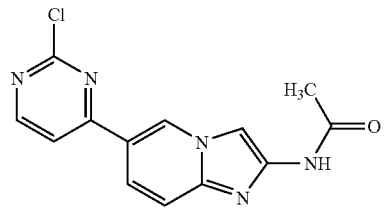

A mixture of N-(6-(4,4,5,5-tetramethyl-1,3,2-dioxaborolan-2-yl)H-imidazo[1,2-a]pyridin-2-yl)acetamide (step 4) (640 mg, 2.1 mmol), 2,4-dichloropyrimidine (550 mg, 3.2 mmol), sodium carbonate (676 mg, 6.4 mmol), Pd(PPh$_3$)$_4$ (123 mg, 0.1 mmol) in dioxane/H$_2$O (10 mL/3 mL) was heated under nitrogen at 100° C. for 14 h and cooled to room temperature. The solid precipitate was collected by filtration, the filter-cake was washed with H$_2$O, EtOAc, DCM, and acetone to give N-(6-(2-chloropyrimidin-4-yl)H-imidazo[1,2-a]pyridin-2-yl)acetamide (370 mg, 61% yield) as a green solid. MS (ESI pos. ion) m/z: 288 (M+1). $^1$H NMR (400 MHz, DMSO-$d_6$): δ10.82 (s, 1H), 9.53 (s, 1H), 8.83 (d, J=5.12 Hz, 1H), 8.32 (s, 0.5H), 8.24 (s, 1H), 8.10 (d, J=5.12 Hz, 1H), 7.96 (d, J=9.50 Hz, 1H), 7.57 (d, J=9.65 Hz, 1H), 2.09 (s, 3H).

Step 6. N-(6-(2-(4-Methoxy-N-methylphenylsulfona-
mido)pyrimidin-4-yl)H-imidazo[1,2-a]pyridin-2-yl)
acetamide

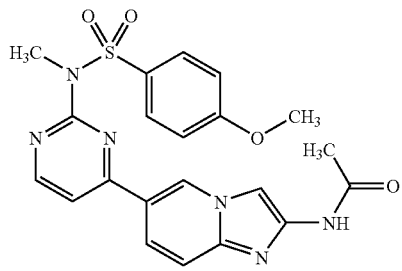

To a solution of 4-methoxybenzene-1-sulfonyl chloride (2.4 g, 12 mmol) in CHCl₃ (20 mL) was added methanamine (5 mL, 40 mmol) in EtOH. The mixture was stirred at room temperature for 16 h. The mixture was concentrated under reduced pressure. The resulting solid was washed with H₂O (5 mL), ether, and air-dried to give 4-methoxy-N-methylbenzenesulfonamide (1.12 g, 48% yield) as a white solid. MS (ESI positive ion) m/z: 202 (M+1).
A mixture of 4-methoxy-N-methylbenzenesulfonamide (210 mg, 1.04 mmol) and NaH (55.0 mg, 1.4 mmol) in DMSO (1.5 mL) was stirred under nitrogen at 70° C. for 10 min. To this suspension, N-(6-(2-chloropyrimidin-4-yl)indolizin-2-yl)acetamide (step 3) (200 mg, 0.7 mmol) was added, the orange mixture was heated at 120° C. for 3 h and cooled to room temperature. The mixture was treated with H₂O (10 mL) and the suspension was stirred at room temperature for 1 h. The solid precipitate was collected by filtration, the filter-cake was washed with hot hexane-CHCl₃, hexane-acetone, and hexane-MeOH to give N-(6-(2-(4-Methoxy-N-methylphenylsulfonamido)pyrimidin-4-yl)H-imidazo[1,2-a]pyridin-2-yl)acetamide as a dark brown solid. MS (ESI positive ion) m/z: 453 (M+1). ¹H NMR (400 MHz, DMSO-d₆): δ ppm 10.32 (s, 1H), 8.82 (s, 1H), 8.53 (s, 1H), 8.14 (s, 1H), 7.98 (d, J=7.04 Hz, 2H), 7.71 (d, J=7.43 Hz, 1H), 7.46 (d, J=9.98 Hz, 1H), 7.32 (s, 1H), 6.97 (d, J=5.87 Hz, 2H), 3.86 (s, 3H), 3.76 (s, 3H), 2.22 (s, 3H).

Example 14

N-(6-(5-Aminopyridin-3-yl)H-imidazo[1,2-a]pyridin-2-yl)acetamide

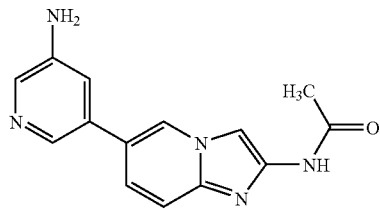

Step 1

N-(6-(4,4,5,5-Tetramethyl-1,3,2-dioxaborolan-2-yl)
H-imidazo[1,2-a]pyridin-2-yl)acetamide

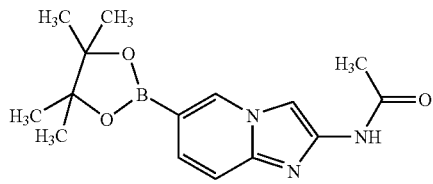

A mixture of Pd(dppf)Cl₂*DCM (0.187 g, 0.256 mmol), potassium acetate (1.60 g, 16.3 mmol), 4,4,5,5-tetramethyl-2-(4,4,5,5-tetramethyl-1,3,2-dioxaborolan-2-yl)-1,3,2-dioxaborolane (Aldrich, St. Louis, Mo.) (1.40 g, 5.51 mmol), N-(6-bromoH-imidazo[1,2-a]pyridin-2-yl)acetamide (step 3) (1.30 g, 5.12 mmol) in dioxane (6 mL) and DMF (3 mL) was purged with nitrogen for 5 min and then heated to 105° C. for 5 hr. The mixture was used directly in the next step.

Step 2

N-(6-(5-Aminopyridin-3-yl)H-imidazo[1,2-a]pyridin-2-yl)acetamide

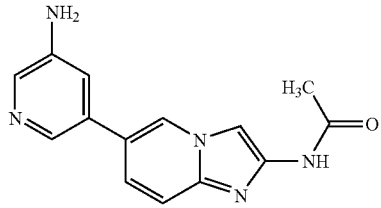

To the reaction mixture of N-(6-(4,4,5,5-tetramethyl-1,3,2-dioxaborolan-2-yl)H-imidazo[1,2-a]pyridin-2-yl)acetamide (step A) (1.54 g, 5.1 mmol) was added water (4 mL), sodium carbonate (1.6 g, 15 mmol), Pd(PPh₃)₄ (0.30 g, 0.26 mmol) and 5-bromopyridin-3-amine (1.3 g, 7.7 mmol). heated to 105° C. overnight. H₂O (10 mL) was added and the reaction mixture was cooled to rt and filtered. The residue was washed with EtOAc (2×15 mL), DCM-EtOAc (20%), MeOH in DCM (5%); DMF in EtOAc (5%), and finally DCM to give a yellow solid (690 mg). LCMS: calc'd for C₁₄H₁₃N₅O: 267.1; found: 268.1 (M+1). ¹H NMR (400 MHz, DMSO-d₆) δ ppm 2.08 (s, 3H) 5.45 (s, 2H) 7.14 (s, 1H) 7.47 (d, J=13.50 Hz, 2H) 7.86-8.21 (m, 3H) 8.86 (s, 1H) 10.71 (s, 1H)

Example 15

N-(6-(5-(4-Fluorophenylsulfonamido)pyridin-3-yl)
H-imidazo[1,2-a]pyridin-2-yl)acetamide

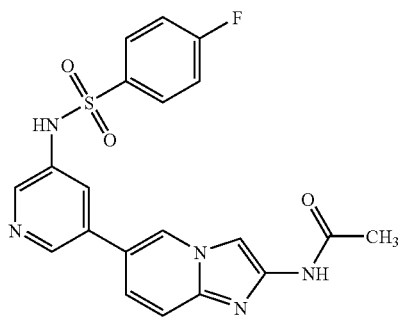

To a 10-mL, round-bottomed flask was added N-(6-(5-aminopyridin-3-yl)H-imidazo[1,2-a]pyridin-2-yl)acetamide (Example 14) (0.10 g, 0.37 mmol), pyridine (4.0 mL), 4-fluorobenzenesulfonyl chloride (0.44 g, 2.2 mmol) and DMAP (0.5 mg, 0.0037 mmol). The mixture was stirred at 25° C. for 20 min. The mixture was poured into water (100 mL) and extracted with 25% iPrOH/CHCl₃ (3×50 mL). The combined extracts were dried (Na₂SO₄) and concentrated onto silica. Purification by silica gel chromatography (3.0 to 9.0% MeOH (2 M in NH₃)/CH₂Cl₂) afforded the title compound as a tan solid. MS (ESI positive ion) m/z: 426 (M+1). ¹H NMR (400 MHz, DMSO-d₆) δ ppm 10.70-10.79 (m, 2H), 8.92 (s, 1H), 8.61 (d, J=2.0 Hz, 1H), 8.25 (d, J=2.3 Hz, 1H), 8.16 (s, 1H), 7.87-7.92 (m, 2H), 7.77 (t, J=2.1 Hz, 1H), 7.53 (d, J=9.4 Hz, 1H), 7.39-7.46 (m, 3H), 2.09 (s, 3H).

Example 16

N-(6-(5-(Cyclopropanesulfonamido)pyridin-3-yl)H-imidazo[1,2-a]pyridin-2-yl)acetamide (TFA Salt)

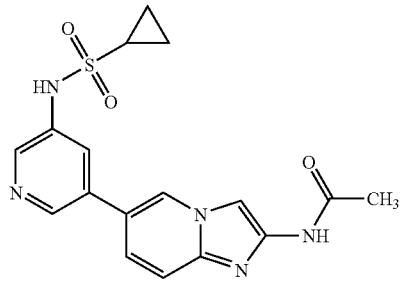

To a 10-mL, round-bottomed flask was added N-(6-(5-aminopyridin-3-yl)H-imidazo[1,2-a]pyridin-2-yl)acetamide (Example 14) (0.10 g, 0.37 mmol), pyridine (4.0 mL) and cyclopropanesulfonyl chloride (0.23 mL, 2.3 mmol). The mixture was stirred at 25° C. for 4 h and then concentrated. The residue was diluted with MeOH and DMSO, filtered and purified by preparative HPLC (Phenomenex Synergi 4μ MAX-RP 150×21.2 mm, 2 to 100% $CH_3CN/H_2O$, 0.1% TFA, over 15 min) (Phenomenex, Torrance, Calif.) to afford the title compound as an off-white solid. MS (ESI positive ion) m/z: 372 (M+1). $^1$H NMR (400 MHz, DMSO-$d_6$) δ ppm 10.90 (s, 1H), 10.22 (s, 1H), 9.05 (s, 1H), 8.68 (d, J=2.0 Hz, 1H), 8.47 (d, J=2.3 Hz, 1H), 8.18 (s, 1H), 7.91 (t, J=2.2 Hz, 1H), 7.61-7.67 (m, 2H), 2.80-2.87 (m, 1H), 2.11 (s, 3H), 0.96-1.04 (m, 4H).

Example 17

N-(6-(5-(Methylsulfonamido)pyridin-3-yl)H-imidazo[1,2-a]pyridin-2-yl)acetamide (TFA Salt)

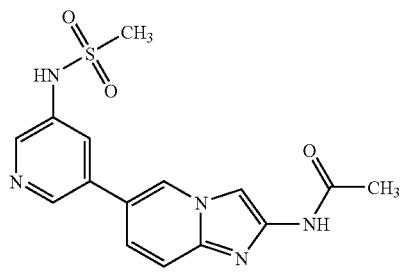

Following the procedure described for compound N-(6-(5-(cyclopropanesulfonamido)pyridin-3-yl)H-imidazo[1,2-a]pyridin-2-yl)acetamide (TFA salt) (Example 16), N-(6-(5-aminopyridin-3-yl)H-imidazo[1,2-a]pyridin-2-yl)acetamide (Example 14) (0.10 g, 0.37 mmol) was reacted with methanesulfonyl chloride (0.17 mL, 2.2 mmol) to afford the title compound as a tan solid. MS (ESI positive ion) m/z: 346 (M+1). $^1$H NMR (400 MHz, DMSO-$d_6$) δ ppm 10.98 (s, 1H), 10.27 (s, 1H), 9.08 (s, 1H), 8.69 (d, J=1.6 Hz, 1H), 8.47 (d, J=2.2 Hz, 1H), 8.17 (s, 1H), 7.90 (t, J=2.1 Hz, 1H), 7.64-7.74 (m, 2H), 3.17 (s, 3H), 2.12 (s, 3H).

Example 18

N-(6-(5-(3,3-Dimethylbutylamino)pyridin-3-yl)H-imidazo[1,2-a]pyridin-2-yl)acetamide

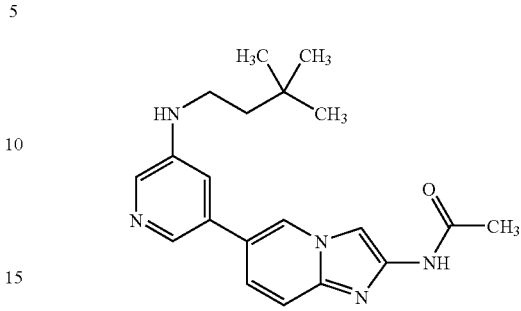

To a mixture of N-(6-(5-aminopyridin-3-yl)H-imidazo[1,2-a]pyridin-2-yl)acetamide (Example 14) (70 mg, 262 μmol) and 3,3-dimethylbutanal (160 mg, 1597 μmol) in EtOH (1.5 mL)-$CH_2Cl_2$ (2 mL) in the presence of HOAc (1 drop) was added sodium triacetoxyborohydride (220 mg, 1038 μmol). After 12 h, the mixture was partitioned between aqueous $NaHCO_3$ and $CH_2Cl_2$. The organic layer was dried over $Na_2SO_4$ and concentrated. The residue was purified on silica using (2N $NH_3$ in MeOH) in DCM (0-5%) to give a white powder. LCMS: calc'd for $C_{20}H_{25}N_5O$: 351.2; found 352.2 (M+1). $^1$H NMR (400 MHz, chloroform-d) δ ppm 1.01 (s, 9H) 1.54-1.62 (m, 2H) 2.24 (s, 3H) 3.15-3.25 (m, 2H) 3.73 (t, J=5.28 Hz, 1H) 7.40 (dd, J=9.29, 1.66 Hz, 1H) 7.51 (d, J=9.19 Hz, 1H) 8.04 (d, J=2.54 Hz, 1H) 8.11-8.16 (m, 2H) 8.27 (d, J=0.78 Hz, 1H) 9.18 (s, 1H)

Example 19

N-(6-(6-Chloro-5-(methylsulfonamido)pyridin-3-yl)imidazo[1,2-b]pyridazin-2-yl)acetamide

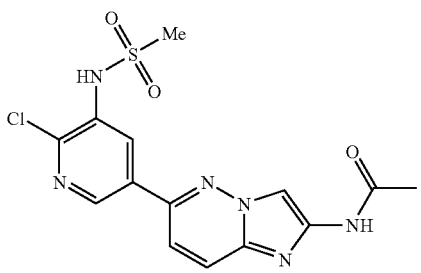

Step 1.
N-(5-bromo-2-chloropyridin-3-yl)methanesulfonamide

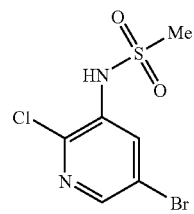

To a 25 mL round-bottomed flask was added was added 5-bromo-2-chloropyridin-3-amine (1.50 g, 7.23 mmol, Asymchem, Morrisville, N.C.), pyridine (20.0 mL, 248 mmol) and methanesulfonyl chloride (2.8 mL, 36 mmol). The mixture was stirred at 25° C. for 48 h. The mixture was then concentrated in vacuo and the residue was treated with methanol (30 mL), 1,4-dioxane (30 mL) and potassium carbonate (10 g, 72 mmol) and stirred at 60° C. for 5 h. The mixture was poured into water (300 mL) and acidified to pH 5 using conc HCl. To the solution was added pH 4.8 buffer (100 mL, Teknova, 3 M sodium acetate solution pH adjusted to 4.8) and the solution was extracted with EtOAc (3×100 mL). The combined extracts were washed with water (1×100 mL), brine (100 mL) and then dried ($Na_2SO_4$) and concentrated onto silica. Purification by silica gel chromatography (5 to 60% EtOAc/hexane) afforded a semi-solid that was washed with 10% EtOAc/hexane to afford the title compound as a tan solid (1.68 g, 81%). MS (ESI, positive ion) m/z: 285 (M($^{79}$Br)+1), 287 (M($^{81}$Br)+1).

Step 2. N-(6-(6-chloro-5-(methylsulfonamido)pyridin-3-yl)imidazo[1,2-b]pyridazin-2-yl)acetamide

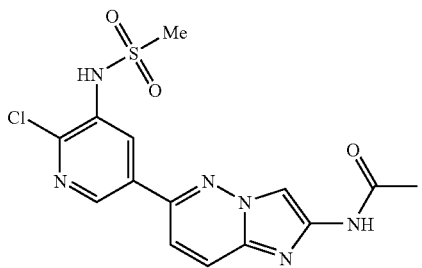

To a 25 mL round-bottomed flask was added N-(6-chloroimidazo[1,2-b]pyridazin-2-yl)acetamide (0.750 g, 3.56 mmol), bis(pinacolato)diboron (1.18 g, 4.63 mmol, Aldrich, St. Louis, Mo.), DMSO (30.0 mL, 423 mmol) and potassium acetate (1.40 g, 14.2 mmol). The mixture was carefully evacuated and backfilled with $N_2$. To the mixture was added dichloro[1,1'-bis(diphenylphosphino)ferrocene]palladium (II)dichloromethane adduct (0.291 g, 0.356 mmol, Strem Chemical, Inc., Newburyport, Mass.). The mixture was carefully evacuated and backfilled with $N_2$ and then was stirred at 90° C. for 2 h. The reaction was allowed to cool to rt and treated with N-(5-bromo-2-chloropyridin-3-yl)methanesulfonamide (1.00 g, 3.50 mmol), and aq sodium carbonate (5.25 mL, 10.5 mmol, 2 M). The mixture was carefully evacuated and backfilled with $N_2$. To the mixture was added trans-dichlorobis(triphenylphosphine)palladium(II) (0.246 g, 0.350 mmol, Strem Chemical, Inc., Newburyport, Mass.). Again, the mixture was carefully evacuated and backfilled with $N_2$ and was stirred at 90° C. for 1 h. The reaction mixture was cooled to rt and concentrated in vacuo. The residue was taken up in 10 mL DMSO and 20 mL MeOH. The solution was filtered. The filtercake was isolated and suspended in water (50 mL) and treated with pH 4.8 buffer (25 mL, Teknova, 3 M sodium acetate solution pH adjusted to 4.8). The solution was allowed to stand for 30 minutes and then filtered. The filtercake was washed with water and then dried under vacuum to afford the title compound as a tan solid (0.415 g, 31%). MS (ESI, positive ion) m/z: 381 (M+1). $^1$H NMR (400 MHz, DMSO-$d_6$) δ ppm 2.12 (s, 3H), 3.17 (s, 3H), 7.85 (d, J=9.4 Hz, 1H), 8.14 (d, J=9.4 Hz, 1H), 8.34 (s, 1H), 8.43 (s, 1H), 8.89 (s, 1H), 9.92 (s, 1H), 10.95 (s, 1H).

Example 20

N-(6-(5,6-Dimethoxypyridin-3-yl)imidazo[1,2-b]pyridazin-2-yl)acetamide

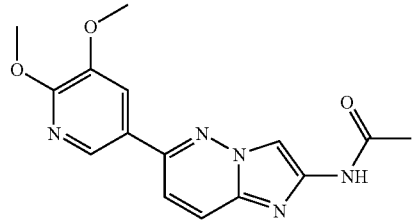

Step 1. 5-bromo-2,3-dimethoxypyridine

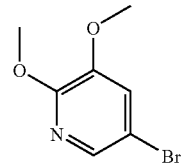

To a 100 mL round-bottomed flask was added 2,3-dimethoxypyridine (2 mL, 15 mmol, Alfa Aesar, Ward Hill, Mass.), $CH_2Cl_2$ (30 mL), and bromine (0.7 mL, 14 mmol). The reaction mixture was stirred at rt for 16 h. The reaction mixture was then diluted with sat. $NaHCO_3$ (30 mL) and extracted with EtOAc (2×50 mL). The combined organic extracts were washed with sat. NaCl (20 mL), dried over $Na_2SO_4$, filtered and concentrated. Purification by silica gel chromatography (50% $CH_2Cl_2$/hexanes) afforded the title compound (1.98 g, 60%). MS (ESI, positive ion) m/z: 218 (M($^{79}$Br)+1).

Step 2. N-(6-(5,6-dimethoxypyridin-3-yl)imidazo[1,2-b]pyridazin-2-yl)acetamide

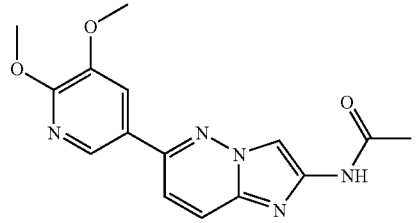

Following the procedure described for N-(6-(6-chloro-5-(methylsulfonamido)pyridin-3-yl)imidazo[1,2-b]pyridazin-2-yl)acetamide (Example 19), N-(6-chloroimidazo[1,2-b]pyridazin-2-yl)acetamide (0.132 g, 0.627 mmol) was reacted with bis(pinacolato)diboron (0.207 g, 0.815 mmol), DMSO (6.00 mL, 84.5 mmol) and potassium acetate (0.246 g, 2.51 mmol) and dichloro[1,1'-bis(diphenylphosphino)ferrocene] palladium(II)dichloromethane adduct (0.050 g, 0.062 mmol, Strem Chemical, Inc., Newburyport, Mass.) for 6 h. This was followed by treatment with 5-bromo-2,3-dimethoxypyridine (0.136 g, 0.624 mmol), aq sodium carbonate (0.312 mL, 0.624 mmol, 2 M) and trans-dichlorobis(triphenylphosphine) palladium(II) (0.0438 g, 0.0624 mmol, Strem). Purification by preparative HPLC (Phenomenex Gemini 5 micron (Phenomenex, Torrance, Calif.), C18, 100×30 mm, 5 to 65% CH$_3$CN(0.1% TFA)/H$_2$O(0.1% TFA) over 20 min then 100% CH$_3$CN(0.1% TFA) for 3 minutes at 20 mL/min) followed by conversion to the free base by loading the purified material onto a 1000 mg SCX (cation exchange resin, Radleys Discovery Technology, Essex, UK) cartridge and elution with MeOH(2M NH$_3$)/CH$_2$Cl$_2$ which, after concentration, afforded the title compound (0.0318 g, 16%) as a yellow solid. MS (ESI, positive ion) m/z: 314 (M+1). $^1$H NMR (400 MHz, DMSO-d$_6$) δ ppm 2.11 (s, 3H), 3.92 (s, 3H), 3.95 (s, 3H), 7.83 (d, J=9.6 Hz, 1H), 7.87 (d, J=2.0 Hz, 1H), 8.05 (d, J=9.6 Hz, 1H), 8.29 (s, 1H), 8.41 (d, J=2.0 Hz, 1H), 10.89 (s, 1H).

Example 21

N-(6-(6-Chloro-5-(methylsulfonamido)pyridin-3-yl)-3-iodoimidazo[1,2-b]pyridazin-2-yl)acetamide

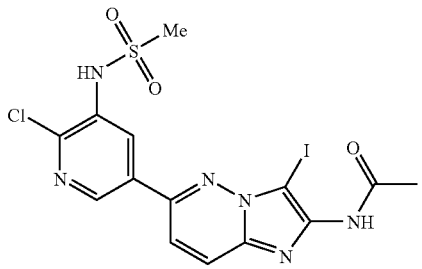

To a 50 mL round-bottomed flask was added N-(6-(6-chloro-5-(methylsulfonamido)pyridin-3-yl)imidazo[1,2-b]pyridazin-2-yl)acetamide (Example 19) (0.404 g, 1.06 mmol), chloroform (20 mL) and N-iodosuccinimide (0.48 g, 2.1 mmol). The mixture was stirred at 25° C. for 1 h then poured into CH$_2$Cl$_2$ (200 mL) and water (200 mL). The solution contained a precipitate. This was filtered and the filter-cake was washed with water and then dried under vacuum. The solid was taken up in MeOH/CH$_2$Cl$_2$ and concentrated onto Celite® (diatomaceous earth). Purification by silica gel chromatography (2.0 to 10% MeOH/CH$_2$Cl$_2$) afforded the title compound as a yellow solid (0.199 g, 37%). MS (ESI, positive ion) m/z: 506.4 (M+1). $^1$H NMR (400 MHz, DMSO-d$_6$) δ ppm 2.07 (s, 3H), 3.20 (s, 3H), 7.96 (d, J=9.6 Hz, 1H), 8.20 (d, J=9.4 Hz, 1H), 8.55 (d, J=2.2 Hz, 1H), 8.98 (d, J=2.2 Hz, 1H), 9.98 (s, 1H), 10.13 (s, 1H).

Example 22

N-(6-(6-Chloro-5-(methylsulfonamido)pyridin-3-yl)-3-(3-fluorophenyl)imidazo[1,2-b]pyridazin-2-yl)acetamide (TFA Salt)

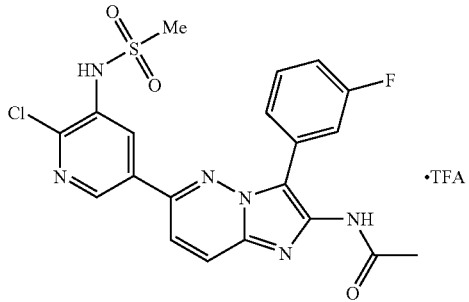

To a 10 mL round-bottomed flask was added N-(6-(6-chloro-5-(methylsulfonamido)pyridin-3-yl)-3-iodoimidazo[1,2-b]pyridazin-2-yl)acetamide (Example 21) (0.0820 g, 0.162 mmol), DMSO (2.50 mL, 35.2 mmol), 3-fluorophenylboronic acid (0.0272 g, 0.194 mmol, Aldrich, St. Louis, Mo.), and sodium carbonate (0.405 mL, 0.809 mmol, 2 M). The mixture was carefully evacuated and backfilled with N$_2$. To the mixture was added trans-dichlorobis(triphenylphosphine)palladium(II) (0.011 g, 0.0162 mmol, Strem Chemical, Inc., Newburyport, Mass.). Again, the mixture was carefully evacuated and backfilled with N$_2$. The mixture was stirred at 90° C. for 40 min, allowed to cool to rt. and then directly purified by preparative HPLC (Phenomenex Gemini 5 micron (Phenomenex, Torrance, Calif.), C18, 100×30 mm, 5 to 75% CH$_3$CN(0.1% TFA)/H$_2$O(0.1% TFA) over 20 min then 100% CH$_3$CN(0.1% TFA) for 3 minutes at 20 mL/min) with the fractions containing suspected product concentrated to afford the title compound as a yellow solid (0.059 g, 62%). MS (ESI, positive ion) m/z: 475 (M-TFA+1). $^1$H NMR (400 MHz, DMSO-d$_6$) δ ppm 2.04 (s, 3H), 3.20 (s, 3H), 7.25-7.28 (m, 1H), 7.53-7.60 (m, 1H), 7.70-7.75 (m, 1H), 7.77-7.81 (m, 1H), 8.02 (d, J=9.6 Hz, 1H), 8.32 (d, J=9.6 Hz, 1H), 8.52 (d, J=2.2 Hz, 1H), 8.95 (d, J=2.2 Hz, 1H), 9.92 (s, 1H), 10.24 (s, 1H).

Example 23

N-(5-(2-Amino-3-(3-fluorophenyl)imidazo[1,2-b]pyridazin-6-yl)-2-chloropyridin-3-yl)methanesulfonamide

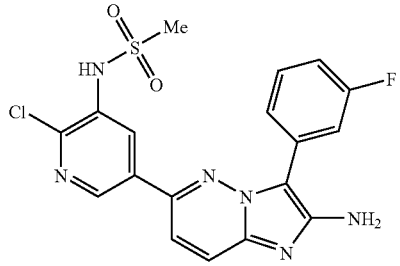

To a 4-mL vial was added N-(6-(6-chloro-5-(methylsulfonamido)pyridin-3-yl)-3-(3-fluorophenyl)imidazo[1,2-b]pyridazin-2-yl)acetamide (TFA salt) (Example 22) (0.025 g, 0.042 mmol), methanol (2.5 mL) and sodium hydroxide (0.250 mL, 2.5 mmol, 10 M). The mixture was stirred at 60° C. for 15 h. After cooling to rt, the mixture was neutralized with pH 4.8 buffer (Teknova, 3 M sodium acetate solution pH adjusted to 4.8). The solution was partially concentrated to remove the MeOH. The solution was filtered and the filter-cake was washed with water (2×) and then dried under vacuum to afford the title compound as a yellow solid (0.016 g, 86%). MS (ESI, positive ion) m/z: 433 (M+1). $^1$H NMR (400 MHz, DMSO-d$_6$) δ ppm 2.68 (s, 3H), 5.90 (s, 2H), 7.08-7.13 (m, 1H), 7.51-7.58 (m, 2H), 7.76-7.81 (m, 1H), 7.84 (d, J=9.2 Hz, 1H), 8.00 (d, J=8.0 Hz, 1H), 8.06 (s, 1H), 8.15 (d, J=2.2 Hz, 1H), 11.93 (br s, 1H).

Example 24

N-(6-(6-chloro-5-(methylsulfonamido)pyridin-3-yl)-3-(4-fluoro-3-(morpholine-4-carbonyl)phenyl)imidazo[1,2-b]pyridazin-2-yl)acetamide (TFA Salt)

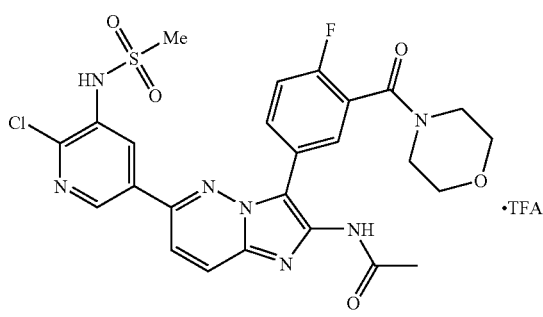

Following the procedure described for N-(6-(6-chloro-5-(methylsulfonamido)pyridin-3-yl)-3-(3-fluorophenyl)imidazo[1,2-b]pyridazin-2-yl)acetamide (TFA salt) (Example 22), N-(6-(6-chloro-5-(methylsulfonamido)pyridin-3-yl)-3-iodoimidazo[1,2-b]pyridazin-2-yl)acetamide (0.0650 g, 0.128 mmol) (Example 21) was reacted with 4-fluoro-3-(morpholine-4-carbonyl)phenylboronic acid (0.0390 g, 0.154 mmol, Combi-Blocks, San Diego, Calif.) at 90° C. for 3 h to afford the title compound as a yellow solid (0.058 g, 64%). MS (ESI, positive ion) m/z: 588 (M−TFA+1). $^1$H NMR (400 MHz, DMSO-d$_6$) δ ppm 2.03 (s, 3H), 3.20 (s, 3H), 3.32 (s, 2H), 3.51-3.58 (m, 2H), 3.67 (br s, 4H), 7.45 (t, J=9.1 Hz, 1H), 7.80 (d, J=4.9 Hz, 1H), 7.99 (d, J=9.6 Hz, 1H), 8.04-8.09 (m, 1H), 8.31 (d, J=9.4 Hz, 1H), 8.48 (d, J=2.3 Hz, 1H), 8.93 (d, J=2.2 Hz, 1H), 9.93 (s, 1H), 10.28 (br s, 1H).

Example 25

5-(2-Amino-6-(6-chloro-5-(methylsulfonamido)pyridin-3-yl)imidazo[1,2-b]pyridazin-3-yl)-2-fluorobenzoic acid (TFA Salt)

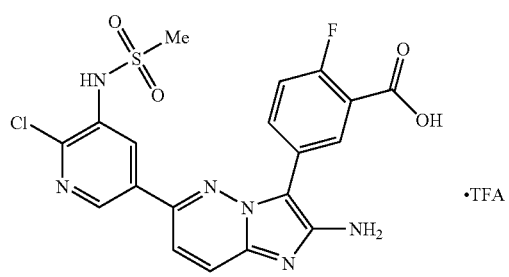

Following the procedure described for N-(5-(2-amino-3-(3-fluorophenyl)imidazo[1,2-b]pyridazin-6-yl)-2-chloropyridin-3-yl)methanesulfonamide (Example 23), N-(6-(6-chloro-5-(methylsulfonamido)pyridin-3-yl)-3-(4-fluoro-3-(morpholine-4-carbonyl)phenyl)imidazo[1,2-b]pyridazin-2-yl)acetamide (TFA salt) (Example 24) (0.016 g, 0.023 mmol) was treated with sodium hydroxide (0.100 mL, 1.0 mmol, 10 M) and purified by preparative HPLC (Phenomenex Gemini 5 micron (Phenomenex, Torrance, Calif.), C18, 100×30 mm, 5 to 85% CH$_3$CN(0.1% TFA)/H$_2$O(0.1% TFA) over 20 min then 100% CH$_3$CN(0.1% TFA) for 3 minutes at 20 mL/min) with the fractions containing suspected product concentrated to afford the title compound as a yellow solid (3.6 mg, 27%). MS (ESI, positive ion) m/z: 477 (M−TFA+1). $^1$H NMR (400 MHz, DMSO-d$_6$) δ ppm 3.19 (s, 3H), 6.00 (br s, 2H), 7.40-7.45 (m, 1H), 7.77 (d, J=9.2 Hz, 1H), 7.91 (d, J=9.2 Hz, 1H), 8.23-8.28 (m, 1H), 8.45 (d, J=2.0 Hz, 1H), 8.47-8.50 (m, 1H), 8.93 (d, J=2.0 Hz, 1H), 9.85 (s, 1H), 13.28 (br s, 1H).

Example 26

N-(6-(6-Chloro-5-(methylsulfonamido)pyridin-3-yl)-3-(pyridin-4-yl)imidazo[1,2-b]pyridazin-2-yl)acetamide (TFA Salt)

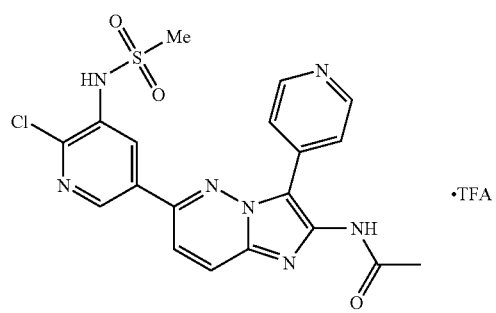

Following the procedure described for N-(6-(6-chloro-5-(methylsulfonamido)pyridin-3-yl)-3-(3-fluorophenyl)imidazo[1,2-b]pyridazin-2-yl)acetamide (TFA salt) (Example 22), N-(6-(6-chloro-5-(methylsulfonamido)pyridin-3-yl)-3-iodoimidazo[1,2-b]pyridazin-2-yl)acetamide (0.250 g, 0.493 mmol) (Example 21) was reacted with pyridine-4-boronic acid (0.0606 g, 0.493 mmol, Boron Molecular) and dichloro[1,1′-bis(diphenylphosphino)ferrocene]palladium(II)dichloromethane adduct (0.040 g, 0.049 mmol, Strem Chemical, Inc., Newburyport, Mass.) for 6 h at 90° C. to afford the title compound as a yellow solid (0.080 g, 28%). MS (ESI, positive ion) m/z: 458 (M−TFA+1). $^1$H NMR (400 MHz, DMSO-d$_6$) δ ppm 2.12 (s, 3H), 3.24 (s, 3H), 8.17 (d, J=9.6 Hz, 1H), 8.27 (d, J=6.1 Hz, 2H), 8.42 (d, J=9.4 Hz, 1H), 8.61 (d, J=2.0 Hz, 1H), 8.79 (d, J=6.1 Hz, 2H), 9.01 (d, J=2.0 Hz, 1H), 9.98 (br s, 1H), 10.76 (s, 1H).

Example 27

N-(5-(2-Amino-3-(pyridin-4-yl)imidazo[1,2-b]pyridazin-6-yl)-2-chloropyridin-3-yl)methanesulfonamide

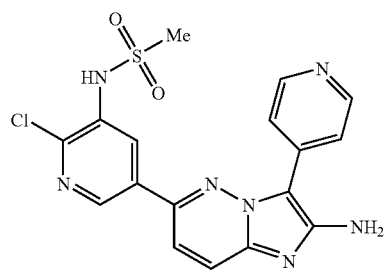

Following the procedure described for N-(5-(2-amino-3-(3-fluorophenyl)imidazo[1,2-b]pyridazin-6-yl)-2-chloropyridin-3-yl)methanesulfonamide (Example 23), N-(6-(6-chloro-5-(methylsulfonamido)pyridin-3-yl)-3-(pyridin-4-yl)imidazo[1,2-b]pyridazin-2-yl)acetamide (TFA salt) (Example 26) (0.040 g, 0.070 mmol) was reacted with sodium hydroxide (0.200 mL, 2.0 mmol, 10 M) at 50° C. for 28 h to afford the title compound as a yellow solid (0.0210 g, 72%). MS (ESI, positive ion) m/z: 416 (M+1). $^1$H NMR (400 MHz, DMSO-$d_6$) δ ppm 3.20 (s, 3H), 6.26 (s, 2H), 7.88 (d, J=9.2 Hz, 1H), 7.95 (d, J=9.2 Hz, 1H), 8.08 (d, J=6.1 Hz, 2H), 8.57 (d, J=2.2 Hz, 1H), 8.63 (d, J=6.1 Hz, 2H), 8.89 (br s, 1H), 9.94 (br s, 1H).

Example 28

N-(6-(6-Chloro-5-(4-fluorophenylsulfonamido)pyridin-3-yl)imidazo[1,2-a]pyridin-2-yl)acetamide

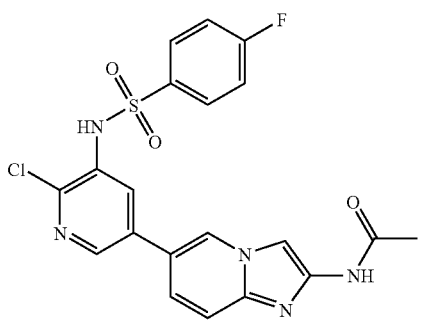

Step 1.
N-(5-bromopyridin-2-yl)-4-methylbenzenesulfonamide

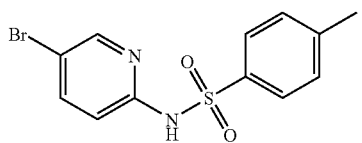

To a 500 mL round-bottomed flask was added 2-amino-5-bromopyridine (15.0 g, 86.7 mmol, Aldrich, St. Louis, Mo.), pyridine (150 mL, 1858 mmol) and finally para-toluenesulfonyl chloride (24.8 g, 130 mmol, Aldrich, St. Louis, Mo.) at rt. The mixture was stirred at 90° C. After 24 h, the mixture was allowed to cool to rt and then poured into water (600 mL). A precipitate formed and the mixture was stirred for 15 min and then filtered. The filtercake was washed with water and hexane and then dried under vacuum to afford the title compound as an off-white solid (27.8 g, 98%) that was carried on without further purification.

Step 2. 2-(5-bromo-2-(tosylimino)pyridin-1(2H)-yl)acetamide

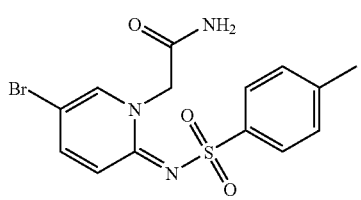

To a 250 mL round-bottomed flask was added N-(5-bromopyridin-2-yl)-4-methylbenzenesulfonamide (10.0 g, 31 mmol), DMF (60 mL), N,N-diisopropylethylamine (6.4 mL, 37 mmol) and 2-bromoacetamide (5.1 g, 37 mmol, Aldrich, St. Louis, Mo.). The mixture was stirred at 25° C. for 1 day. The mixture was poured into water (600 mL) and the solution was stirred for 1 h. The solution was filtered and the filtercake was washed with water and then dried in vacuo to afford the title compound as a white solid (10.2 g, 87%). MS (ESI, positive ion) m/z: 384 (M($^{79}$Br)+1).

Step 3. N-(6-bromoimidazo[1,2-a]pyridin-2-yl)-2,2,2-trifluoroacetamide

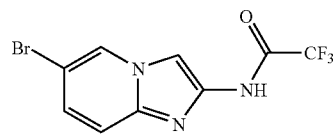

To a 250 mL round-bottomed flask equipped with a reflux condenser was added 2-(5-bromo-2-(4-methylphenylsulfonamido)pyridin-1(2H)-yl)acetamide (10.0 g, 26.0 mmol), 1,2-dichloroethane (150 mL) and finally trifluoroacetic anhydride (18.4 mL, 130 mmol). The mixture was stirred at 60° C. for 2 h. The solution was allowed to cool to rt and concentrated. The resulting solid was taken up in DCM (300 mL) and washed with 10% NaHCO$_3$ (2×100 mL). The aqueous washings were extracted with DCM (2×100 mL) and combined with the initial DCM solution. The combined solutions were washed with brine (100 mL), dried (Na$_2$SO$_4$) and concentrated to afford the title compound as a tan solid which was used without further purification (7.72 g, 96%).

Step 4. 6-bromoimidazo[1,2-a]pyridin-2-amine

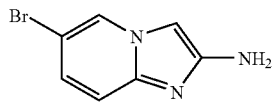

To a 250 mL round-bottomed flask was added N-(6-bromoH-imidazo[1,2-a]pyridin-2-yl)-2,2,2-trifluoroacetamide (3.50 g, 11 mmol), THF (15 mL), methanol (15 mL), water (15 mL) and potassium carbonate (16 g, 114 mmol). The mixture was stirred at 60° C. for 16 h. After cooling to rt, the mixture was poured into water (100 mL) and extracted with CH$_2$Cl$_2$ (4×75 mL). The combined extracts were washed with brine, dried (Na$_2$SO$_4$) and concentrated onto silica. Purification by silica gel chromatography (0.5 to 5.0% MeOH/CH$_2$Cl$_2$) afforded the title compound (1.01 g, 42%). MS (ESI, positive ion) m/z: 212 (M($^{79}$Br)+1).

Step 5.
N-(6-bromoimidazo[1,2-a]pyridin-2-yl)acetamide

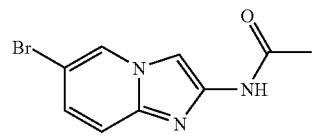

To a 100 mL round-bottomed flask was added 6-bromoH-imidazo[1,2-a]pyridin-2-amine (0.771 g, 3.6 mmol), DCM (30 mL), pyridine (0.44 mL, 5.5 mmol), acetic anhydride (0.41 mL, 4.4 mmol) and DMAP (0.0022 g, 0.018 mmol). The mixture was stirred at 35° C. for 3 h. After cooling to rt, the mixture was concentrated and then taken up in water (100 mL) and extracted with 25% iPrOH/CHCl$_3$ (3×75 mL). The combined extracts were washed with brine (75 mL), dried (Na₂SO₄) and concentrated in vacuo. The residue was dissolved in MeOH (2 M in NH₃)/CH₂Cl₂ and concentrated onto silica. Purification by silica gel chromatography MeOH (2 M in NH₃)/CH₂Cl₂) afforded the title compound as an orange solid (0.452 g, 49%). MS (ESI, positive ion) m/z: 254 (M(⁷⁹Br)+1).

Step 6. N-(6-(6-chloro-5-(4-fluorophenylsulfonamido)pyridin-3-yl)imidazo[1,2-a]pyridin-2-yl)acetamide

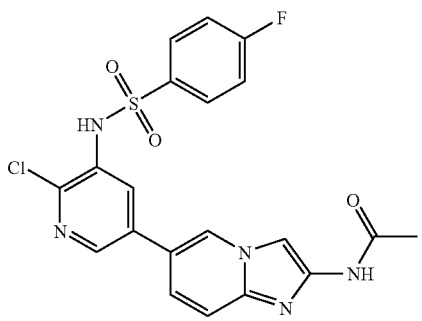

To a 10 mL round-bottomed flask was added N-(2-chloro-5-(4,4,5,5-tetramethyl-1,3,2-dioxaborolan-2-yl)pyridin-3-yl)-4-fluorobenzenesulfonamide (0.14 g, 0.35 mmol) (Step 2, Example 48), N-(6-bromoH-imidazo[1,2-a]pyridin-2-yl)acetamide (0.080 g, 0.31 mmol), DMSO (3.0 mL), and aq sodium carbonate (0.94 mL, 1.9 mmol, 2 M). The mixture was carefully evacuated and backfilled with N₂. To the mixture was added trans-dichlorobis(triphenylphosphine)palladium(II) (0.022 g, 0.031 mmol, Strem Chemical, Inc., Newburyport, Mass.). Again, the mixture was carefully evacuated and backfilled with N₂. The mixture was stirred at 95° C. for 1 h. After cooling to rt, the mixture was poured into a solution of pH 5 buffer (25 mL, 3 M sodium acetate pH adjusted to 4.8 (Teknova, Hollister, Mass.)) and water (25 mL). The solution was filtered and the filtercake was washed with water (2×), CH₂Cl₂ (2×) and then dried under vacuum to afford the title compound as a tan solid (0.102 g, 70%). MS (ESI, positive ion) m/z: 460 (M+1). ¹H NMR (400 MHz, DMSO-d₆) δ ppm 2.08 (s, 3H), 7.16-7.23 (m, 3H), 7.48 (d, J=9.2 Hz, 1H), 7.65 (d, J=2.3 Hz, 1H), 7.73 (d, J=2.2 Hz, 1H), 7.78-7.82 (m, 2H), 8.14 (s, 1H), 8.72 (s, 1H), 10.69 (s, 1H), 11.95 (br s, 1H).

Example 29

N-(5-(2-Aminoimidazo[1,2-a]pyridin-6-yl)-2-chloropyridin-3-yl)-4-fluorobenzenesulfonamide

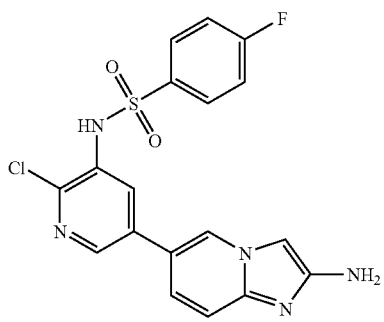

To a 10 mL round-bottomed flask was added N-(2-chloro-5-(4,4,5,5-tetramethyl-1,3,2-dioxaborolan-2-yl)pyridin-3-yl)-4-fluorobenzenesulfonamide (0.150 g, 0.363 mmol) (Step 2, Example 48), 6-bromoH-imidazo[1,2-a]pyridin-2-amine (0.0700 g, 0.330 mmol) (Step 4, Example 28), DMSO (3.00 mL), and sodium carbonate (0.990 mL, 1.98 mmol, 2 M). The mixture was carefully evacuated and backfilled with N₂. To the mixture was added trans-dichlorobis(triphenylphosphine)palladium(II) (0.0232 g, 0.0330 mmol, Strem Chemical, Inc., Newburyport, Mass.). Again, the mixture was carefully evacuated and backfilled with N₂. The mixture was stirred at 95° C. for 3 h. After cooling to rt, the mixture was poured into pH 4.8 buffer (3 M sodium acetate solution pH adjusted to 4.8, Teknova, Hollister, Mass.) diluted with water. The solution was filtered and the filtercake was washed with water and then 50% CH₂Cl₂/hexane. The aqueous washings were extracted with 25% iPrOH/CHCl₃ and the extracts were combined with the filtercake. The combined material was concentrated to remove all of the solvents and the residue was taken up in MeOH/CH₂Cl₂ and concentrated onto silica. Purification by silica gel chromatography (2.0 to 9.0% MeOH/CH₂Cl₂) afforded the title compound as a yellow solid (0.0307 g, 22%). MS (ESI, positive ion) m/z: 418 (M+1). ¹H NMR (400 MHz, DMSO-d₆) δ ppm 7.08 (s, 1H), 7.34 (br s, 3H), 7.38-7.44 (m, 3H), 7.60 (br s, 2H), 7.78-7.84 (m, 3H), 7.97 (d, J=2.2 Hz, 1H), 8.49 (d, J=2.0 Hz, 1H), 8.77 (s, 1H).

Example 30

N-(5-(6-Chloro-5-(4-fluorophenylsulfonamido)pyridin-3-yl)-1H-benzo[d]imidazol-2-yl)acetamide

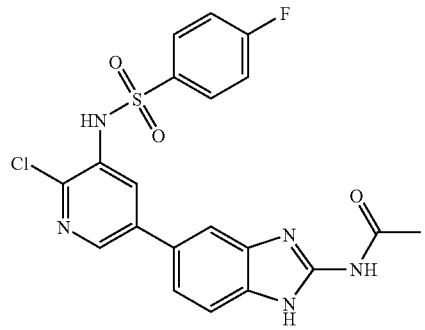

Step 1.
N-(6-bromo-1H-benzo[d]imidazol-2-yl)acetamide

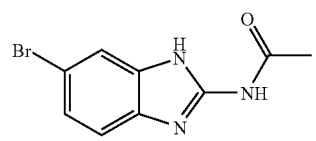

To a 250 mL round-bottomed flask was added 6-bromo-1H-benzo[d]imidazol-2-amine (2.00 g, 9.43 mmol, Carbocore, The Woodlands, Tex.), DCM (100 mL), pyridine (1.0 mL, 12.3 mmol) and acetic anhydride (0.979 mL, 10.4 mmol). The mixture was stirred at 25° C. for 18 h. The solution was concentrated and then diluted with 10% MeOH (2M in NH₃)/CH₂Cl₂ until homogeneous and then the solution was concentrated onto silica. Purification by silica gel chromatography (0.5 to 5.0% MeOH (2 M in NH₃)/CH₂Cl₂) afforded the title compound as a white solid (0.676 g, 28%). MS (ESI, positive ion) m/z: 254 (M(⁷⁹Br)+1).

Step 2. N-(5-(6-chloro-5-(4-fluorophenylsulfona-mido)pyridin-3-yl)-1H-benzo[d]imidazol-2-yl)aceta-mide

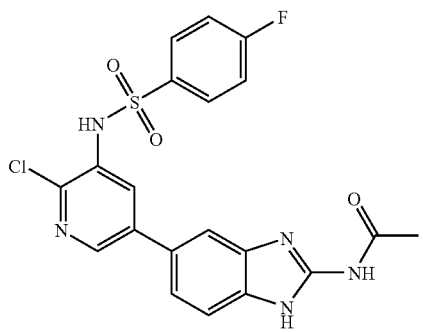

To a 25 mL round-bottomed flask was added N-(5-bromo-2-chloropyridin-3-yl)-4-fluorobenzenesulfonamide (0.150 g, 0.410 mmol) (Step 1, Example 48), bis(pinacolato)diboron (0.156 g, 0.615 mmol, Aldrich, St, Louis, Mo.), potassium acetate (0.161 g, 1.64 mmol) and 1,4-dioxane (4.0 mL). The mixture was carefully evacuated and backfilled with $N_2$. To the solution was added dichloro[1,1'-bis(diphenylphosphino)ferrocene]palladium(II)dichloromethane adduct (0.030 g, 0.041 mmol, Strem Chemical, Inc., Newburyport, Mass.). The mixture was carefully evacuated and backfilled with $N_2$ again. The mixture was stirred at 90° C. for 6 h. The reaction mixture was cooled to rt and to it was added DMF (4.0 mL), N-(5-bromo-1H-benzo[d]imidazol-2-yl)acetamide (0.080 g, 0.31 mmol) and aq sodium carbonate (0.79 mL, 1.6 mmol, 2 M). The mixture was carefully evacuated and backfilled with $N_2$. To the mixture was added trans-dichlorobis(triphenylphosphine)palladium(II) (0.022 g, 0.031 mmol, Strem Chemical, Inc., Newburyport, Mass.). Once again the mixture was carefully evacuated and backfilled with $N_2$. The mixture was stirred at 90° C. for 16 h and then, after cooling to rt, was poured into aq. NaCl (100 mL) and extracted with 25% iPrOH/CHCl$_3$ (3×75 mL). The combined extracts were dried (Na$_2$SO$_4$) and concentrated. The material was then taken up in MeOH/CH$_2$Cl$_2$ and concentrated onto silica. Purification by silica gel chromatography (0.5 to 5.0% MeOH (2 M in NH$_3$)/CH$_2$Cl$_2$) afforded the title compound as a white solid (0.0217 g, 15%). MS (ESI, positive ion) m/z: 460 (M+1). $^1$H NMR (400 MHz, DMSO-d$_6$) δ ppm 2.18 (s, 3H), 7.37 (br s, 1H), 7.44 (t, J=8.8 Hz, 2H), 7.56 (br s, 1H), 7.70 (br s, 1H), 7.83 (dd, J=8.8, 5.3 Hz, 2H), 7.91 (s, 1H), 8.56 (br s, 1H), 10.44 (br s, 1H), 11.62 (br s, 1H), 12.16 (br s, 1H).

Example 31 and Example 32

N-(5-(2-Amino-1-(pyridin-2-yl)-1H-benzo[d]imidazol-6-yl)-2-chloropyridin-3-yl)-4-fluorobenzenesulfonamide (formic acid salt) and N-(6-(6-Chloro-5-(4-fluorophenylsulfonamido)pyridin-3-yl)-1-(pyridin-2-yl)-1H-benzo[d]imidazol-2-yl)acetamide

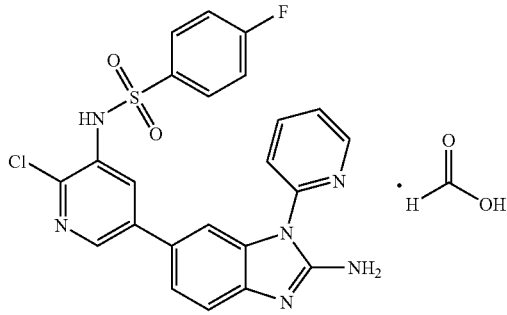

Step 1. 6-bromo-1-(pyridin-2-yl)-1H-benzo[d]imida-zol-2-amine

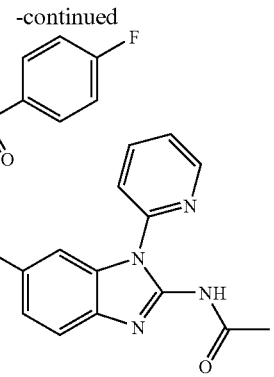

To two 10-20 mL microwave vials was added 5-bromo-1H-benzo[d]imidazol-2-amine (3.00 g, 14.1 mmol, Carbocore, The Woodlands, Tex.), N,N-dimethylacetamide (20 mL), 2-fluoropyridine (1.46 mL, 17.0 mmol, Aldrich, St. Louis, Mo.) and cesium carbonate (7.84 g, 24.1 mmol). (One-half of the material in each vial, ie 1.5 g of the bromide in each vial.) The mixture was heated at 150° C. for 140 min in the microwave. After cooling to rt, the combined reaction mixtures were poured into water (400 mL) and then extracted with EtOAc/hexane (80:20) (3×150 mL). The combined extracts were washed with water (3×100 mL) and brine (100 mL) and then dried (Na$_2$SO$_4$) and concentrated onto silica. Purification by silica gel chromatography (0.5 to 3.8% MeOH (2 M in NH$_3$)/CH$_2$Cl$_2$) afforded the title compound (1.06 g, 26%). MS (ESI, positive ion) m/z: 289 (M($^{79}$Br)+1).

Step 2. N-(6-bromo-1-(pyridin-2-yl)-1H-benzo[d]imidazol-2-yl)acetamide

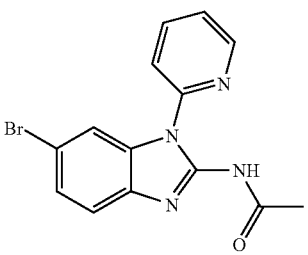

To a 250 mL round-bottomed flask was added 6-bromo-1-(pyridin-2-yl)-1H-benzo[d]imidazol-2-amine (1.00 g, 3.46 mmol), dichloromethane (35 mL), pyridine (0.419 mL, 5.19 mmol), acetic anhydride (0.343 mL, 3.63 mmol) and DMAP (0.0042 g, 0.035 mmol). The mixture was stirred at 25° C. for 2.5 days. The mixture was concentrated and taken up in MeOH/CH$_2$Cl$_2$ and then concentrated onto silica. Purification by silica gel chromatography (0.5 to 4.0% MeOH (2 M in NH$_3$)/CH$_2$Cl$_2$) afforded the title compound as a pink solid (0.673 g, 58%). MS (ESI, positive ion) m/z: 331 (M($^{79}$Br)+1).

Step 3

N-(5-(2-amino-1-(pyridin-2-yl)-1H-benzo[d]imidazol-6-yl)-2-chloropyridin-3-yl)-4-fluorobenzenesulfonamide (formic acid salt) and N-(6-(6-chloro-5-(4-fluorophenylsulfonamido)pyridin-3-yl)-1-(pyridin-2-yl)-1H-benzo[d]imidazol-2-yl)acetamide

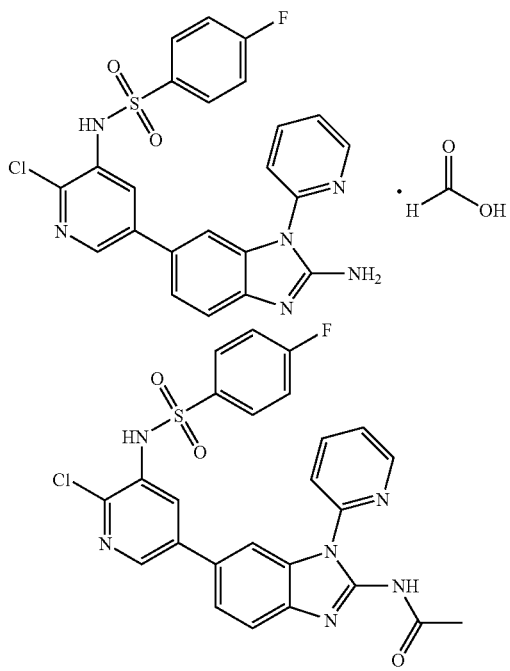

To a 5 mL vial was added N-(6-bromo-1-(pyridin-2-yl)-1H-benzo[d]imidazol-2-yl)acetamide (0.10 g, 0.30 mmol), N-(2-chloro-5-(4,4,5,5-tetramethyl-1,3,2-dioxaborolan-2-yl)pyridin-3-yl)-4-fluorobenzenesulfonamide (0.15 g, 0.36 mmol) (Step 2, Example 48), DMF (2.0 mL) and aq potassium carbonate (0.76 mL, 1.5 mmol, 2 M). The mixture was carefully evacuated and backfilled with N$_2$. To the mixture was added trans-dichlorobis(triphenylphosphine)palladium (II) (0.021 g, 0.030 mmol). Again, the mixture was carefully evacuated and backfilled with N$_2$. The mixture was heated at 100° C. for 18 h. After cooling to rt, the mixture was poured into water and was extracted with 25% iPrOH/CHCl$_3$. The combined extracts were washed with brine and then dried (Na$_2$SO$_4$) and concentrated. The residue was taken up in MeOH/CH$_2$Cl$_2$ and concentrated onto silica. Purification by silica gel chromatography (0.5 to 7.0% MeOH/CH$_2$Cl$_2$) followed by further purification by Preparative-HPLC (Phenomenex Luna C8 100×21.2 mm, 5 micron) (Phenomenex, Torrance, Calif.) 2 to 100% CH$_3$CN(0.1% formic acid)/H$_2$O (0.1% formic acid) over 15 min then 100% CH$_3$CN(0.1% formic acid) for 5 minutes at 20 mL/min) with the fractions containing suspected products concentrated:

N-(5-(2-amino-3-(pyridin-2-yl)-3H-benzo[d]imidazol-5-yl)-2-chloropyridin-3-yl)-4-fluorobenzenesulfonamide (formic acid salt) (0.0218 g, 14%) (Example 31) MS (ESI, positive ion) m/z: 495 (M+1). $^1$H NMR (400 MHz, DMSO-d$_6$) δ ppm 7.08 (s, 2H), 7.33-7.41 (m, 4H), 7.49-7.55 (m, 2H), 7.77-7.86 (m, 4H), 8.10-8.15 (m, 2H), 8.51 (s, 1H), 8.68 (d, J=4.7, Hz, 1H), 10.52 (br s, 1H), 12.72 (br s, 1H).

N-(6-(6-chloro-5-(4-fluorophenylsulfonamido)pyridin-3-yl)-1-(pyridin-2-yl)-1H-benzo[d]imidazol-2-yl)acetamide (0.0103 g, 6.4%) (Example 32). MS (ESI, positive ion) m/z: 537 (M+1). $^1$H NMR (400 MHz, DMSO-d$_6$) δ ppm 2.03 (s, 3H), 7.38 (t, J=8.8 Hz, 2H), 7.51-7.58 (m, 2H), 7.69-7.75 (m, 2H), 7.75-7.82 (m, 3H), 7.88 (d, J=1.6 Hz, 1H), 8.11 (td, J=7.8, 1.7 Hz, 1H), 8.53 (s, 1H), 8.67 (d, J=3.3 Hz, 1H), 10.46 (br s, 1H), 10.85 (br s, 1H).

Example 33

N-(6-(6-Chloro-5-(3-(difluoromethoxy)phenylsulfonamido)pyridin-3-yl)imidazo[1,2-b]pyridazin-2-yl)acetamide

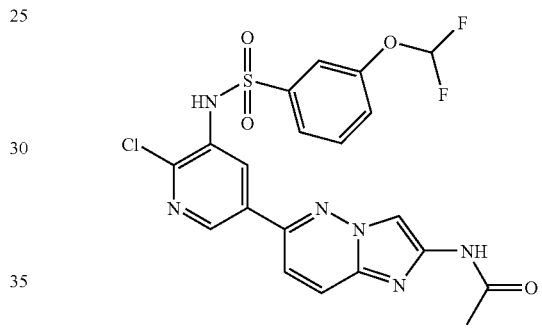

Step 1. N-(5-Bromo-2-chloropyridin-3-yl)-3-(difluoromethoxy)benzenesulfonamide

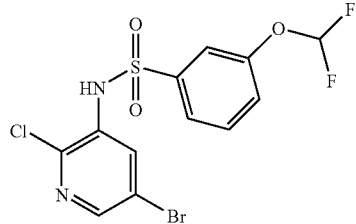

A round bottomed flask was charged with 3-amino-5-bromo-2-chloropyridine (1.5 g, 7 mmol, Asymchem Laboratories, Inc. Morrisville, N.C.) and pyridine (20 mL). To this solution, 3-(difluoromethoxy)benzenesulfonyl chloride (2 mL, 8 mmol, Sigma-Aldrich Corporation, St. Louis, Mo.) was added dropwise and the solution was stirred at 25° C. for 18 h. The mixture was concentrated in vacuum and the residue was suspended in H$_2$O. The white solid was collected by filtration and then suspended in methanol (50 mL). To this suspension, potassium carbonate (1.9 g, 14 mmol) was added, and the mixture was stirred at 25° C. for 20 h. The suspension was filtered and the filtrate was concentrated in vacuo. Purification by silica gel chromatography (10-50% EtOAC/Hexane) afforded the title compound (1.4 g, 47% yield) as a white solid. MS (ESI positive ion) m/z: 415 (M+1).

Step 2. N-(2-Chloro-5-(4,4,5,5-tetramethyl-1,3,2-dioxaborolan-2-yl)pyridin-3-yl)-3-(difluoromethoxy) benzenesulfonamide

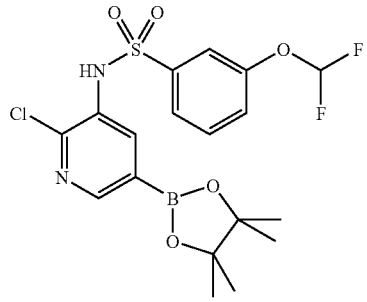

To a 250 mL, round-bottomed flask was added N-(5-bromo-2-chloropyridin-3-yl)-3-(difluoromethoxy)benzenesulfonamide (1.4 g, 3.4 mmol), bis(pinacolato)diboron (1.0 g, 4.1 mmol), 1,1'-bis(diphenylphosphino)ferrocene-palladium dichloride (0.17 g, 0.24 mmol, Strem Chemical, Inc., Newburyport, Mass.), potassium acetate (0.94 g, 6.8 mmol), and dioxane (20 mL). The reaction mixture was stirred and heated at 100° C. for 3 h. The mixture was diluted with EtOAc, washed by $H_2O$ and brine, dried over $MgSO_4$, concentrated in high vacuum to provide the title compound, which was taken on to the next step without further purification. MS (ESI positive ion) m/z: 379 (M+1).

Step 3. N-(6-(6-Chloro-5-(3-(difluoromethoxy)phenylsulfonamido)pyridin-3-yl)imidazo[1,2-b]pyridazin-2-yl)acetamide

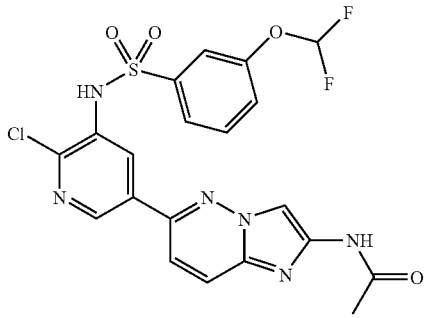

A glass microwave reaction vessel was charged with N-(2-chloro-5-(4,4,5,5-tetramethyl-1,3,2-dioxaborolan-2-yl)pyridin-3-yl)-3-(difluoromethoxy)benzenesulfonamide (1.1 g, 2.4 mmol), N-(6-chloroimidazo[1,2-b]pyridazin-2-yl)acetamide (0.25 g, 1.2 mmol), 1,1'-bis(diphenylphosphino)ferrocene-palladium dichloride (87 mg, 0.012 mmol, Strem Chemical, Inc., Newburyport, Mass.), sodium carbonate (0.25 g, 2.4 mmol), and dioxane-$H_2O$ (5 mL, 4:1). Ar was bubbled in the solution for 1 minute. The reaction mixture was sealed and heated at 100° C. for 2 h and then was concentrated in vacuo. Purification by silica gel chromatography (5-20% MeOH/$CH_2Cl_2$), followed by further purification by preparative HPLC (Phenomenex Synergi 4μ MAX-RP 150× 21.2 mm, 30 to 80% $CH_3CN/H_2O$, 0.1% TFA, over 12 min) (Phenomenex, Torrance, Calif.) provided the title compound (0.18 g, 30% yield) as a tan solid. MS (ESI positive ion) m/z: 524 (M+1). $^1$H NMR (400 MHz, MeOH-d): δ ppm 2.22 (s, 3H), 6.88 (t, J=73.07 Hz, 1H), 7.43 (dd, J=8.12, 1.86 Hz, 1H), 7.54-7.62 (m, 2H), 7.63-7.68 (m, 1H), 7.74 (d, J=9.59 Hz, 1H), 7.98 (d, J=9.59 Hz, 1H), 8.44 (s, 1H), 8.57 (d, J=2.15 Hz, 1H), 8.82 (d, J=2.35 Hz, 1H).

Example 34

N-(6-(6-Chloro-5-(2-chloro-6-methylphenylsulfonamido)pyridin-3-yl)imidazo[1,2-b]pyridazin-2-yl) acetamide

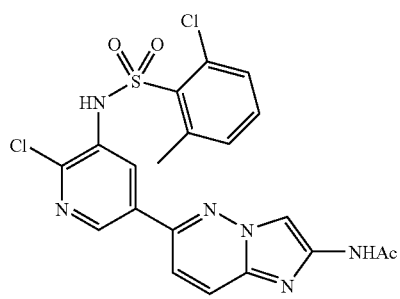

Step 1. 2-Chloro-5-(4,4,5,5-tetramethyl-1,3,2-dioxaborolan-2-yl)pyridin-3-amine

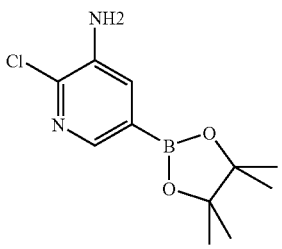

To a 100 mL, round-bottomed flask was added 5-bromo-2-chloropyridin-3-amine (2 g, 10 mmol, Asymchem Laboratories, Morrisville, N.C.), 4,4,5,5-tetramethyl-2-(4,4,5,5-tetramethyl-1,3,2-dioxaborolan-2-yl)-1,3,2-dioxaborolane (2 g, 10 mmol, Aldrich, St. Louis, Mo.), potassium acetate (0.9 g, 10 mmol), 1,1'-bis(diphenylphosphino)ferrocene-palladium dichloride (7 g, 10 mmol, Strem Chemical, Inc., Newburyport, Mass.), and dioxane (20 mL). The mixture was degassed by Ar for 1 minute, then stirred under $N_2$ protection at 90° C. for 4 h. The black suspension was filtered through a celite pad, the filtercake was washed with MeOH-DCM (50%). The filtrate was concentrated in vacuum. The resulted residue was treated with ether and filtered again. The filtrate was concentrated in vacuo. Purification by silica gel chromatography (20 to 50% (10% MeOH/$CH_2Cl_2$)-hexane) and later by recrystallized from methanol-hexane provided 2-chloro-5-(4,4,5-trimethyl-1,3,2-dioxaborolan-2-yl)pyridin-3-amine as a white solid. MS (ESI positive ion) m/z: 173 and 208 (M+1). $^1$H NMR (400 MHz, DMSO-$d_6$): δ ppm 1.29 (s, 12H), 5.58 (s, 2H), 7.40 (d, J=1.76 Hz, 1H), 7.76 (d, J=1.76 Hz, 1H).

Step 2. N-(6-(5-Amino-6-chloropyridin-3-yl)imidazo[1,2-b]pyridazin-2-yl)acetamide

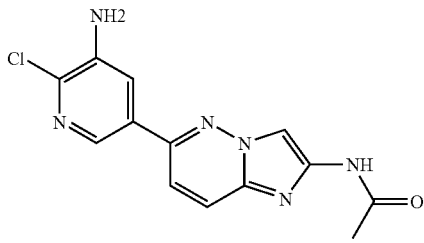

A glass microwave reaction vessel was charged with N-(6-chloroimidazo[1,2-b]pyridazin-2-yl)acetamide (0.05 g, 0.2 mmol, Aurigene, Bangalore, India), 2-chloro-5-(4,4,5,5-tetramethyl-1,3-dioxolan-2-yl)pyridin-3-amine from Step 1 (0.07 g, 0.3 mmol), 1,1'-bis(diphenylphosphino)ferrocenepalladium dichloride (0.01 g, 0.02 mmol), sodium carbonate (0.05 g, 0.5 mmol), and dioxane-$H_2O$ (4:1, 2 mL). Ar was bubbled in for 1 minute. The reaction mixture was sealed and heated at 100° C. for 2 h before cooled down to room temperature. The mixture was filtered through a Celite® (diatomaceous earth) pad, the filtercake was washed with MeOH-DCM (50%), and the filtrate was concentrated in vacuo. Purification by silica gel chromatography (10 to 50% MeOH/$CH_2Cl_2$) provided N-(6-(5-amino-6-chloropyridin-3-yl)imidazo[1,2-b]pyridazin-2-yl)acetamide (0.03 g, 42% yield) as a white solid. MS (ESI positive ion) m/z: 303 (M+1). $^1$H NMR (400 MHz, DMSO-$d_6$): δ ppm 2.11 (s, 3H), 5.84 (s, 2H), 7.72 (d, J=9.39 Hz, 1H), 7.77 (d, J=2.15 Hz, 1H), 8.08 (d, J=9.39 Hz, 1H), 8.23 (d, J=2.15 Hz, 1H), 8.28 (s, 1H), 10.93 (s, 1H).

Step 3. N-(6-(6-Chloro-5-(2-chloro-6-methylphenylsulfonamido)pyridin-3-yl)imidazo[1,2-b]pyridazin-2-yl)acetamide

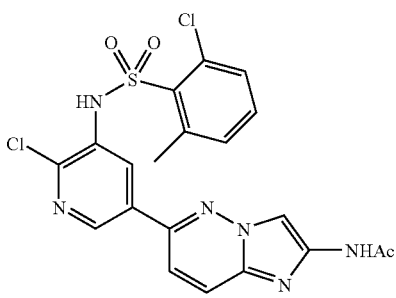

To a 50 mL, round-bottomed flask was added N-(6-(5-amino-6-chloropyridin-3-yl)imidazo[1,2-b]pyridazin-2-yl)acetamide from Step 2 (30 mg, 99 μmol), 2-chloro-6-methylbenzenesulfonyl chloride (149 μl, 661 μmol, Alfa Aesar, Ward Hill, Mass.), and pyridine (5 mL). The reaction mixture was stirred at 25° C. for 15 h and concentrated in high vacuum. Purification by silica gel chromatography (5 to 20% MeOH/$CH_2Cl_2$ provided N-(6-(6-chloro-5-(2-chloro-6-methylphenylsulfonamido)pyridin-3-yl)imidazo[1,2-b]pyridazin-2-yl)acetamide (20 mg, 41% yield) as an off-white solid. MS (ESI positive ion) m/z: 491 (M+1). $^1$H NMR (400 MHz, DMSO-$d_6$): δ ppm 2.13 (s, 3H), 2.59 (s, 3H), 7.37 (d, J=7.03 Hz, 1H), 7.50 (q, J=7.53 Hz, 2H), 7.83 (d, J=9.54 Hz, 1H), 8.13 (d, J=9.03 Hz, 1H), 8.31 (s, 1H), 8.38 (s, 1H), 8.91 (s, 1H), 10.71 (s, 1H), 10.99 (s, 1H).

Example 35

N-(6-(6-Chloro-5-(4-(2-hydroxypropan-2-yl)phenylsulfonamido)pyridin-3-yl)imidazo[1,2-b]pyridazin-2-yl)acetamide

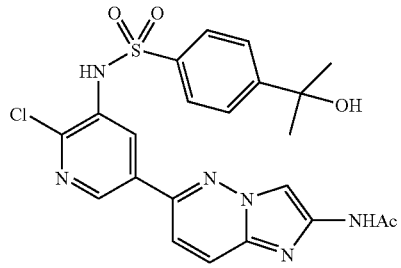

Step 1. 4-acetyl-N-(5-Bromo-2-chloropyridin-3-yl)benzenesulfonamide

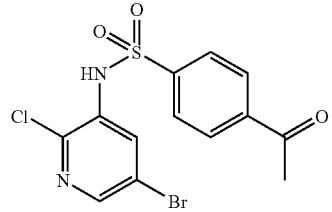

To a 150 mL, round-bottomed flask was added 3-amino-5-bromo-2-chloropyridine (1 g, 5 mmol, Asymchem Laboratories, Morrisville, N.C.) and pyridine(10 mL). To this solution, 4-acetylbenzenesulfonyl chloride (2 g, 10 mmol, Sigma-Aldrich Corporation, St. Louis, Mo.) was added, the mixture was stirred at 25° C. for 15 h and at 100° C. for additional 2 h. The mixture was concentrated in high vacuo. The result brown oil was suspended in methanol (200 mL)-$H_2O$ (5 mL). To this suspension, $K_2CO_3$ (2 g, 14.4 mmol) was added and the mixture was stirred at 25° C. for 15 h. The methanol was removed in vacuum; the residue was treated with $H_2O$. Filtration provided 4-acetyl-N-(5-bromo-2-chloropyridin-3-yl)benzenesulfonamide (0.5 g) as a brown solid. The filtrate was extracted by MeOH-DCM (10%) to provide additional 1.1 g of 4-acetyl-N-(5-bromo-2-chloropyridin-3-yl)benzenesulfonamide as a white solid. MS (ESI positive ion) m/z: 391 (M+1). $^1$H NMR (400 MHz, DMSO-$d_6$): δ ppm 2.57 (s, 3H), 7.51-7.56 (m, 2H), 7.81 (d, J=8.41 Hz, 2H), 7.98 (d, J=8.41 Hz, 2H).

Step 2. N-(5-Bromo-2-chloropyridin-3-yl)-4-(2-hydroxypropan-2-yl)benzenesulfonamide

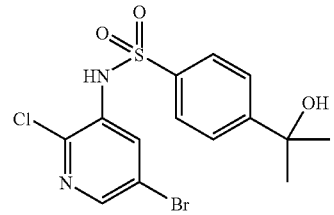

To a 100 mL, round-bottomed flask was added 4-acetyl-N-(5-bromo-2-chloropyridin-3-yl)benzenesulfonamide from Step 1 (250 mg, 642 μmol) and THF (10 mL). To this solution, methylmagnesium bromide (3.0 N, 4 mL, 12 mmol) was added in under $N_2$ protection. The suspension was stirred at 25° C. for 3 h. The mixture was quenched by aqueous saturated NH₄Cl. The aqueous part was extracted by 10% methanol-DCM (3×), and the combined organic was dried over MgSO₄, and concentrated in vacuo to provide the title product as a yellow oil (250 mg), which was taken on to the next step without further purification. MS (ESI positive ion) m/z: 407 (M+1).

Step 3. N-(6-(4,4,5,5-Tetramethyl-1,3,2-dioxaborolan-2-yl)imidazo[1,2-b]pyridazin-2-yl)acetamide

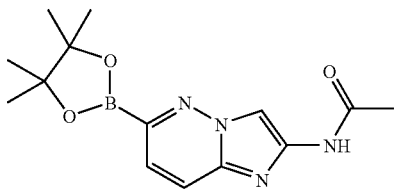

A glass microwave reaction vessel was charged with N-(6-chloroimidazo[1,2-b]pyridazin-2-yl)acetamide (0.6 g, 3 mmol, Aurigene, Bangalore, India), 4,4,5,5-tetramethyl-2-(4,4,5,5-tetramethyl-1,3,2-dioxaborolan-2-yl)-1,3,2-dioxaborolane (0.7 g, 3 mmol), potassium acetate (0.6 g, 6 mmol), 1,1'-bis(diphenylphosphino)ferrocene-palladium dichloride (0.1 g, 0.2 mmol, Strem Chemical, Inc., Newburyport, Mass.), and dioxane (5 mL). The mixture was sealed and heated at 100° C. for 3 h. After cooling to room temperature, the suspension was filtered through a Celite® (diatomaceous earth) cake, the filtercake was washed with MeOH-DCM (50%), and the filtrate was concentrated in vacuo. The result black oil was treated with ether to get the suspension. Filtration provided the title product (1.1 g) as a brown solid. MS (ESI positive ion) m/z: 221 (M+1).

Step 4. N-(6-(6-Chloro-5-(4-(2-hydroxypropan-2-yl)phenylsulfonamido)pyridin-3-yl)imidazo[1,2-b]pyridazin-2-yl)acetamide

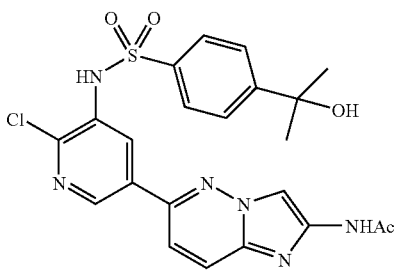

A glass microwave reaction vessel was charged with a mixture of N-(5-bromo-2-chloropyridin-3-yl)-4-(2-hydroxypropan-2-yl)benzenesulfonamide from Step 2 (250 mg, 616 µmol), N-(6-(4,4,5,5-tetramethyl-1,3,2-dioxaborolan-2-yl)imidazo[1,2-b]pyridazin-2-yl)acetamide from Step 3 (223 mg, 739 µmol), 1,1'-bis(diphenylphosphino)ferrocene-palladium dichloride (32 mg, 43 µmol, Strem Chemical, Inc., Newburyport, Mass.), sodium carbonate (131 mg, 1.2 mmol), and dioxane (3 mL). Ar was bubbled in for 1 minute, and the vessel was sealed and heated at 90° C. for 12 h. After cooled down to room temperature, the black suspension was filtered through a Celite® (diatomaceous earth) pad, and the filtercake was washed by MeOH-DCM (50%). The filtrate was concentrated in vacuo. Purification by silica gel chromatography (10 to 20% MeOH/CH₂Cl₂), followed by further purification by preparative HPLC (Phenomenex Synergi 4µ MAX-RP 150×21.2 mm, 40 to 90% CH₃CN/H₂O, 0.1% TFA, over 10 min) (Phenomenex, Torrance, Calif.) provided N-(6-(6-chloro-5-(4-(2-hydroxypropan-2-yl)phenylsulfonamido)pyridin-3-yl)imidazo[1,2-b]pyridazin-2-yl)acetamide (20 mg, 65% yield) as a yellow solid. MS (ESI positive ion) m/z: 501 (M+1). ¹H NMR (400 MHz, MeOH-d₆): δ ppm 1.51 (s, 6H), 2.22 (s, 3H), 7.66 (d, J=8.53 Hz, 2H), 7.71 (d, J=9.54 Hz, 1H), 7.78 (d, J=9.03 Hz, 2H), 7.98 (d, J=9.54 Hz, 1H), 8.43 (s, 1H), 8.56 (d, J=2.01 Hz, 1H), 8.78 (d, J=2.51 Hz, 1H).

Example 36

N-(5-(2-Aminoimidazo[1,2-b]pyridazin-6-yl)-2-chloropyridin-3-yl)-4-fluorobenzenesulfonamide

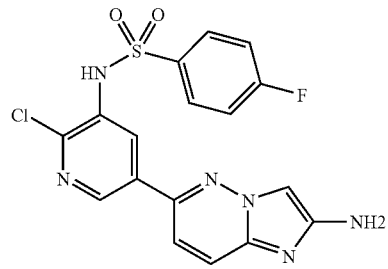

A 100 mL, round-bottomed flask was charged with N-(6-(6-chloro-5-(4-fluorophenylsulfonamido)pyridin-3-yl)imidazo[1,2-b]pyridazin-2-yl)acetamide (150 mg, Example 12) and methanol (10 mL)-NaOH (10 N, 5 mL). The mixture was refluxed for 2 h. After the solution was cooled to 0° C., 10 N HCl was added until pH=7. The crude product was concentrated in vacuo. Purification by silica gel chromatography (10 to 50% MeOH/CH₂Cl₂), followed by further purification by preparative HPLC (Phenomenex Synergi 4µ MAX-RP 150×21.2 mm, 40 to 90% CH₃CN/H₂O, 0.1% TFA, over 15 min) (Phenomenex, Torrance, Calif.) provided N-(5-(2-aminoimidazo[1,2-b]pyridazin-6-yl)-2-chloropyridin-3-yl)-4-fluorobenzenesulfonamide (20 mg, 5.0% yield) as a yellow solid. MS (ESI positive ion) m/z: 419 (M+1). ¹H NMR (400 MHz, DMSO-d₆): δ ppm 7.28 (t, J=8.80 Hz, 1H), 7.22-7.31 (m, 1H), 7.49 (s, 1H), 7.55 (d, J=9.19 Hz, 1H), 7.70-7.77 (m, 1H), 7.82-7.90 (m, 2H), 8.52 (d, J=2.15 Hz, 1H), 8.72 (d, J=2.15 Hz, 1H).

Example 37

Mixture of Isomers

N-(6-(6-chloro-5-(4-(1-(methylamino)ethyl)phenylsulfonamido)pyridin-3-yl)imidazo[1,2-b]pyridazin-2-yl)acetamide

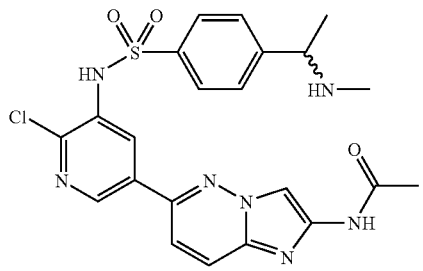

Step 1: 4-acetyl-N-(5-bromo-2-chloropyridin-3-yl)benzenesulfonamide

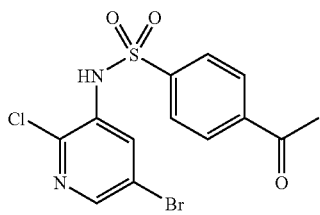

5-Bromo-2-chloropyridin-3-amine (1.535 g, 7.399 mmol, Asymchem Laboratories, Morrisville, N.C.) was dissolved in pyridine (20 mL), and 4-acetylbenzenesulfonyl chloride (2.436 g, 11.14 mmol) was added. The reaction flask was fit with a reflux condensor and placed in a preheated oil bath (110 C-115 C) and stirred under nitrogen for 2 hours. The reaction was then cooled to room temperature, concentrated, and poured into a biphasic solution of water (40 mL) and DCM (50 mL). The layers were separated, and the aqueous phase was extracted with DCM. The organic extracts were combined, dried over sodium sulfate, filtered, concentrated, and purified on a silica gel filter plug (DCM to 20:1 DCM/MeOH) to afford 4-acetyl-N-(5-bromo-2-chloropyridin-3-yl)benzenesulfonamide. MS (ESI positive ion) m/z: 389 (M+1, $^{79}$Br), 391 (M+1, $^{81}$Br). Calcd. for $C_{13}H_{10}BrClN_2O_3S$: 388 ($^{79}$Br), 390 ($^{81}$Br).

Step 2: N-(5-bromo-2-chloropyridin-3-yl)-4-(1-(methylamino)ethyl)benzenesulfonamide

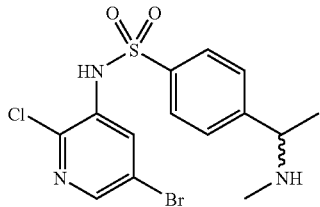

4-Acetyl-N-(5-bromo-2-chloropyridin-3-yl)benzenesulfonamide (540.2 mg, 1.386 mmol) was suspended in EtOH (5.0 mL) and titanium (IV) isopropoxide (0.82 mL, 2.8 mmol) and methylamine (4.2 mL, 8.4 mmol, 2.0 M in THF) were added. The reaction was stirred at room temperature overnight. Then, sodium borohydride (95.7 mg, 2.53 mmol) was added, and the reaction was stirred at room temperature for 30 minutes, and then water (10 mL) and ca. 7 N ammonia in MeOH (2.9 mL) were added simultaneously via syringe, causing precipitation. The reaction was stirred at room temperature, and after 45 minutes, the reaction contents were filtered. The solid was washed with EtOAc and MeOH, and the filtrate was concentrated and purified using silica gel with 20:1 DCM/MeOH to 3:1 DCM/2 N ammonia in MeOH to afford N-(5-bromo-2-chloropyridin-3-yl)-4-(1-(methylamino)ethyl)benzenesulfonamide (488 mg, 87% yield). MS (ESI positive ion) m/z: 404 (M+1, $^{79}$Br), 406 (M+1, $^{81}$Br). Calcd. for $C_{14}H_{15}BrClN_3O_2S$: 403 ($^{79}$Br), 405 ($^{81}$Br).

Step 3: N-(6-(4,4,5,5-tetramethyl-1,3,2-dioxaborolan-2-yl)imidazo[1,2-b]pyridazin-2-yl)acetamide

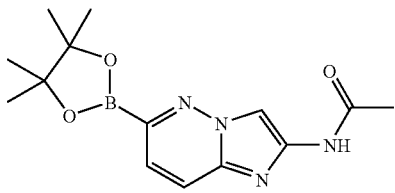

N-(6-chloroimidazo[1,2-b]pyridazin-2-yl)acetamide (750.9 mg, 3.565 mmol), bis(pinacolato)diboron (985 mg, 3.88 mmol), potassium acetate (798 mg, 8.13 mmol), and Pd(dppf)Cl$_2$*DCM complex (357 mg, 0.437 mmol) were suspended in 1,4-dioxane (10 mL), and the flask was fit with a reflux condensor and placed in a preheated oil bath (100 C) and stirred under nitrogen for 80 minutes. The reaction was cooled to room temperature and filtered through a pad of Celite® (diatomaceous earth), which was washed with 1:1 DCM/MeOH. The filtrate was concentrated, treated with Et$_2$O, and filtered. The solid was washed with Et$_2$O, collected, and dried under high vacuum to afford N-(6-(4,4,5,5-tetramethyl-1,3,2-dioxaborolan-2-yl)imidazo[1,2-b]pyridazin-2-yl)acetamide. MS (ESI positive ion) m/z: 221 (M+1). Calcd for $C_8H_9BN_4O_3$ (M–$C_6H_{10}$): 220.

Step 4: N-(6-(6-chloro-5-(4-(1-(methylamino)ethyl)phenylsulfonamido)pyridin-3-yl)imidazo[1,2-b]pyridazin-2-yl)acetamide

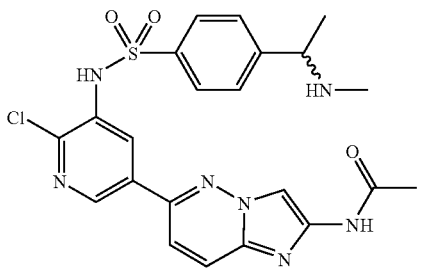

N-(5-bromo-2-chloropyridin-3-yl)-4-(1-(methylamino)ethyl)benzenesulfonamide (488 mg, 1.21 mmol), N-(6-(4,4,5,5-tetramethyl-1,3,2-dioxaborolan-2-yl)imidazo[1,2-b]pyridazin-2-yl)acetamide (590.6 mg, 1.955 mmol), potassium carbonate (600 mg, 4.34 mmol), and Pd(dppf)Cl$_2$*DCM complex (117.5 mg, 0.1439 mmol) were suspended in DME (8.0 mL) and water (2.0 mL). The reaction flask was fit with a reflux condensor and placed in a preheated oil bath (100 C) and stirred under nitrogen for 75 minutes. Then, the reaction was cooled to room temperature, and more N-(6-(4,4,5,5-tetramethyl-1,3,2-dioxaborolan-2-yl)imidazo[1,2-b]pyridazin-2-yl)acetamide (213 mg, 0.705 mmol) was added, and stirring was continued at 100 C. After another hour, the reaction was cooled to room temperature, diluted with DCM and MeOH, and filtered through a pad of Celite® (diatomaceous earth). The filtrate was concentrated and purified using silica gel on a filter (DCM to 50:1 to 20:1 to 5:1 to 3:1 DCM/2 N ammonia in MeOH). The fractions with product were collected, concentrated, treated with MeOH, and filtered. The solid was washed with MeOH, Et$_2$O, DCM, MeOH, and Et$_2$O. The solid was then collected and dried under high vacuum to afford N-(6-(6-chloro-5-(4-(1-(methylamino)ethyl)phenylsulfonamido)pyridin-3-yl)imidazo[1,2-b]pyridazin-2-yl)acetamide (253 mg, 42% yield) as a brown, amorphous solid. MS (ESI positive ion) m/z: 500 (M+1). Calcd for $C_{22}H_{22}ClN_7O_3S$: 499. 1H NMR (400 MHz, DMSO-d$_6$): δ ppm 10.93 (s, 1H), 8.25 (s, 1H), 8.12-8.06 (m, 2H), 8.03 (d, J=9.54 Hz, 1H), 7.85 (d, J=8.53 Hz, 2H), 7.56-7.47 (m, 4H), 4.32-4.20 (m, 1H), 2.40 (s, 3H), 2.11 (s, 3H), 1.48 (d, J=6.53 Hz, 3H).

About 200 mg of this material was purified on a chiral column using the following conditions to obtain the individual enantiomers: The sample was dissolved in 12 mL of DMSO and 12 drops (6 inch long Pasteur pipette) of diethylamine. The sample was injected onto a ADH (21×250 mm, 5 µm) column and eluted with supercritical CO$_2$ and ethanol (200 proof) with 0.2% Et$_2$NH (30% for 2 min and then increased up to 45% in 0.5 min, hold until the peaks eluted and re-equilibrate to 30%) at a flow rate of 50 mL/min (total). The outlet pressure was 100 bar, 0.3 mL/injection.

For the purposes of determining ee, analytical SFC was used with an ADH(4.6×250 mm, 5 um)×2 column and flow rate of 3 mL/minute (total, 50% ethanol with 0.2% Et$_2$NH, ambient temperature, 150 bar outlet pressure). Concentrated aliquots were analyzed.

The absolute stereochemistry of these two enantiomers was not determined.

Example 38 or Example 39

Separated Isomers

Enantiomer 1: MS (ESI positive ion) m/z: 500 (M+1). Calcd for C$_{22}$H$_{22}$ClN$_7$O$_3$S: 499. 1H NMR (400 MHz, DMSO-d$_6$): δ ppm 10.91 (s, 1H), 8.24 (s, 1H), 8.09-8.05 (m, 2H), 8.02 (d, J=9.54 Hz, 1H), 7.84 (d, J=8.03 Hz, 2H), 7.52 (d, J=9.54 Hz, 1H), 7.48 (d, J=8.03 Hz, 2H), 4.25-4.17 (m, 1H), 2.37 (s, 3H), 2.11 (s, 3H), 1.45 (d, J=6.53 Hz, 3H).

The ee of this enantiomer was >99.9%.

Example 38 or Example 39

Separated Isomers

Enantiomer 2: MS (ESI positive ion) m/z: 500 (M+1). Calcd for C$_{22}$H$_{22}$ClN$_7$O$_3$S: 499. 1H NMR (400 MHz, DMSO-d$_6$): δ ppm 10.91 (s, 1H), 8.24 (s, 1H), 8.09-8.06 (m, 2H), 8.02 (d, J=9.39 Hz, 1H), 7.84 (d, J=8.22 Hz, 2H), 7.53 (d, J=9.59 Hz, 1H), 7.48 (d, J=8.22 Hz, 2H), 4.25-4.17 (m, 1H), 2.37 (s, 3H), 2.11 (s, 3H), 1.45 (d, J=6.65 Hz, 3H).

The ee of this enantiomer was 95.4%.

Example 40

N-(6-(6-Chloro-5-(2-chloro-4-fluorophenylsulfonamido)pyridin-3-yl)imidazo[1,2-b]pyridazin-2-yl)acetamide

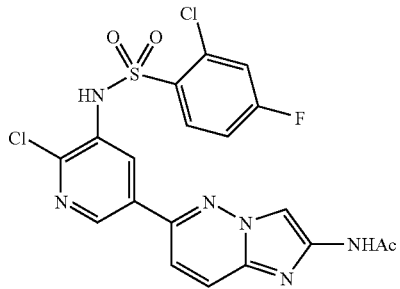

Step 1. N-(5-Bromo-2-chloropyridin-3-yl)-2-chloro-4-fluorobenzenesulfonamide

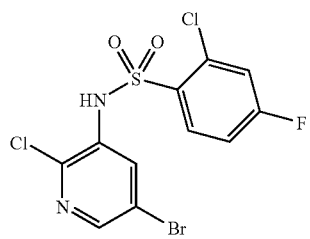

To a round-bottom flask, was added 5-bromo-2-chloropyridin-3-amine (0.2 g, 1.0 mmol, Asymchem Laboratories, Morrisville, N.C.) in THF (10 mL). To this solution, sodium bis(trimethylsilyl)amide (1M in THF, 3 mL, 3 mmol, Aldrich, St. Louis, Mo.) was added and the mixture was stirred for 5 minutes. Then 2-chloro-4-fluorobenzene-1-sulfonyl chloride (0.7 g, 3 mmol, Aldrich, St. Louis, Mo.) was added to the mixture and the suspension was stirred at 25° C. for 15 h. The mixture was diluted with H$_2$O. The organic layer was collected by extracting the water with DCM (3×). The combined organic was dried over sodium sulfate and concentrated in vacuo. Purification by silica gel chromatography (1 to 30% EtOAc/CH$_2$Cl$_2$) gave N-(5-bromo-2-chloropyridin-3-yl)-2-chloro-4-fluorobenzenesulfonamide (0.190 g, 49% yield) as a tan oil. MS (ESI positive ion) m/z: 401 (M+1).

Step 2. N-(6-(6-Chloro-5-(2-chloro-4-fluorophenylsulfonamido)pyridin-3-yl)imidazo[1,2-b]pyridazin-2-yl)acetamide

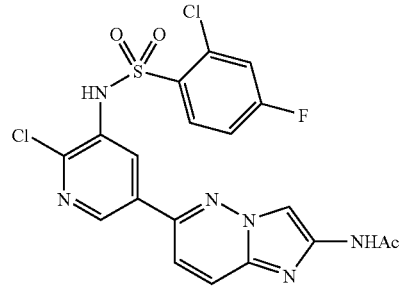

Following the procedure described for compound N-(6-(6-chloro-5-(4-(2-hydroxypropan-2-yl)phenylsulfonamido)pyridin-3-yl)imidazo[1,2-b]pyridazin-2-yl)acetamide (Example 35), N-(6-(4,4,5,5-tetramethyl-1,3,2-dioxaborolan-2-yl)imidazo[1,2-b]pyridazin-2-yl)acetamide (200 mg, 662 μmol) (Example 35, Step 3) was reacted with N-(5-bromo-2-chloropyridin-3-yl)-2-chloro-4-fluorobenzenesulfonamide (265 mg, 662 μmol) to afford the title compound as a grey solid (50 mg, 25% yield). MS (ESI positive ion) m/z: 495 (M+1). $^1$H NMR (400 MHz, DMSO-d$_6$): δ ppm 2.12 (s, 3H), 7.33-7.43 (m, 1H), 7.77 (dd, J=8.61, 2.15 Hz, 1H), 7.83 (d, J=9.39 Hz, 1H), 7.99 (dd, J=8.80, 6.06 Hz, 1H), 7.99 (dd, J=8.80, 6.06 Hz, 1H), 8.12 (d, J=9.39 Hz, 1H), 8.33 (d, J=8.41 Hz, 2H), 8.91 (s, 1H), 10.82-10.92 (br s, 1H), 10.96 (s, 1H).

Example 41

N-(6-(6-Chloro-5-(morpholine-4-sulfonamido)pyridin-3-yl)imidazo[1,2-b]pyridazin-2-yl)acetamide

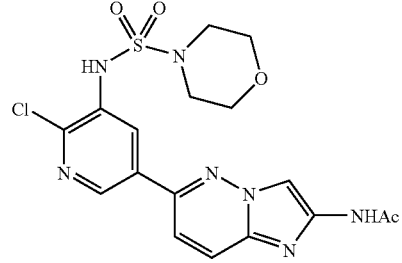

Step 1. N-(5-Bromo-2-chloropyridin-3-yl)morpholine-4-sulfonamide

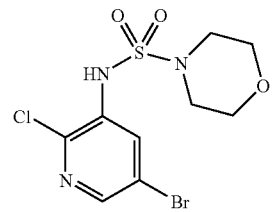

A 50 mL round-bottomed flask was charged with 5-bromo-2-chloropyridin-3-amine (0.863 g, 4.2 mmol) and pyridine (5 mL). To this solution, DMAP (0.13 g, 1.0 mmol) and morpholine (0.36 mL, 4.2 mmol) were added in. The mixture was chilled to −40° C. in a dry ice/acetone bath. Then sulfuryl chloride (0.36 mL, 4.6 mmol) was added dropwise into the mixture while stirring. After the addition, the ice bath was removed and the mixture was allowed to stir under inert atmosphere at 25° C. for 15 h. The mixture was diluted with aqueous sodium bicarbonate and extracted by DCM (3×). The combined organic was dried over sodium sulfate and concentrated in vacuo. Purification by silica gel chromatography (1 to 50% EtOAc/DCM) gave N-(5-bromo-2-chloropyridin-3-yl)morpholine-4-sulfonamide (0.55 g, 37% yield) as a tan crystalline solid. MS (ESI positive ion) m/z: 358 (M+1). $^1$H NMR (400 MHz, DMSO-d$_6$): δ ppm 3.07-3.12 (m, 4H), 3.58-3.62 (m, 4H), 8.07 (d, J=2.15 Hz, 1H), 8.42 (d, J=2.35 Hz, 1H), 10.19 (s, 1H).

Step 2. N-(6-(6-Chloro-5-(morpholine-4-sulfonamido)pyridin-3-yl)imidazo[1,2-b]pyridazin-2-yl)acetamide

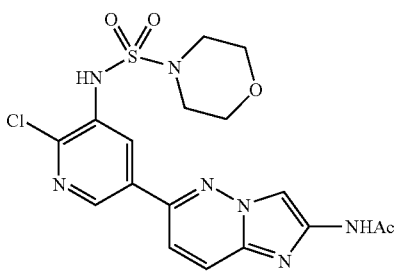

Following the procedure described for compound N-(6-(6-chloro-5-(4-(2-hydroxypropan-2-yl)phenylsulfonamido)pyridin-3-yl)imidazo[1,2-b]pyridazin-2-yl)acetamide (Example 35), N-(6-(4,4,5,5-tetramethyl-1,3,2-dioxaborolan-2-yl)imidazo[1,2-b]pyridazin-2-yl)acetamide (122 mg, 404 µmol) (Example 35, Step 3) was reacted with N-(5-bromo-2-chloropyridin-3-yl)morpholine-4-sulfonamide from Step 1 (120 mg, 336 µmol) to afford the title compound as a light green solid (40 mg, 26% yield). MS (ESI positive ion) m/z: 452 (M+1). $^1$H NMR (400 MHz, DMSO-d$_6$): δ ppm 2.12 (s, 3H), 3.12-3.18 (m, 4H), 3.60-3.68 (m, 4H), 7.86 (d, J=9.39 Hz, 1H), 8.14 (d, J=9.39 Hz, 1H), 8.33 (s, 1H), 8.54 (d, J=2.15 Hz, 1H), 8.90 (s, 1H), 10.14 (s, 1H), 10.97 (s, 1H).

Example 42

N-(6-(6-Chloro-5-(4-methylphenylsulfonamido)pyridin-3-yl)imidazo[1,2-b]pyriadazin-2-yl)acetamide

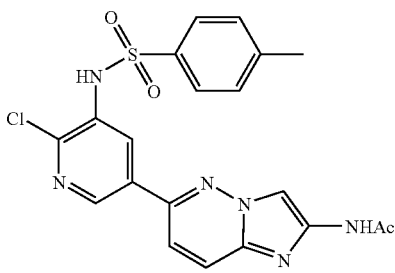

Step 1. N-(5-Bromo-2-chloropyridin-3-yl)-4-methyl-benzenesulfonamide

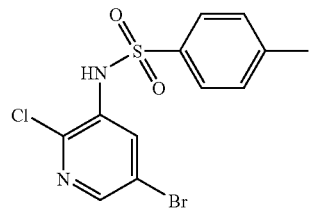

To a 150 mL round-bottomed flask was added 3-amino-5-bromo-2-chloropyridine (1 g, 5 mmol, Asymchem Laboratories, Morrisville, N.C.) and pyridine(20 mL). To this solution, p-toluenesulfonyl chloride (2 g, 10 mmol) and catalytic amount of DMAP were mixed, the mixture was stirred at 25° C. for 48 h. The suspension was concentrated in vacuum, the residue was treated with water, filtration provided 2.5 g white solids. The obtained solid was suspended in methanol (50 mL), and K$_2$CO$_3$ (2.5 g, 18 mmol) was mixed. The reaction mixture was stirred at 25° C. for 48 h and concentrated in vacuum. The residue was diluted with EtOAC, washed by water and brine, dried over MgSO$_4$, and concentrated in vacuum to provide N-(5-bromo-2-chloropyridin-3-yl)-4-methylbenzenesulfonamide (1.5 g, 86% yield) as an off-white solid. MS (ESI positive ion) m/z: 363 (M+1). $^1$H NMR (400 MHz, DMSO-d$_6$): δ ppm 2.38 (s, 3H), 7.39 (d, J=8.53 Hz, 2H), 7.64 (d, J=8.03 Hz, 2H), 7.89 (d, J=2.01 Hz, 1H), 10.52 (s, 1H).

Step 2. N-(6-(6-Chloro-5-(4-methylphenylsulfonamido)pyridin-3-yl)imidazo[1,2-b]pyriadazin-2-yl)acetamide

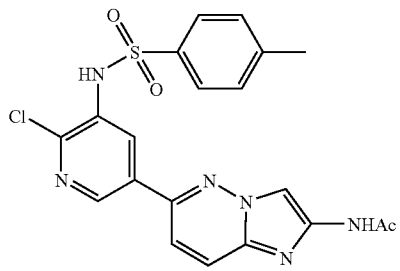

Following the procedure described for compound N-(6-(6-chloro-5-(4-(2-hydroxypropan-2-yl)phenylsulfonamido)pyridin-3-yl)imidazo[1,2-b]pyridazin-2-yl)acetamide (Example 35), N-(6-(4,4,5,5-tetramethyl-1,3-dioxolan-2-yl)imidazo[1,2-b]pyridazin-2-yl)acetamide (126 mg, 415 µmol, Example 35, Step 3) was reacted with N-(5-bromo-2-chloropyridin-3-yl)-4-methylbenzenesulfonamide from Step 1 (120 mg, 332 µmol) to afford the title compound as a yellow solid (30 mg, 20% yield). MS (ESI positive ion) m/z: 457 (M+1). $^1$H NMR (400 MHz, DMSO-d$_6$): δ ppm 2.13 (s, 3H), 2.39 (s, 3H), 7.40 (d, J=8.02 Hz, 2H), 7.68 (d, J=8.22 Hz, 2H), 7.82 (d, J=9.39 Hz, 1H, 8.13 (d, J=9.59 Hz, 1H), 8.30 (d, J=2.15 Hz, 1H), 8.32 (s, 1H), 8.90 (d, J=2.35 Hz, 1H), 10.44 (s, 1H), 10.98 (s, 1H).

Example 43

N-(6-(3,4-Dimethoxyphenyl)imidazo[1,2-b]pyridazin-2-yl)acetamide

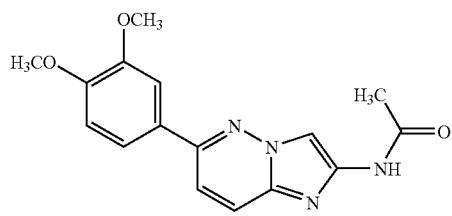

To a 10-mL, reaction vial was added N-(6-chloroimidazo[1,2-b]pyridazin-2-yl)acetamide (0.108 g, 0.51 mmol), 3,4-dimethoxyphenylboronic acid (0.112 g, 0.61 mmol, Alfa Aesar, Ward Hill, Mass.), [1,1'-bis(diphenylphosphino)ferrocene]-dichloropalladium, complex with dichloromethane (31 mg, 0.038 mmol), potassium carbonate (0.213 g, 1.54 mmol), DME (3 mL), and water (1 mL). The vial was sealed and purged with nitrogen for several minutes. The mixture was stirred at 100° C. for 1 h and then allowed to cool to room temperature. The organic phase was taken and the solvents eliminated under vacuum. Purification by silica gel chromatography (4 to 6% MeOH/CH$_2$Cl$_2$) afforded the title compound as an off-white solid. MS (ESI positive ion) m/z: 313 (M+1). $^1$H NMR (400 MHz, DMSO-d$_6$): δ ppm 10.86 (s, 1H), 8.26 (s, 1H), 8.00 (d, J=9.6 Hz, 1H), 7.78 (d, J=9.6 Hz, 1H), 7.66-7.57 (m, 2H), 7.11 (d, J=9.0 Hz, 1H), 3.88 (s, 3H), 3.84 (s, 3H), 2.11 (s, 3H).

Example 44

N-(6-(6-Chloro-5-(3-(difluoromethoxy)phenylsulfonamido)pyridin-3-yl)-3-(pyridin-4-yl)imidazo[1,2-b]pyridazin-2-yl)acetamide

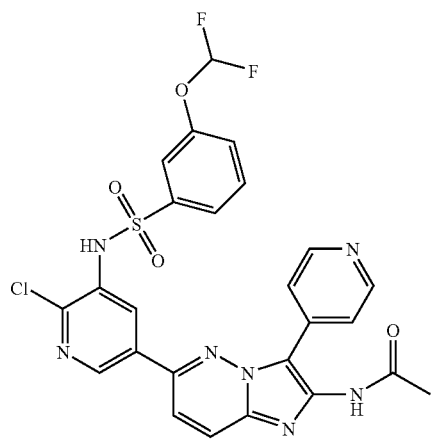

-continued

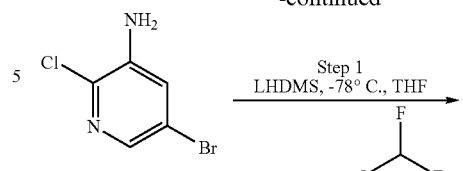
Step 1
LHDMS, -78° C., THF

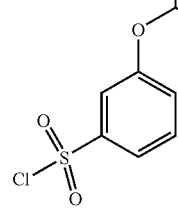

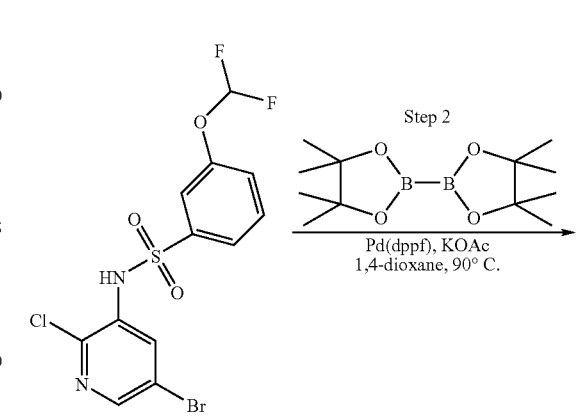

Step 2
Pd(dppf), KOAc
1,4-dioxane, 90° C.

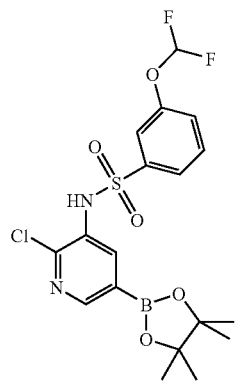

Step 3
Pd(dppf), Na$_2$CO$_3$, H$_2$O
1,4-dioxane, 90° C.

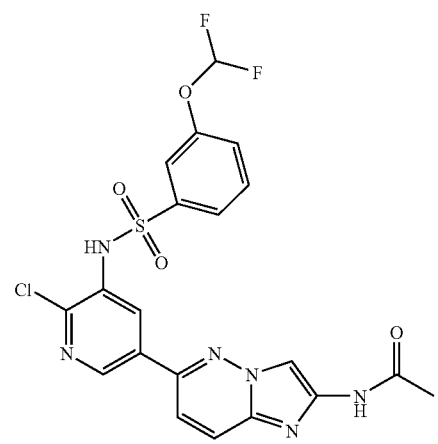

Step 4
NIS
CH$_2$Cl$_2$

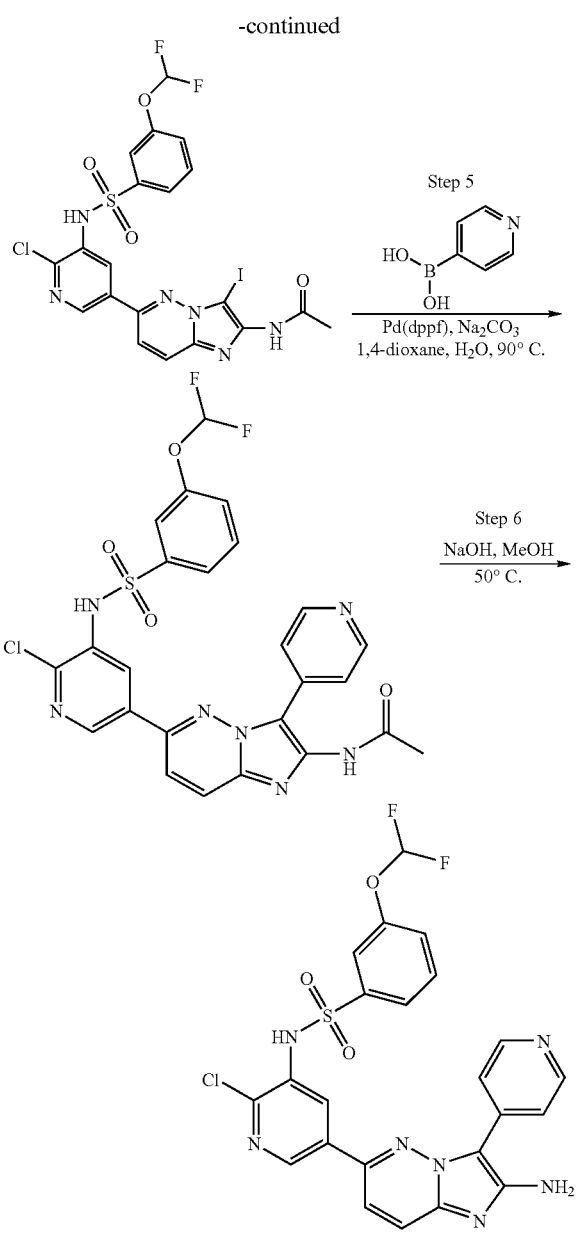

Step 1. N-(5-bromo-2-chloropyridin-3-yl)-3-(difluoromethoxy)benzenesulfonamide

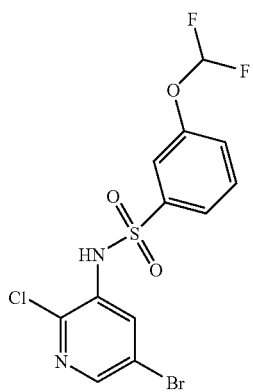

To a THF (20 mL) solution of 3-amino-5-bromo-2-chloropyridine (1.197 g, 5.77 mmol, Asymchem, Morrisville, N.C.)) at −78° C. was added a THF solution of lithium bis(trimethylsilyl)amide (1.0 M, 11.5 mL, 11.5 mmol, Aldrich, St. Louis, Mo.). The solution was maintained for 5 min at −78° C. and then 3-(difluoromethoxy)benzenesulfonyl chloride (1.40 g, 5.77 mmol, Aldrich, St. Louis, Mo.) was added as a solid in a single portion. The solution was allowed to warm to rt, and maintained 1 h. The solution was poured into saturated aqueous $NH_4Cl$ (100 mL) and the resulting mixture was extracted with EtOAc (100 mL). The organic layer was dried ($Na_2SO_4$) and concentrated for purification by MPLC (CombiFlash® Companion®, Teledyne Isco, Lincoln, Nebr.). The residue was taken up in minimal $CH_2Cl_2$ and absorbed onto a 25 g silica loading cartridge and passed through a Redi-Sep® pre-packed silica gel column (Teledyne Isco, Lincoln, Nebr.) (120 g) using a gradient of 98:2 Hexanes:EtOAc to 100% EtOAc to afford N-(5-bromo-2-chloropyridin-3-yl)-3-(difluoromethoxy)benzenesulfonamide (2.235 g, 93.6% yield) as a colorless oil. LCMS (ESI positive ion) m/z: 414.9 (M+1); 1H NMR (400 MHz, CHLOROFORM-d) δ ppm 6.54 (t, J=72.38 Hz, 1H); 7.33-7.42 (m, 2H); 7.51 (t, J=8.07 Hz, 1H); 7.58 (t, J=1.91 Hz, 1H); 7.61-7.68 (m, 1H); 8.13 (d, J=2.25 Hz, 1H); 8.19 (d, J=2.25 Hz, 1H).

Step 2. N-(2-chloro-5-(4,4,5,5-tetramethyl-1,3,2-dioxaborolan-2-yl)pyridin-3-yl)-3-(difluoromethoxy)benzenesulfonamide

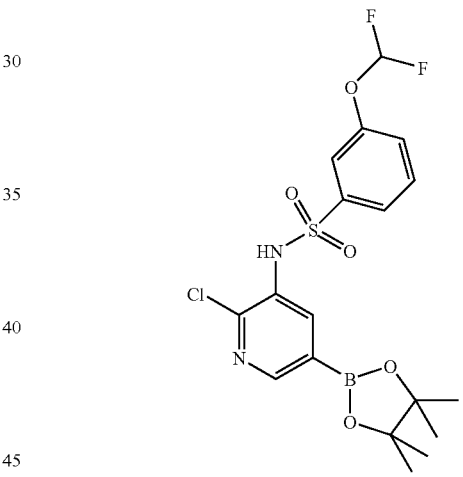

A sealable vial was charged with N-(5-bromo-2-chloropyridin-3-yl)-3-(difluoromethoxy)benzenesulfonamide (2.235 g, 5.40 mmol), bis(pinacolato)diboron (1.65 g, 6.48 mmol, Aldrich, St. Louis, Mo.), potassium acetate (1.35 mL, 21.6 mmol, Aldrich, St. Louis, Mo.), and dichloro 1,1'-bis(diphenylphosphino)ferrocene palladium(II) (0.228 g, 0.411 mmol, Strem Chemical, Inc., Newburyport, Mass.). The vial was sealed with a septa cap and 1,4-dioxane (20 mL, 0.3 M) was added. The resulting mixture was sparged with $N_2$ for 10 min, then heated at 90° C. for 18 h. The reaction mixture was cooled to rt and absorbed directly onto a 25 g silica loading cartridge for purification by MPLC (CombiFlash® Companion®, Teledyne Isco, Lincoln, Nebr.). The residue was passed through a Redi-Sep® pre-packed silica gel column (120 g) (Teledyne Isco, Lincoln, Nebr.) using 95:5 Hexanes:EtOAc to 100% EtOAc gradient to afford N-(2-chloro-5-(4,4,5,5-tetramethyl-1,3,2-dioxaborolan-2-yl)pyridin-3-yl)-3-(difluoromethoxy)benzenesulfonamide (2.127 g, 85.4% yield) as a brown oil. LCMS (formic acid modifier, ESI positive ionization) m/z: 379.2 (M+1, boronic ester hydrolizes to corresponding acid on LCMS); 1H NMR (400 MHz, CHLOROFORM-d) δ ppm 1.35 (s, 12H); 6.50 (t, J=72.63 Hz, 1H); 7.12

(s, 1H); 7.30-7.37 (m, 1H); 7.44-7.51 (m, 1H); 7.55 (t, J=1.86 Hz, 1H); 7.58-7.64 (m, 1H); 8.29 (d, J=1.66 Hz, 1H); 8.44 (d, J=1.76 Hz, 1H).

Step 3. N-(6-(6-chloro-5-(3-(difluoromethoxy)phenylsulfonamido)pyridin-3-yl)imidazo[1,2-b]pyridazin-2-yl)acetamide

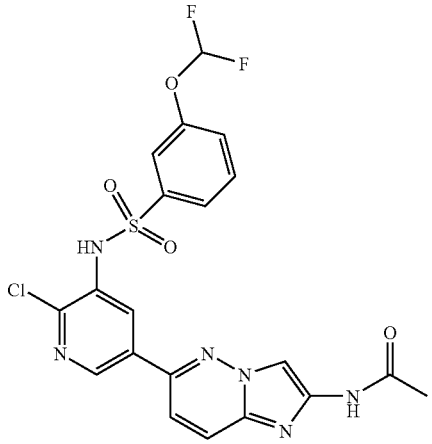

A sealable vial was charged with N-(2-chloro-5-(4,4,5,5-tetramethyl-1,3,2-dioxaborolan-2-yl)pyridin-3-yl)-3-(difluoromethoxy)benzenesulfonamide (765.9 mg, 1663 µmol), N-(6-chloroimidazo[1,2-b]pyridazin-2-yl)acetamide (291.8 mg, 1385 µmol, Example 1, Step 4), dichloro 1,1'-bis(diphenylphosphino)ferrocene palladium(II) (53.76 mg, 96.98 µmol, Strem Chemical, Inc., Newburyport, Mass.) and sodium carbonate (293.7 mg, 2771 µmol). The vial was sealed with a septum cap and dioxane (2 mL, 1 M) and water (1 mL, 2 M) were added via syringe. The mixture was sparged 10 min with N$_2$, then heated at 90° C. for 18 h. The solution was cooled to rt, and concentrated for purification by MPLC (CombiFlash® Companion®, Teledyne Isco, Lincoln, Nebr.). The crude residue was taken up in minimal CH$_2$Cl$_2$/MeOH and absorbed onto a 25 g silica loading cartridge and passed through a Redi-Sep® pre-packed silica gel column (80 g) (Teledyne Isco, Lincoln, Nebr.) using a gradient of 1% MeOH in CH$_2$Cl$_2$ to 10% MeOH in CH$_2$Cl$_2$ to afford N-(6-(6-chloro-5-(3-(difluoromethoxy)phenylsulfonamido)pyridin-3-yl)imidazo[1,2-b]pyridazin-2-yl)acetamide (584.0 mg, 82.83% yield) as a brown solid. LCMS (ESI) m/z: 509.1 (M+1).

Step 4. N-(6-(6-chloro-5-(3-(difluoromethoxy)phenylsulfonamido)pyridin-3-yl)-3-iodoimidazo[1,2-b]pyridazin-2-yl)acetamide

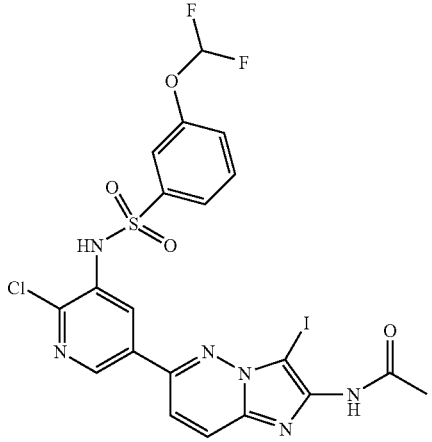

To a CH$_2$Cl$_2$ (20 mL) solution N-(6-(6-chloro-5-(3-(difluoromethoxy)phenylsulfonamido)pyridin-3-yl)imidazo[1,2-b]pyridazin-2-yl)acetamide (315.0 mg, 619.0 µmol) was added n-iodosuccinimide (195.0 mg, 866.6 µmol, Alfa Aesar, Ward Hill, Mass.) as a solid in a single portion. The solution turned dark brown and was maintained at rt for 1 h. The solution was concentrated for purification by MPLC (CombiFlash® Companion®, Teledyne Isco, Lincoln, Nebr.). The crude residue was taken up in minimal CH$_2$Cl$_2$/MeOH and absorbed onto a 25 g silica loading cartridge and passed through a Redi-Sep® pre-packed silica gel column (Teledyne Isco, Lincoln, Nebr.) (80 g) using a gradient of 1% MeOH in CH$_2$Cl$_2$ to 10% MeOH in CH$_2$Cl$_2$ to afford N-(6-(6-chloro-5-(3-(difluoromethoxy)phenylsulfonamido)pyridin-3-yl)-3-iodoimidazo[1,2-b]pyridazin-2-yl)acetamide (370.0 mg, 94.16% yield) as a brown solid. LCMS (ESI positive ionization) m/z: 635 (M+1).

Step 5. N-(6-(6-chloro-5-(3-(difluoromethoxy)phenylsulfonamido)pyridin-3-yl)-3-(pyridin-4-yl)imidazo[1,2-b]pyridazin-2-yl)acetamide

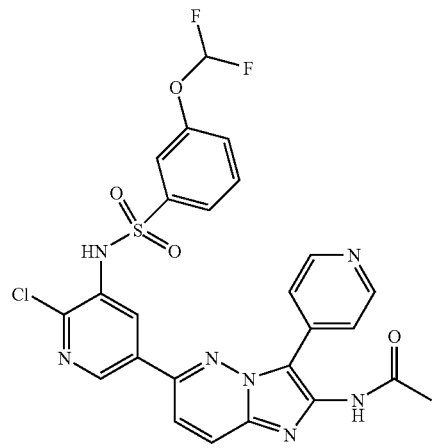

A sealable vial was charged with N-(6-(6-chloro-5-(3-(difluoromethoxy)phenylsulfonamido)pyridin-3-yl)-3-iodoimidazo[1,2-b]pyridazin-2-yl)acetamide (129.0 mg, 203 µmol), 4-pyridylboronic acid (30.0 mg, 244 µmol, Alfa Aesar, Ward Hill, Mass.), sodium carbonate (86.2 mg, 813 µmol), and dichloro 1,1'-bis(diphenylphosphino)ferrocene palladium(II) (11.3 mg, 20.3 µmol, Strem Chemical, Inc., Newburyport, Mass.). The vial was sealed with a septum cap, and 1,4-dioxane (2 mL) was added under positive N$_2$ flow followed by water (0.2 mL). The mixture was sparged with N$_2$ for 10 min and then heated at 80° C. for 18 h. The solution was cooled to rt and absorbed directly onto a 25 g silica loading cartridge and passed through a Redi-Sep® pre-packed silica gel column (80 g) (Teledyne Isco, Lincoln, Nebr.) using a gradient of 1% MeOH in CH$_2$Cl$_2$ to 10% MeOH in CH$_2$Cl$_2$ to afford the title compound, N-(6-(6-chloro-5-(3-(difluoromethoxy)phenylsulfonamido)pyridin-3-yl)-3-(pyridin-4-yl)imidazo[1,2-b]pyridazin-2-yl)acetamide (67.0 mg, 56.3% yield) as a yellow solid. LCMS (ESI positive ion) m/z: 586 (M+1); 1H NMR (400 MHz, MeOH) δ ppm 2.21 (s, 3H); 6.61-6.97 (m, 1H); 7.33-7.40 (m, 1H); 7.48 (t, J=8.07 Hz, 1H); 7.56 (s, 1H); 7.95 (d, J=9.49 Hz, 1H); 8.06 (d, J=4.99 Hz, 2H); 8.17 (d, J=9.49 Hz, 1H); 8.67-8.74 (m, 2H); 8.80 (d, J=1.96 Hz, 2H).

Example 45

N-(5-(2-Amino-3-(pyridin-4-yl)imidazo[1,2-b]pyridazin-6-yl)-2-chloropyridin-3-yl)-3-(difluoromethoxy)benzenesulfonamide

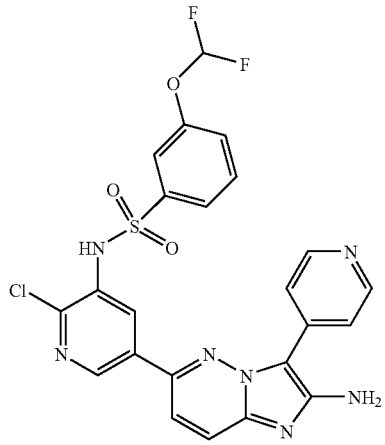

A sealable vial was charged with N-(6-(6-chloro-5-(3-(difluoromethoxy)phenylsulfonamido)pyridin-3-yl)-3-(pyridin-4-yl)imidazo[1,2-b]pyridazin-2-yl)acetamide (53 mg, 90 µmol) and MeOH (1.5 mL) followed by aqueous sodium hydroxide (6 N, 226 µl, 1357 µmol). The vial was sealed and heated at 50° C. for 18 h. The solution was cooled to rt, then concentrated. The resulting yellow solid was washed with saturated aqueous NaHCO$_3$ (1 mL), then water (2 mL). The solid was slurried in water/IPA (2 mL) and collected by vacuum filtration to yield N-(5-(2-amino-3-(pyridin-4-yl)imidazo[1,2-b]pyridazin-6-yl)-2-chloropyridin-3-yl)-3-(difluoromethoxy)benzenesulfonamide-2,2,2-trifluoroacetic acid salt (21 mg, 43% yield) as a yellow solid. LCMS (ESI positive ion) m/z: 544.2; 1H NMR (400 MHz, MeOH) δ ppm 6.69 (t, J=73.70 Hz, 1H); 7.13 (dd, J=7.97, 2.20 Hz, 1H); 7.33 (t, J=7.97 Hz, 1H); 7.59-7.69 (m, 2H); 7.71-7.83 (m, 2H); 8.15-8.23 (m, 2H); 8.25 (d, J=2.25 Hz, 1H); 8.49 (d, J=2.25 Hz, 1H); 8.66 (dd, J=4.79, 1.57 Hz, 2H).

Example 46

N-(6-(6-Chloro-5-(3-(difluoromethoxy)phenylsulfonamido)pyridin-3-yl)-3-(2-methylpyridin-4-yl)imidazo[1,2-b]pyridazin-2-yl)acetamide

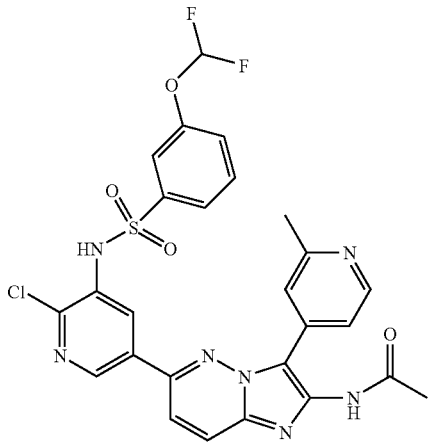

Following the procedure described in Example 44 (Step 5) N-(6-(6-chloro-5-(3-(difluoromethoxy)phenylsulfonamido)pyridin-3-yl)-3-iodoimidazo[1,2-b]pyridazin-2-yl)acetamide (114.0 mg, 180 µmol) was combined with 2-methylpyridin-4-ylboronic acid (30 mg, 216 µmol) to afford the title compound, N-(6-(6-chloro-5-(3-(difluoromethoxy)phenylsulfonamido)pyridin-3-yl)-3-(2-methylpyridin-4-yl)imidazo[1,2-b]pyridazin-2-yl)acetamide as a yellow solid. LCMS (ESI positive ion) m/z: 600.0 (M+1); 1H NMR (400 MHz, MeOH) δ ppm 2.21 (s, 3H), 2.67 (s, 3H), 6.80 (t, J=73.11 Hz, 1H), 7.35 (dd, J=8.22, 1.96 Hz, 1H), 7.47 (t, J=8.07 Hz, 1H), 7.54 (s, 1H), 7.57-7.64 (m, 1H), 7.80-7.85 (m, 1H), 7.86-7.96 (m, 2H), 8.14 (d, J=9.49 Hz, 1H), 8.57 (d, J=5.38 Hz, 1H), 8.74 (dd, J=22.45, 2.20 Hz, 2H).

Example 47

N-(5-(2-Amino-3-(2-methylpyridin-4-yl)imidazo[1,2-b]pyridazin-6-yl)-2-chloropyridin-3-yl)-3-(difluoromethoxy)benzenesulfonamide (TFA Salt)

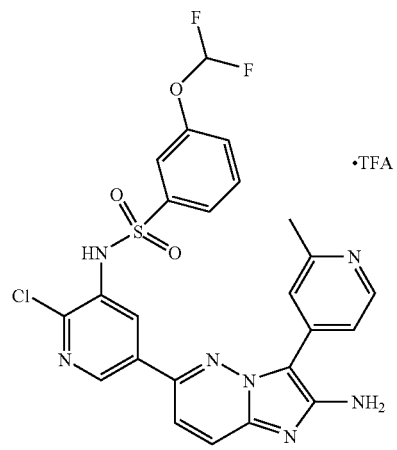

Following the procedure described in Example 45, N-(6-(6-chloro-5-(3-(difluoromethoxy)phenylsulfonamido)pyridin-3-yl)-3-(2-methylpyridin-4-yl)imidazo[1,2-b]pyridazin-2-yl)acetamide (Example 46) was converted to the title compound, N-(5-(2-amino-3-(2-methylpyridin-4-yl)imidazo[1,2-b]pyridazin-6-yl)-2-chloropyridin-3-yl)-3-(difluoromethoxy)benzenesulfonamide (32 mg, 70% yield), which was isolated as the trifluoroacetic acid salt after purification by preparative HPLC (Gilson GX-281, Middletown, Wis.: 5-90% (0.1% TFA in CH$_3$CN) in H$_2$O over 15 min (Phenomenex, Zorbax 00F-4435-UO 150×30 mm, 5 micron). LCMS (ESI positive ion) m/z: 558.0 (M+1); 1H NMR (400 MHz, MeOH) δ ppm 2.83 (s, 3H); 6.82 (t, J=73.02 Hz, 1H); 7.40 (d, J=8.12 Hz, 1H); 7.52-7.57 (m, 2H); 7.59-7.67 (m, 1H); 7.89-8.04 (m, 2H); 8.42 (s, 1H); 8.49 (d, J=6.75 Hz, 1H); 8.64 (dd, J=6.75, 1.76 Hz, 1H); 8.80 (dd, J=10.12, 2.20 Hz, 2H).

Example 48

N-(6-(6-Chloro-5-(4-fluorophenylsulfonamido)pyridin-3-yl)-3-(pyridin-4-yl)imidazo[1,2-b]pyridazin-2-yl)acetamide

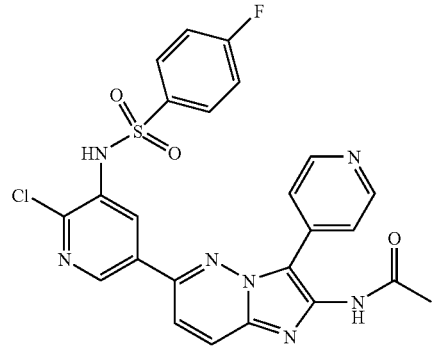

Step 1: N-(5-bromo-2-chloropyridin-3-yl)-4-fluorobenzenesulfonamide

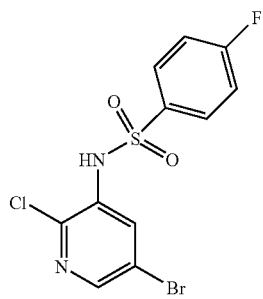

Following the procedure previously described (Example 44, Step 1), 3-amino-5-bromo-2-chloropyridine (770.0 mg, 3.7 mmol) was reacted with 4-fluorobenzenesulfonyl chloride (0.76 g, 3.9 mmol, Oakwood Products, West Columbia, S.C.) to afford N-(5-bromo-2-chloropyridin-3-yl)-4-fluorobenzenesulfonamide (1.018 g, 75% yield) after recrystallization from $CH_2Cl_2$/EtOAc. LCMS (ESI positive ionization) m/z: 366 (M+1); 1 H NMR (400 MHz, DMSO-$d_6$) δ ppm 7.24 (t, J=9.00 Hz, 2H); 7.53 (d, J=2.25 Hz, 1H); 7.58 (d, J=2.25 Hz, 1H); 7.74 (dd, J=8.95, 5.43 Hz, 2H).

Step 2: N-(2-chloro-5-(4,4,5,5-tetramethyl-1,3,2-dioxaborolan-2-yl)pyridin-3-yl)-4-fluorobenzenesulfonamide

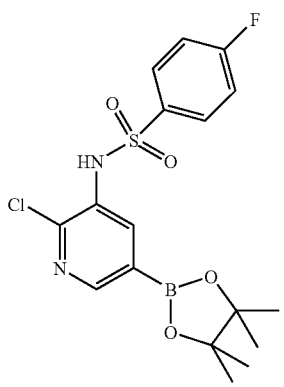

Following the procedure previously described (Example 44, Step 2), N-(5-bromo-2-chloropyridin-3-yl)-4-fluorobenzenesulfonamide was converted to N-(2-chloro-5-(4,4,5,5-tetramethyl-1,3,2-dioxaborolan-2-yl)pyridin-3-yl)-4-fluorobenzenesulfonamide.

Step 3: N-(6-chloro-3-iodoimidazo[1,2-b]pyridazin-2-yl)acetamide

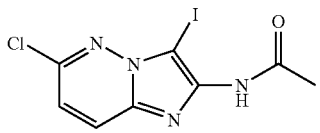

To a $CHCl_3$ (20 mL) solution of N-(6-chloroimidazo[1,2-b]pyridazin-2-yl)acetamide (320.4 mg, 1521 μmol) was added n-iodosuccinimide (167.4 μl, 1673 μmol) as a solid in a single portion. The solution was maintained at rt for 20 min, then poured into water. The resulting mixture was extracted with $CH_2Cl_2$ (1×50 mL). The layers were separated and the organic layer was washed with saturated aqueous $Na_2S_2O_3$ (1×20 mL) and brine (1×10 mL). The organic layer was dried ($Na_2SO_4$) and concentrated for purification by MPLC (CombiFlash® Companion®, Teledyne Isco, Lincoln, Nebr.). The residue was taken up in minimal $CH_2Cl_2$/MeOH and absorbed onto a 25 g silica loading cartridge and passed through a Redi-Sep® pre-packed silica gel column (80 g) (Teledyne Isco, Lincoln, Nebr.) using a gradient of 1% MeOH in $CH_2Cl_2$ to 10% MeOH in $CH_2Cl_2$ to afford N-(6-chloro-3-iodoimidazo[1,2-b]pyridazin-2-yl)acetamide (427.0 mg, 83.41% yield) as a grey solid. LCMS (ESI positive ionization) m/z: 337.2 (M+1).

Step 4: N-(6-chloro-3-(pyridin-4-yl)imidazo[1,2-b]pyridazin-2-yl)acetamide (TFA Salt)

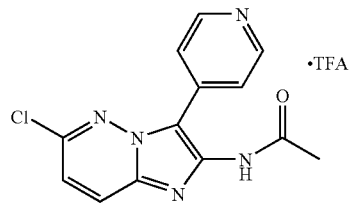

A sealable vial was charged with N-(6-chloro-3-iodoimidazo[1,2-b]pyridazin-2-yl)acetamide (74.0 mg, 220 μmol), 4-pyridylboronic acid (32.4 mg, 264 μmol), sodium carbonate (93.2 mg, 880 μmol), and dichloro 1,1'-bis(diphenylphosphino)ferrocene palladium(II) (122 mg, 220 μmol). The vial was sealed with a septum cap and 1,4-dioxane (2 mL) was added under positive $N_2$ flow followed by water (1 mL). The mixture was sparged with $N_2$ for 10 min and heated at 80° C. for 18 h. The solution was concentrated and the residue was taken up in minimal MeOH/DMSO and purified by preparative HPLC (Gilson GX-281, Middletown, Wis.: 5-90% (0.1% TFA in $CH_3CN$) in $H_2O$ over 15 min, Phenomenex, Zorbax 00F-4435-UO 150×30 mm, 5 micron) to afford N-(6-chloro-3-(pyridin-4-yl)imidazo[1,2-b]pyridazin-2-yl)acetamide (47.0 mg, 74.3% yield) as a trifluoroacetic acid salt. LCMS (ESI positive ionization) m/z: 288.3 (M+1).

Step 5. N-(6-(6-chloro-5-(4-fluorophenylsulfonamido)pyridin-3-yl)-3-(pyridin-4-yl)imidazo[1,2-b]pyridazin-2-yl)acetamide

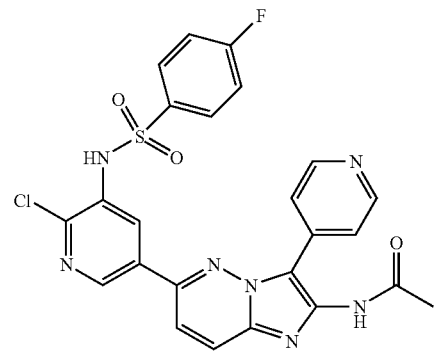

A sealable vial was charged with N-(2-chloro-5-(4,4,5,5-tetramethyl-1,3,2-dioxaborolan-2-yl)pyridin-3-yl)-4-fluorobenzenesulfonamide (81 mg, 196 μmol), N-(6-chloro-3-(pyridin-4-yl)imidazo[1,2-b]pyridazin-2-yl)acetamide-TFA salt (47.0 mg, 163 μmol), sodium carbonate (69 mg, 653 μmol) and dichloro 1,1'-bis(diphenylphosphino)ferrocene palladium(II) (9.1 mg, 16 μmol). The vial was sealed with a septum cap and 1,4-dioxane (2 mL) and water (0.2 mL) were added under positive $N_2$ flow. The mixture was sparged for 10 min with N₂ and heated at 90° C. for 18 h. The solution was cooled to rt and concentrated for purification by MPLC (CombiFlash® Companion®, Teledyne Isco, Lincoln, Nebr.). The residue was taken up in minimal CH₂Cl₂/MeOH and absorbed onto a 25 g silica loading cartridge and passed through a Redi-Sep® pre-packed silica gel column (80 g) (Teledyne Isco, Lincoln, Nebr.) using a gradient of 1% MeOH in CH₂Cl₂ to 10% MeOH in CH₂Cl₂ to afford the title compound, N-(6-(6-chloro-5-(4-fluorophenylsulfonamido)pyridin-3-yl)-3-(pyridin-4-yl)imidazo[1,2-b]pyridazin-2-yl)acetamide (23 mg, 26% yield) as a yellow solid. LCMS (ESI positive ionization) m/z: 538.0 (M+1); 1H NMR (400 MHz, MeOH-d₆) δ ppm 2.27 (s, 3H) 7.95-8.07 (m, 2H) 8.21 (dd, J=61.57, 9.54 Hz, 2H) 8.63-8.71 (m, 3H) 8.76-8.81 (m, 2H) 8.82-8.86 (m, 2H) 8.87-8.92 (m, 2H).

The above compound, N-(6-(6-chloro-5-(4-fluorophenylsulfonamido)pyridin-3-yl)-3-(pyridin-4-yl)imidazo[1,2-b]pyridazin-2-yl)acetamide, could also be made by the scheme described for Example 44, starting from N-(5-bromo-2-chloropyridin-3-yl)-4-fluorobenzenesulfonamide.

Example 49

N-(6-(6-Chloro-5-(3-(difluoromethoxy)phenylsulfonamido)pyridin-3-yl)-3-(pyridin-3-yl)imidazo[1,2-b]pyridazin-2-yl)acetamide

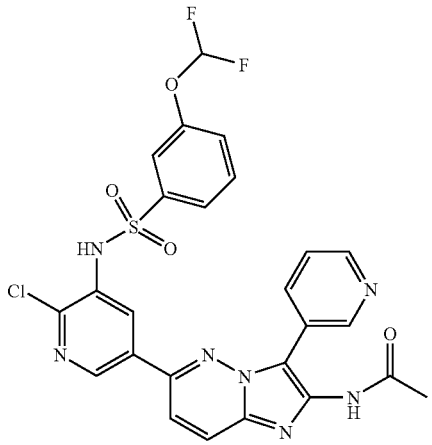

A sealable vial was charged with N-(6-(6-chloro-5-(3-(difluoromethoxy)phenylsulfonamido)pyridin-3-yl)-3-iodoimidazo[1,2-b]pyridazin-2-yl)acetamide (27.0 mg, 42.5 µmol), 3-pyridylboronic acid (6.27 mg, 51.0 µmol), and dichloro 1,1'-bis(diphenylphosphino)ferrocene palladium(II) (2.36 mg, 4.25 µmol). The vial was sealed and 1,4-dioxane (1 mL) was added under positive N₂ flow. Then an aqueous solution of sodium carbonate (1.9 M, 89.5 µl, 170 µmol) was added via syringe. The resulting solution was sparged with N₂ for 10 minutes, then heated at 90° C. for 18 h. The solution was cooled to rt and directly absorbed onto a 5 g silica loading cartridge and passed through a Redi-Sep® pre-packed silica gel column (Teledyne Isco, Lincoln, Nebr.) (12 g) using a gradient of 1% MeOH in CH₂Cl₂ to 10% MeOH in CH₂Cl₂ to afford the title compound N-(6-(6-chloro-5-(3-(difluoromethoxy)phenylsulfonamido)pyridin-3-yl)-3-(pyridin-3-yl)imidazo[1,2-b]pyridazin-2-yl)acetamide as a yellow solid. LCMS (ESI positive ionization) m/z: 586 (M+1); 1H NMR (400 MHz, MeOH) δ ppm 2.18 (s, 3H); 6.81 (t, J=73.11 Hz, 1H); 7.32-7.40 (m, 1H); 7.48 (t, J=8.02 Hz, 1H); 7.53-7.57 (m, 1H); 7.58-7.63 (m, 1H); 7.67 (dd, J=7.87, 5.04 Hz, 1H); 7.90 (d, J=9.49 Hz, 1H); 8.15 (d, J=9.49 Hz, 1H); 8.47 (d, J=8.02 Hz, 1H); 8.60 (d, J=3.52 Hz, 1H); 8.64 (d, J=2.25 Hz, 1H); 8.77 (d, J=2.25 Hz, 1H); 8.97 (s, 1H).

Example 50

N-(5-(2-Amino-3-(pyridin-3-yl)imidazo[1,2-b]pyridazin-6-yl)-2-chloropyridin-3-yl)-3-(difluoromethoxy)benzenesulfonamide (TFA Salt)

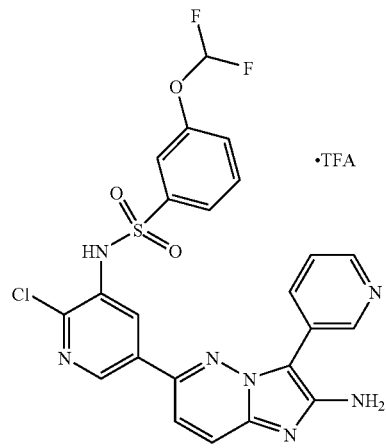

Following the procedure described in Example 45, N-(6-(6-chloro-5-(3-(difluoromethoxy)phenylsulfonamido)pyridin-3-yl)-3-(pyridin-3-yl)imidazo[1,2-b]pyridazin-2-yl)acetamide was converted to the title compound, N-(5-(2-amino-3-(pyridin-3-yl)imidazo[1,2-b]pyridazin-6-yl)-2-chloropyridin-3-yl)-3-(difluoromethoxy)benzenesulfonamide (17.0 mg, 60.7% yield), which was isolated as the trifluoroacetic acid salt after purification by preparative HPLC (Gilson GX-281, Middletown, Wis.: 5-90% (0.1% TFA in CH₃CN, Phenomenex, Zorbax 00F-4435-UO 150×30 mm, 5 micron) in H₂O over 15 min. LCMS (ESI positive ion) m/z: 544.2 (M+1); 1H NMR (400 MHz, MeOH) δ ppm 6.82 (t, J=73.07 Hz, 1H); 7.35-7.45 (m, 1H); 7.48-7.57 (m, 2H); 7.58-7.66 (m, 1H); 7.90-7.95 (m, 1H); 7.96-8.03 (m, 1H); 8.14-8.22 (m, 1H); 8.67-8.72 (m, 1H); 8.75 (d, J=2.25 Hz, 1H); 8.82 (d, J=2.25 Hz, 1H); 9.19-9.28 (m, 1H); 9.45-9.51 (m, 1H).

Example 51

N-(5-(2-Amino-3-(1,2,3,6-tetrahydropyridin-4-yl)imidazo[1,2-b]pyridazin-6-yl)-2-chloropyridin-3-yl)-3-(difluoromethoxy)benzenesulfonamide (TFA Salt)

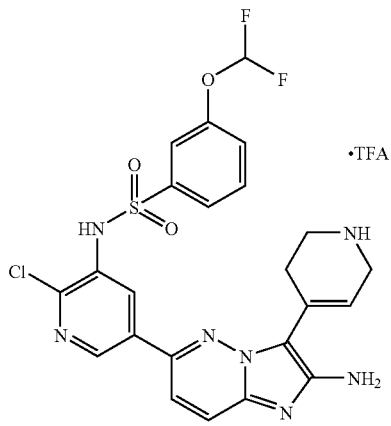

Step 1: tert-butyl 4-(2-acetamido-6-(6-chloro-5-(3-(difluoromethoxy)phenylsulfonamido)pyridin-3-yl)imidazo[1,2-b]pyridazin-3-yl)-5,6-dihydropyridine-1(2H)-carboxylate

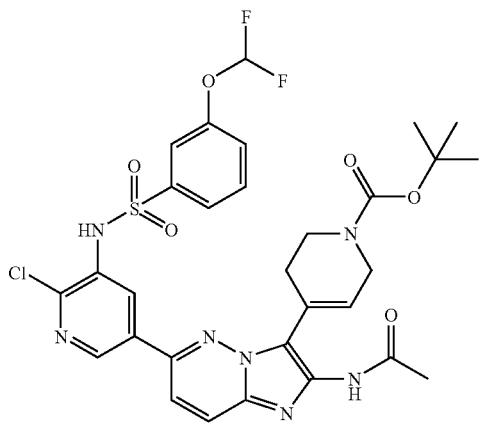

Following the procedure described in Example 49, N-(6-(6-chloro-5-(3-(difluoromethoxy)phenylsulfonamido)pyridin-3-yl)-3-iodoimidazo[1,2-b]pyridazin-2-yl)acetamide (370.0 mg, 583 μmol) was combined with tert-butyl 4-(4,4,5,5-tetramethyl-1,3,2-dioxaborolan-2-yl)-5,6-dihydropyridine-1(2H)-carboxylate (216 mg, 699 μmol, (Carbocore, The Woodlands, Tex.) to afford tert-butyl 4-(2-acetamido-6-(6-chloro-5-(3-(difluoromethoxy)phenylsulfonamido)pyridin-3-yl)imidazo[1,2-b]pyridazin-3-yl)-5,6-dihydropyridine-1(2H)-carboxylate (104 mg, 25.9% yield) as a yellow solid. LCMS (ESI positive ionization) m/z: 691 (M+1).

Step 2: N-(5-(2-amino-3-(1,2,3,6-tetrahydropyridin-4-yl)imidazo[1,2-b]pyridazin-6-yl)-2-chloropyridin-3-yl)-3-(difluoromethoxy)benzenesulfonamide (TFA Salt)

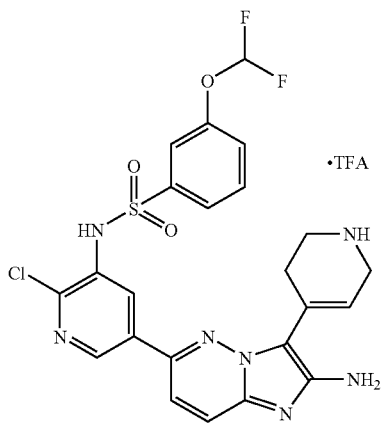

A sealable vial was charged with tert-butyl 4-(2-acetamido-6-(6-chloro-5-(3-(difluoromethoxy)phenylsulfonamido)pyridin-3-yl)imidazo[1,2-b]pyridazin-3-yl)-5,6-dihydropyridine-1(2H)-carboxylate (104.0 mg, 151 μmol) and neat trifluoroacetic acid (1.16 mL, 15.1 mmol). The solution was stirred at rt for 1 h. The solution was then concentrated to give N-(6-(6-chloro-5-(3-(difluoromethoxy)phenylsulfonamido)pyridin-3-yl)-3-(1,2,3,6-tetrahydropyridin-4-yl)imidazo[1,2-b]pyridazin-2-yl)acetamide, which was of sufficient purity for further use. Methanol (2.0 mL) was added to the crude residue followed by an aqueous solution of sodium hydroxide (6 N, 502 μl, 3014 μmol). The solution was heated at 50° for 18 h. The solution was concentrated, then taken up in minimal MeOH/DMSO and purified by preparative HPLC (Gilson GX-218, Middletown, Wis.: 5-90% (0.1% TFA in CH$_3$CN) in H$_2$O over 15 min, Phenomenex, Zorbax 00F-4435-UO 150×30 mm, 5 micron) to afford the title compound, N-(5-(2-amino-3-(1,2,3,6-tetrahydropyridin-4-yl)imidazo[1,2-b]pyridazin-6-yl)-2-chloropyridin-3-yl)-3-(difluoromethoxy)benzenesulfonamide (8.6 mg, 8.6% yield) as a yellow solid. LCMS (ESI positive ionization) m/z: 548.1 (M+1); 1H NMR (400 MHz, MeOH) δ ppm 3.12-3.23 (m, 2H); 3.59 (t, J=5.97 Hz, 2H); 3.97-4.08 (m, 2H); 6.35-6.48 (m, 1H); 6.84 (t, J=73.02 Hz, 1H); 7.40-7.46 (m, 1H); 7.49-7.66 (m, 3H); 7.87-7.94 (m, 1H); 7.97-8.04 (m, 1H); 8.79 (dd, J=15.55, 2.25 Hz, 2H).

Example 52

N-(6-(6-Chloro-5-(4-fluorophenylsulfonamido)pyridazin-3-yl)imidazo[1,2-b]pyridazin-2-yl)acetamide

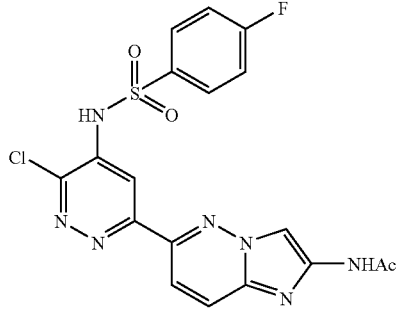

Step 1. 3,6-dichloropyridazin-4-amine

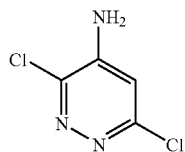

A glass microwave reaction vessel was charged with 3,4,6-trichloropyridazine (732 mg, 3991 μmol), ammonia, (2.0 M solution in methanol, 3991 μl, 7982 μmol). The reaction mixture was stirred and heated in a Smith Synthesizer® microwave reactor (Personal Chemistry, Inc., Upssala, Sweden) at 100° C. for 10 min. The solvent was removed in vacuo and the residue was purified by silica gel chromatography (80% EtOAc/hexanes) to give 6-dichloropyridazin-4-amine (226 mg, 35% yield). MS (ESI positive ion) m/z: 164 (M+1). $^1$H NMR (300 MHz, DMSO-d$_6$) δ ppm 6.83 (s, 1H) 7.15 (s, 2H)

Step 2. N-(3,6-dichloropyridazin-4-yl)-4-fluorobenzenesulfonamide

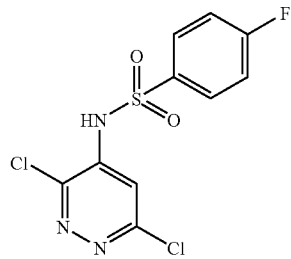

To a 50 mL round-bottomed flask was added 3,6-dichloropyridazin-4-amine (148 mg, 902 µmol), sodium bis(trimethylsilyl)amide (365 µl, 1805 µmol) and THF (3 mL) at 0° C. The mixture was stirred at 0° C. for 30 min. 4-fluorobenzene-1-sulfonyl chloride (263 mg, 1354 µmol) was then added. The mixture was stirred at 0° C. for 1 hour. The reaction mixture was diluted with satd NH$_4$Cl (10 mL) and extracted with EtOAc (3×30 mL). The combined organic extracts were washed with satd NaCl (5 mL), dried over Na$_2$SO$_4$, filtered and concentrated in vacuo and the residue was purified by silica gel chromatography (5% MeOH/EtOAc) to give N-(3,6-dichloropyridazin-4-yl)-4-fluorobenzenesulfonamide (252 mg, 86.7% yield). MS (ESI positive ion) m/z: 323 (M+1). $^1$H NMR (300 MHz, DMSO-d$_6$) δ ppm 6.95 (s, 1H) 7.23-7.35 (m, 2H) 7.74-7.84 (m, 2H)

Step 3: N-(6-(6-chloro-5-(4-fluorophenylsulfonamido)pyridazin-3-yl)imidazo[1,2-b]pyridazin-2-yl)acetamide

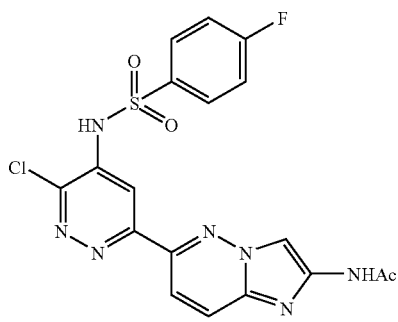

To a 50 mL round-bottomed flask was added N-(6-(4,4,5,5-tetramethyl-1,3,2-dioxaborolan-2-yl)imidazo[1,2-b]pyridazin-2-yl)acetamide (100 mg, 331 µmol), N-(3,6-dichloropyridazin-4-yl)-4-fluorobenzenesulfonamide (107 mg, 331 µmol), cesium carbonate (216 mg, 662 µmol, 662 µmol), dioxane (3 mL), water (0.5 mL). The reaction mixture was stirred at 90° C. for 2 h. The mixture was cooled down to room temperature. The reaction mixture was diluted with satd NH$_4$Cl (2 mL) and extracted with EtOAc (3×20 mL). The combined organic extracts were washed with satd NaCl (2 mL), dried over Na$_2$SO$_4$, filtered and concentrated in vacuo and the residue was purified by silica gel chromatography (15% MeOH/CH$_2$Cl$_2$) to give N-(6-(6-chloro-5-(4-fluorophenylsulfonamido)pyridazin-3-yl)imidazo[1,2-b]pyridazin-2-yl)acetamide (21 mg, 14% yield). MS (ESI positive ion) m/z: 461 (M+1). $^1$H NMR (300 MHz, DMSO-d$_6$) δ ppm 2.13 (s, 3H) 7.36 (t, J=8.70 Hz, 3H) 7.53 (d, J=8.18 Hz, 1H) 7.82-8.00 (m, J=6.14 Hz, 2H) 8.05 (d, J=9.35 Hz, 1H) 8.29 (s, 1H)

Example 53

N-(6-(2-Chloropyrimidin-4-yl)H-imidazo[1,2-a]pyridin-2-yl)acetamide

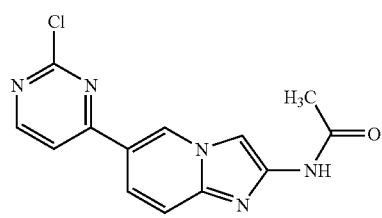

For synthesis, see Example 13, Step 5.

Example 54

N-(6-(6-Chloro-5-(N,N-dimethylsulfamoylamino)pyridin-3-yl)imidazo[1,2-b]pyridazin-2-yl)acetamide

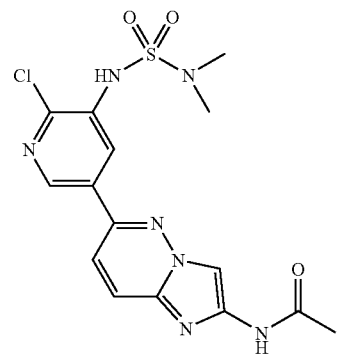

Step 1. N-(5-bromo-2-chloropyridin-3-yl) N,N-dimethylamino-1-sulfonamide

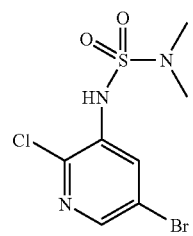

To a 100 ml round-bottom flask equipped with a stirbar, was added 5-bromo-2-chloropyridin-3-amine (0.940 g, 4.5 mmol) and pyridine (9.2 ml, 113 mmol). Then DMAP (0.17 g, 1.4 mmol) and dimethylsulfamoyl chloride (2.4 ml, 23 mmol) was added to the mixture. The flask was placed into a preheated (100° C.) bath and allowed to stir under inert atmosphere overnight. The progress of the reaction was monitored by LC/MS, which showed desired product. The mixture was removed from the heat bath and allowed to cool to ambient temperature. The mixture was poured into a 500 ml round-bottom flask and diluted with ethyl acetate (100 ml). The mixture was allowed to stir 20 minutes. This process was repeated, to optimize desired product recovery. The organic layer was poured into a round-bottom flask and concentrated in vacuo. The crude was purified by silica-gel chromatography (330 gram column), in a gradient of 0-10% EtOAc/DCM over 30 minutes. All fractions with desired material and mixed fractions were combined and concentrated in vacuo. The crude was recrystallized from ethanol. This gave N-(5-bromo-2-chloropyridin-3-yl)N,N-dimethylamino-1-sulfonamide (0.450 g, 32% yield) as a tan crystalline solid. MS (ESI pos. ion) m/z: 315 (MH+). Calc'd exact mass for $C_7H_9BrClN_3O_2S$: 314.5. $^1$H NMR (400 MHz, DMSO-$d_6$): 2.75 (s, 6H), 8.05 (d, J=2.01 Hz, 1H), 8.41 (d, J=2.01 Hz, 1H), 9.99 (s, 1H).

Step 2. N-(6-(6-chloro-5-(N,N-dimethylsulfamoylamino)pyridin-3-yl)imidazo[1,2-b]pyridazin-2-yl)acetamide

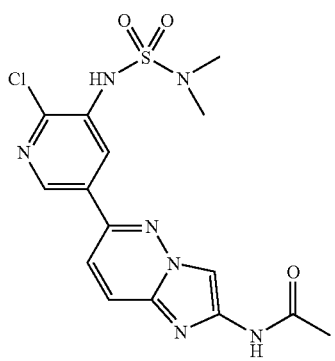

To a 100-ml round-bottomed flask was added the product from Step 1 (0.339 g, 1.078 mmol) and bis(pinacolato)diboron (0.383 g, 1.509 mmol) in DMSO (1 mL). Then potassium acetate (0.370 g, 3.8 mmol) was added to the mixture while stirring under inert atmosphere. The mixture was carefully evacuated, then backfilled with nitrogen gas. Then PdCl$_2$ (dppf)-CH$_2$Cl$_2$ adduct (0.088 g, 0.108 mmol) was added to the mixture. The flask was fitted with a reflux condenser, then placed into a pre-heated (90° C.) bath and allowed to stir for 30 minutes. The progress of the reaction was monitored by LC/MS, which showed mostly desired boronic ester (as boronic acid on LC/MS m/z=280). Then 2M sodium carbonate (0.5 ml) was added to the mixture and allowed to stir 1 minute. Then N-(6-chloroimidazo[1,2-b]pyridazin-2-yl)acetamide (0.227 g, 1.078 mmol, Example 1, Step 4) and PdCl$_2$ (dppf)-CH$_2$Cl$_2$ adduct (0.088 g, 0.108 mmol) was added to the mixture and allowed to stir under inert atmosphere at 90° C. for 1.5 hours. The progress of the reaction was monitored by LC/MS, which showed mostly desired product (m/z=410). The heat bath was removed and the reaction mixture was allowed to cool to ambient temperature. The mixture was diluted with 5:1 DCM/Methanol (30 ml) and allowed to stir 10 minutes and then filtered the mixture through a fine fritted funnel. The filtrate was collected and concentrated in vacuo. The residue was triturated with DCM and diethyl ether to give a light brown colored precipitate, which was collected by filtration. The solid was recrystallized from hot ethanol to give N-(6-(6-chloro-5-(N,N-dimethylsulfamoylamino)pyridin-3-yl)imidazo[1,2-b]pyridazin-2-yl)acetamide (0.165 g, 0.403 mmol, 37.4% yield) as a brown solid. MS (ESI pos. ion) m/z: 410 (MH+). Calc'd exact mass for $C_{15}H_{16}ClN_7O_3S$: 409.8. 1H NMR (400 MHz, DMSO-$d_6$) δ ppm 1.61 (s, 6H) 2.12 (s, 3H) 7.57 (s, 1H) 8.05 (s, 3H) 8.27 (s, 1H) 10.99 (s, 1H)

Compounds of the present invention can also be made in a process analogous to the synthesis set forth below.

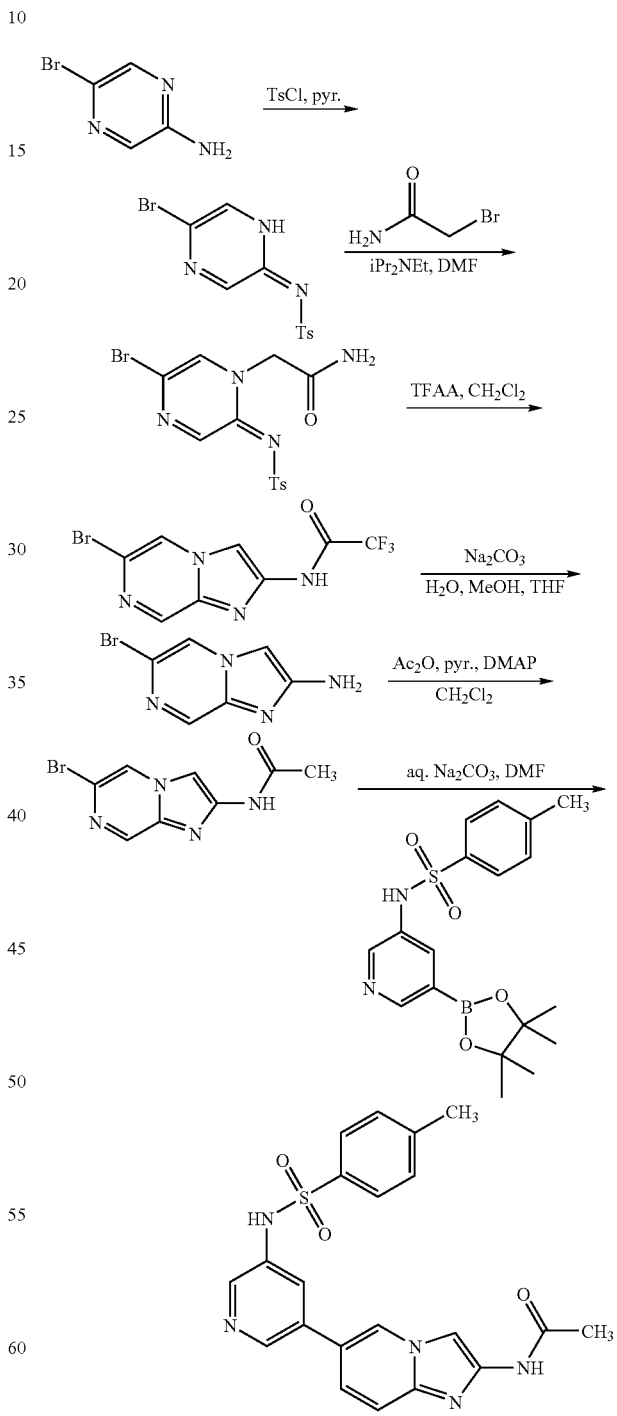

The following compounds, or pharmaceutically acceptable salts thereof, can also be made in a process analogous to the synthetic schemes and examples set forth above:

99

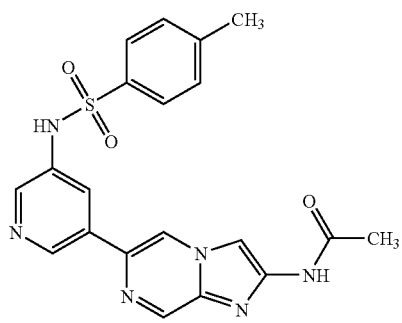

N-(6-(5-(4-methylphenylsulfonamido)pyridin-3-yl)
imidazo[1,2-a]pyrazin-2-yl)acetamide

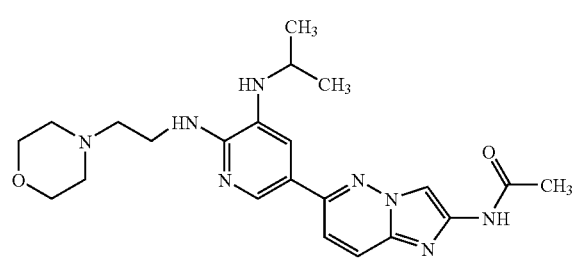

N-(6-(5-(isopropylamino)-6-(2-morpholinoethy-
lamino)pyridin-3-yl)imidazo[1,2-b]pyridazin-2-yl)
acetamide

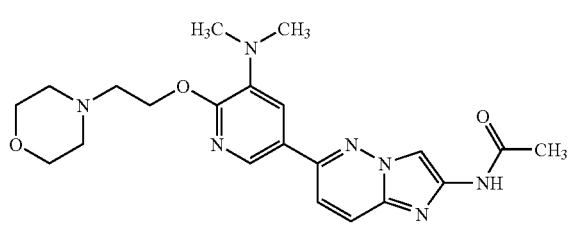

N-(6-(5-(dimethylamino)-6-(2-morpholinoethoxy)
pyridin-3-yl)imidazo[1,2-b]pyridazin-2-yl)acetamide

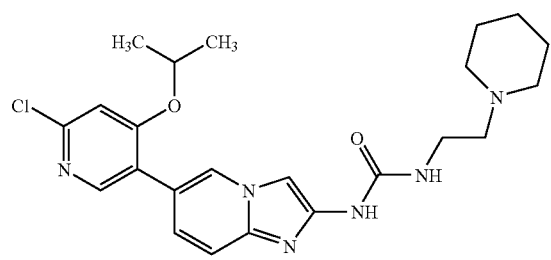

1-(6-(6-chloro-4-isopropoxypyridin-3-yl)H-imidazo
[1,2-a]pyridin-2-yl)-3-(2-(piperidin-1-yl)ethyl)urea

100

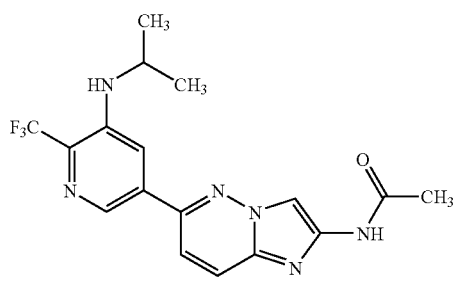

N-(6-(5-(isopropylamino)-6-(trifluoromethyl)pyri-
din-3-yl)imidazo[1,2-b]pyridazin-2-yl)acetamide

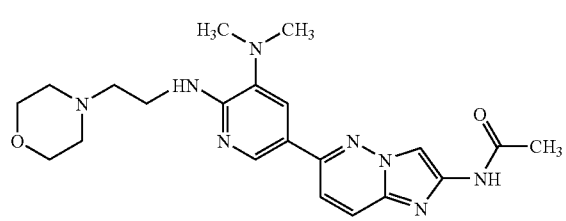

N-(6-(5-(dimethylamino)-6-(2-morpholinoethy-
lamino)pyridin-3-yl)imidazo[1,2-b]pyridazin-2-yl)
acetamide

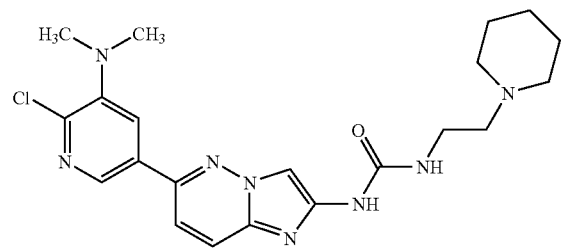

1-(6-(6-chloro-5-(dimethylamino)pyridin-3-yl)imi-
dazo[1,2-b]pyridazin-2-yl)-3-(2-(piperidin-1-yl)
ethyl)urea

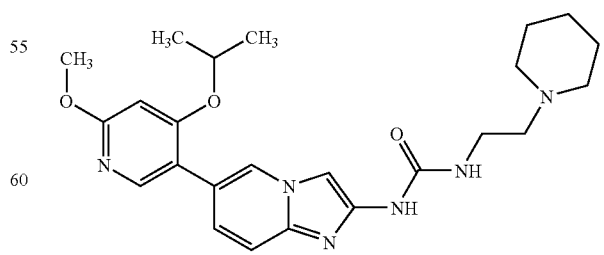

1-(6-(4-isopropoxy-6-methoxypyridin-3-yl)H-imi-
dazo[1,2-a]pyridin-2-yl)-3-(2-(piperidin-1-yl)ethyl)
urea

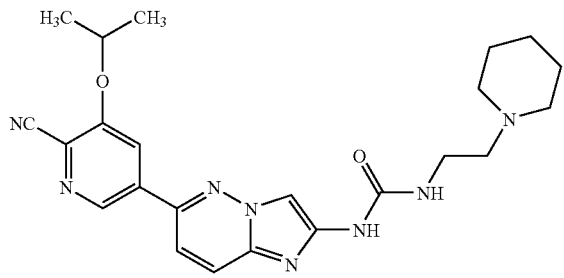

1-(6-(6-cyano-5-isopropoxypyridin-3-yl)imidazo[1,2-b]pyridazin-2-yl)-3-(2-(piperidin-1-yl)ethyl)urea

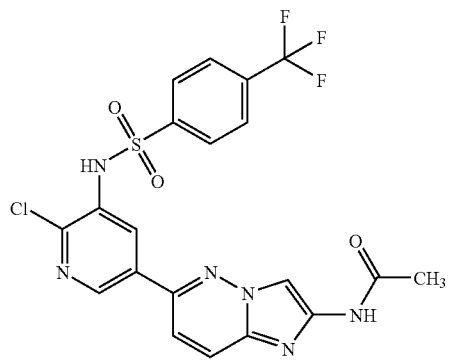

N-(6-(6-chloro-5-(4-(trifluoromethyl)phenylsulfonamido)pyridin-3-yl)imidazo[1,2-b]pyridazin-2-yl)acetamide

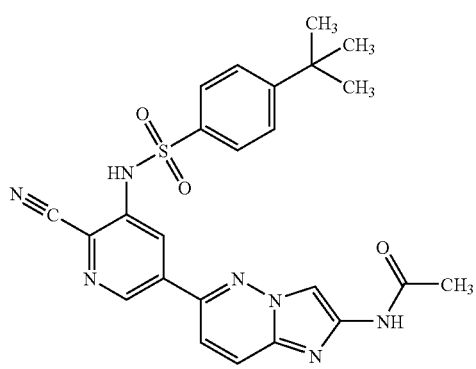

N-(6-(5-(4-tert-butylphenylsulfonamido)-6-cyanopyridin-3-yl)imidazo[1,2-b]pyridazin-2-yl)acetamide

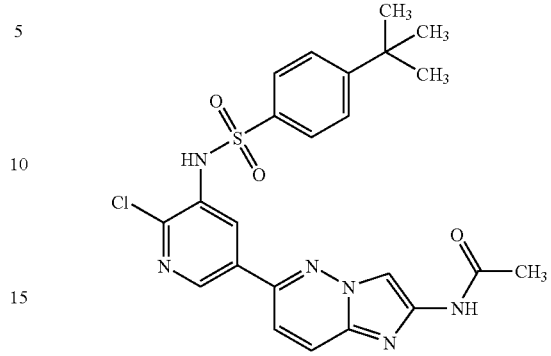

N-(6-(5-(4-tert-butylphenylsulfonamido)-6-chloropyridin-3-yl)imidazo[1,2-b]pyridazin-2-yl)acetamide; and

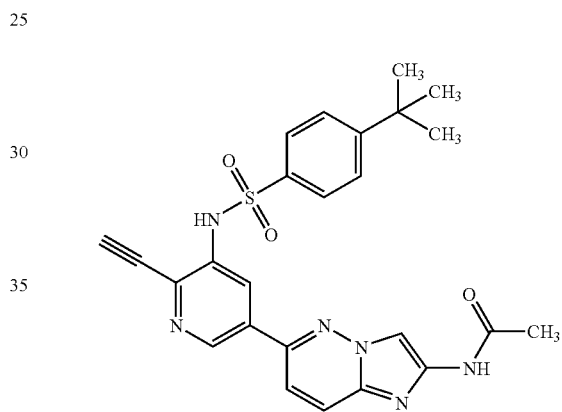

N-(6-(5-(4-tert-butylphenylsulfonamido)-6-ethynylpyridin-3-yl)imidazo[1,2-b]pyridazin-2-yl)acetamide The following assays can be used to determine the degree of activity of individual compounds as PI3 kinase inhibitors.

Recombinant Expression of PI3K Enzymes

Full length p110 subunits of PI3K α, β and δ, N-terminally labeled with polyHis tag, can be co-expressed with p85 with Baculo virus expression vectors in sf9 insect cells. P110/p85 heterodimers can be purified by sequential Ni-NTA, Q-HP, Superdex-100 chromatography. Purified α, β and δ isozymes can be stored at −20° C. in 20 mM Tris, pH 8, 0.2M NaCl, 50% glycerol, 5 mM DTT, 2 mM Na cholate. Truncated PI3Kγ, residues 114-1102, N-terminally labeled with poly-His tag, can be expressed with Baculo virus in Hi5 insect cells. The γ isozyme can be purified by sequential Ni-NTA, Superdex-200, Q-HP chromatography. The γ isozyme can be stored frozen at −80° C. in $NaH_2PO_4$, pH 8, 0.2M NaCl, 1% ethylene glycol, 2 mM β-mercaptoethanol.

|  | Alpha | Beta | Delta | Gamma |
|---|---|---|---|---|
| 50 mM Tris | pH 8 | pH 7.5 | pH 7.5 | pH 8 |
| $MgCl_2$ | 15 mM | 10 mM | 10 mM | 15 mM |
| Na cholate | 2 mM | 1 mM | 0.5 mM | 2 mM |
| DTT | 2 mM | 1 mM | 1 mM | 2 mM |
| ATP | 1 uM | 0.5 uM | 0.5 uM | 1 uM |
| PIP2 | none | 2.5 uM | 2.5 uM | none |
| time | 1 hr | 2 hr | 2 hr | 1 hr |
| [Enzyme] | 15 nM | 40 nM | 15 nM | 50 nM |

In Vitro PI3 Kinase Enzyme Assays (PI3K ATPLoss)

PI3K enzyme assays (alpha, beta, delta and gamma) can be performed in 25 μL with the above final concentrations of components in white polyproplyene plates. Phosphatidyl inositol phosphoacceptor, PtdIns(4,5)$P_2$ (e.g. P4508) can be obtained from Echelon Biosciences, Salt Lake City, Utah. The ATPase activity of the alpha and gamma isozymes may not be greatly stimulated by PtdIns(4,5)$P_2$ under these conditions, it can be omitted from the assay of these isozymes. Test compounds can be dissolved in DMSO and diluted with three-fold serial dilutions. The compound in DMSO (1 μL) may be added per test well, and the inhibition relative to reactions containing no compound, with and without enzyme can be determined. After assay incubation at RT, the reaction can be stopped and residual ATP can be determined by addition of an equal volume of a commercial ATP bioluminescence kit (Perkin Elmer EasyLite, Perkin Elmer, Waltham, Mass.) according to the manufacturer's instructions, and detected using an Analyst GT luminometer.

Activity data for the compounds tested in the PI3K enzyme assays is provided in Table 1 under the column heading PI3Kα ATPLoss Cell-Based phospho-AKT Ser473 assay (HCT116 Cell)

This assay determines the ability of a compound to inhibit the phosphorylation of Serine 472 in Akt using a MSD based sandwich immunoassay (Meso Scale Detection, Meso Scale Discovery (MSD), Gaithersburg, Md.). HCT116 human colon carcinoma cell lines can be grown in McCoy's 5A growth medium (GIBCO, Carlsbad, Calif.) containing 10% FBS (GIBCO, Carlsbad, Calif.) and X1 Penicillin-streptomycin-glutamine (GIBCO, Carlsbad, Calif.). Prior to the assay, cells can be detached from the culture flask with trypsin, and re-suspended in complete media to give a final concentration of $1.6 \times 10^5$ cells per mL. Aliquots (100 μl) of the HCT116 cell suspension can be seeded into each well of a 96 well tissue culture plate to give a final density of 16,000 cells per well. Cells can then be incubated overnight at 37° C.

The following day the cells can be treated with serially diluted test compounds and incubated for 2 hours at 37° C. The culture media on the HCT 116 cells can be replaced with 189 μL McCoys media, supplemented with 0.1% BSA (ICN Biomedicals, Inc., Costa Mesa, Calif.). Compounds can be prepared as either 10 mM or 0.5 mM stock solutions in DMSO, and serially diluted 3 fold in a 10-point dose-response curve to give final concentrations that are 200-fold greater than the desired final test concentration. Aliquots (1 μL) of serially-diluted compounds can be transferred to 96 well tissue culture plates containing the HCT 116 cells. As a minimum response control, each plate can contain wells having a final concentration of 2.5 μM of a potent PI3K inhibitor which had previously been shown to completely inhibit Akt phosphorylation at this test concentration. As a maximum response control, wells can contain 0.5% DMSO in place of compound. The plates can be mixed at 700 rpm for 2 min to ensure even distribution of the test compound and incubated for 2 hours at 37° C. Cells can then be stimulated with insulin-like growth factor 1 (Sigma, St Louis, Mo.) at final concentration of 100 ng/mL for 15 minutes at 37° C. The media can then be removed and the cells treated with 80 μL cell-lysis buffer (MSD) containing a cocktail of protease and phosphatase inhibitors for one hour at 4° C.

25 μL Cell lysate can then be transferred to pre-blocked MSD assay plates pre-coated with a capture antibody specific for Akt, and the plates can be incubated for 2 hours at room temperature. The cell lysates can then be removed and plates can then be washed four times with 200 μl per well of Tris wash buffer (500 mM Tris, PH 7.5, 1.5 M NaCl, 0.2% Tween-20). Subsequently cells can be incubated for 1 hour at room temperature with a 25 μL solution containing the detection antibody, anti-phospho Akt (Ser 473) labeled with an electrochemiluminescent compound (Meso Scale Discovery SULPHO-TAG™ label, MSD, Gaithersburg, Md.). The detection antibody can be removed and plates can then be washed four times with 200 μL per well of Tris wash buffer. An aliquot of 150 μL of diluted MSD read buffer can then be applied to each well, and the electrochemiluminescent signal can be measured using a MSD SECTOR™ plate reader (Meso Scale Discovery, Gaithersburg, Md.). This instrument measures the intensity of emitted light to determine a quantitative measure of phosphorylated Akt in each well. The dose-response data obtained with each compound can be analyzed and the $IC_{50}$ inhibition of Akt phosphorylation at Ser473 can be calculated.

Activity data for the compounds tested in the PI3K cell based Akt assay is provided in Table 1 under the column heading HCT116 Cell.

pAkt AlphaScreen (U87 Cell)

The pAkt AlphaScreen® assay (PerkinElmer, Waltham, Mass.) determines whether there is phosphorylation of Akt at Serine 473 by recruitment of a phosphospecific antibody. This assay was performed using U87 MG cells. The U87 growth media consists of MEM (Gibco, Carlsbad, Calif.) supplemented with 10% FBS (Gibco), 1× Non-Essential Amino Acids (Gibco) and 1× Penicillin/Streptomycin/Glutamine (Gibco). The cells were maintained weekly using 0.05% Trypsin (Gibco) and replated in 150 mm TC-Treated Culture Dishes (Corning, Corning, N.Y.).

The first day of the assay, the adherent cells were trypsinized, media was added to the loose cells and cells were mixed to a homogenous mixture. 0.5 ml of the homogenous mixture was counted on the Beckman Coulter® Vi-CELL™ XR (Fullerton, Calif.). 50 frames of cells were counted and the number of viable cells was determined. The cells were then diluted to 0.25 million cells per ml, and centrifuged at 200 rcf for 5 minutes. The media was removed and the cells were reconstituted in fresh media for plating. The cells were plated at 20 μl per well on the PerkinElmer® Flexprop PLUS in Low Volume 384 Well White Tissue Culture Plates (Corning) with a final cell density of 5K cells per well. The plates were incubated overnight at 37° Celsius, 5% $CO_2$.

On the second day, the compound plates were prepared, the cells were treated with compound and the pAkt reaction mix was added to the cell lysate. 384 well compound plates were prepared containing 1 μl of compound per well starting at 5 mM and diluted 1:2 across the row, resulting in a 22 well serial dilution. 39 μl of growth media was added to the compound plate in rows 1-22 using the PerkinElmer® FlexDrop PLUS resulting in a DMSO concentration of 2.5%. The cell plates and diluted compound plates were put onto the VELOCITY11™ VPREP™ 384 ST where the compound plate was mixed and 5 µl of serially diluted compound or controls was added to the cell plate. The final concentration of the compounds was 25 µM serially diluted to 11.9 pM in 0.5% DMSO. The cell plates were then incubated with compound for two hours at 37° Celsius, 5% $CO_2$. After two hours, the media in the cell plates was aspirated using the BioTek® ELx405HT plate washer (Winooski, Vt.) removing the majority of media and compound without disturbing the adherent U87 cells. The following assay reagents are components of the SureFire® Akt (Ser 473) Phosphorylation 50K Point Kit (TGR BioSciences, Adelaide, Australia) and an IgG Detection Kit (PerkinElmer, Waltham, Mass.). 5 µl of 1× Lysis Buffer was added to each well using the PerkinElmer® FlexDrop PLUS. The plates were then incubated at room temperature on a shaker for ten minutes. The AlphaScreen® reaction was prepared under low light conditions (subdued or green light) including p-Akt (Ser 473) Reaction Buffer, Dilution Buffer, Activation Buffer, Acceptor Beads and Donor Beads at a ratio of 40:20:10:1:1 respectively. The AlphaScreen® reaction was added to the cell lysate at 6 µl per well using the PerkinElmer® FlexDrop PLUS. The plates were placed in a humid environment to reduce edge effects and incubated overnight at room temperature with restricted air flow in the dark.

On the final day of the experiment, the plates were read on the PerkinElmer® EnVision™ 2103 Multilable Reader using the standard AlphaScreen® readout. The POC is calculated and the data is analyzed to report the $IC_{50}$ IP for pAkt at Serine 473.

Activity data for the compounds tested in the PI3K cell based Akt assay is provided in Table 1 under the column heading U87 Cell.

The compounds of the present invention may also inhibit mTOR. The assay below can be used to determine if a compound inhibits mTOR. Thus, one aspect of the present invention concerns compounds that inhibit PI3K and mTOR. The present invention also contemplates the use of such compounds for the treatment of the diseases and conditions, such as cancer, disclosed herein.

In Vitro mTOR Assay

The Invitrogen (Carlsbad, Calif.) mammalian target of rapamycin (mTOR) Lanthascreen assay can be used to quantitate mTOR kinase activity in an in vitro setting. Active mTOR phosphorylates eukaryotic translation initiation factor 4E binding protein 1 (4E-BP1) on residue threonine 46. This phosphorylation event can be detected with a phospho-specific terbium (Tb) labeled Ab, in turn bringing the Tb label in close proximity to the GFP tagged 4E-BP1 and allowing for time-resolved fluorescence resonance energy transfer (TR-FRET), which correlates 4E-BP1 phosphorylation levels with mTOR kinase activity.

Enzyme reaction buffer can be prepared in deionized water containing 50 mM HEPES (pH 7.5), 0.01% Polysorbate 20, 1 mM EGTA, and 10 mM $MnCl_2$.

Dilutions of the compound to be tested can be prepared in 96-well polypropylene plates (Fisher Scientific, Waltham, Mass.). One row represents a 10-point dose of compound diluted 1:3 in enzyme reaction buffer and 20% dimethyl sulfoxide (DMSO). The top concentration for all compounds is 36 µM. Wells 6 and 12 can serve as the no compound (DMSO only) and high compound controls.

An mTOR substrate solution can prepared in enzyme reaction buffer containing 1600 nM green fluorescent protein tagged eukaryotic translation initiation factor 4E binding protein 1 (GFP-4E-BP1) (Invitrogen, Carlsbad, Calif.) and 28 uM adenosine triphosphate (ATP) (Calbiochem, Gibbstown, N.J.).

mTOR enzyme (Invitrogen, Carlsbad, Calif.) can be diluted in enzyme reaction buffer to a working concentration of 100 ng/mL.

The enzyme assay can be run in 384 well low volume assay plates (Corning, Corning, N.Y.). 2.5 uL of substrate solution containing GFP-4E-BP1 and ATP can be added to appropriate wells in the assay plate followed by 2.5 µL of compound dilutions. 5 µL of appropriately diluted mTOR enzyme can be added and the reaction allowed to proceed for 1 hour at room temperature. Final reagent concentrations in the enzyme assay are 50 ng/mL mTOR, 400 nM GFP-4E-BP1, and 7 µM ATP.

The enzyme assay can be terminated upon the addition of 10 µL of 20 mM EDTA and 4 nM Tb-labeled anti-phospho-4E-BP1 [T46] antibody (Invitrogen, Carlsbad, Calif.). The assay plate can then be incubated at room temperature for 1 hour and results read on a Tecan Safire II plate reader (Tecan, Mannedorf, Switzerland).

TABLE 1

| Example No. | PI3Kα ATPloss $IC_{50}$ (µM) | HCT116 Cell $IC_{50}$ (µM) | U87 Cell $IC_{50}$ (µM) |
| --- | --- | --- | --- |
| 1 | 0.055 | 0.214 | |
| 2 | 0.098 | 0.462 | |
| 3 | 0.782 | | |
| 4 | 0.077 | 1.142 | |
| 5 | 0.982 | | |
| 6 | 0.096 | | |
| 7 | 0.062 | 0.456 | |
| 8 | 0.060 | 1.203 | |
| 9 | 0.395 | | |
| 10 | 0.104 | 0.869 | |
| 11 | 0.006 | 0.213 | |
| 12 | 0.007 | 0.031 | 0.014 |
| 13 | 0.146 | 0.847 | |
| 14 | 0.214 | | |
| 15 | 0.010 | 0.975 | |
| 16 | 0.019 | 14.388 | |
| 17 | 0.037 | 29.344 | |
| 18 | 0.211 | | |
| 19 | 0.0057 | 0.218 | 0.133 |
| 20 | 0.014 | | 0.115 |
| 21 | 0.033 | | 2.185 |
| 22 | 0.015 | | 3.200 |
| 23 | 0.102 | | 0.055 |
| 24 | 0.093 | | 25 |
| 25 | 1.172 | | 25 |
| 26 | 0.009 | | 6.528 |
| 27 | 0.154 | | 3.495 |
| 28 | 0.009 | 0.046 | 0.118 |
| 29 | 0.064 | | |
| 30 | 0.012 | 1.095 | |
| 31 | 0.008 | 0.868 | |
| 32 | 0.049 | 2.722 | |
| 33 | 0.007 | 0.024 | 0.015 |
| 34 | 0.007 | 0.003 | 0.007 |
| 35 | 0.006 | 0.049 | 0.034 |
| 36 | 0.083 | 2.430 | 0.415 |
| 37 | 0.007 | 0.244 | |
| 38 | 0.006 | 0.124 | 0.031 |
| 39 | 0.008 | 0.105 | 0.028 |
| 40 | 0.005 | 0.055 | 0.021 |
| 41 | 0.006 | 0.075 | 0.047 |
| 42 | 0.006 | | 0.005 |
| 43 | 0.044 | | 0.242 |
| 44 | | | 7.475 |
| 45 | | | 0.027 |
| 46 | | | 5.792 |
| 47 | | | 0.014 |
| 48 | | | 0.018 |

TABLE 1-continued

| Example No. | PI3Kα ATPloss IC$_{50}$ (µM) | HCT116 Cell IC$_{50}$ (µM) | U87 Cell IC$_{50}$ (µM) |
|---|---|---|---|
| 49 | | | 3.900 |
| 50 | | | 0.118 |
| 51 | | | 0.439 |
| 52 | 0.691 | | 0.523 |
| 53 | 1.859 | | |

Blank = not tested

What is claimed is:

1. A compound of Formula I

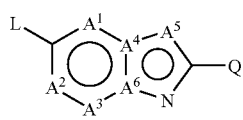

or a pharmaceutically acceptable salt thereof, wherein
Q is —NR$^1$R$^1$, or —NR$^1$C(=O)R$^1$;
each R$^1$ is independently hydrogen, C$_1$-C$_8$ alkyl, C$_3$-C$_8$cycloalkyl, substituted C$_3$-C$_8$cycloalkyl, heterocycloalkyl, substituted heterocycloalkyl, aryl, substituted aryl, heteroaryl or substituted heteroaryl;
L is

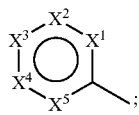

X$^1$, X$^3$, X$^4$ and X$^5$ are CR or N;
X$^2$ is CR$^2$;
R$^2$ is —NR$^1$[S(=O)$_2$R$^1$];
A$^1$ and A$^4$ are N;
A$^2$, A$^3$ and A$^5$ are CR;
A$^6$ is C; and
each R is independently halogen, hydrogen, C$_1$-C$_8$ alkyl, C$_3$-C$_8$cycloalkyl, substituted C$_3$-C$_8$cycloalkyl, heterocycloalkyl, substituted heterocycloalkyl, aryl, substituted aryl, heteroaryl or substituted heteroaryl.

2. A compound in accordance with claim 1 wherein Q is NH$_2$, or —NHC(=O)CH$_3$.

3. A compound in accordance with claim 1 wherein A$^2$ and A$^3$ are CH and A$^5$ is CR.

4. A compound in accordance with claim 1 wherein A$^2$ and A$^3$ are CH; A$^5$ is CR; and R is heteroaryl or substituted heteroaryl.

5. A compound in accordance with claim 1 wherein L is

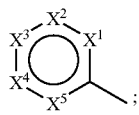

X$^1$, X$^3$ and X$^5$ are CR;
and X$^4$ is N.

6. A compound in accordance with claim 1 wherein L is

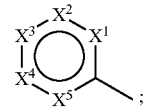

X$^1$, X$^3$ and X$^5$ are CR;
X$^4$ is N;
X$^2$ is CR$^2$;
R$^2$ is —NH[S(=O)$_2$R$^1$]; and
R$^1$ is aryl or substituted aryl.

7. A compound in accordance with claim 1 wherein L is

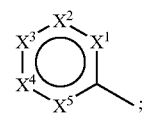

X$^1$, X$^3$ and X$^5$ are CR;
X$^4$ is N;
X$^2$ is CR$^2$;
R$^2$ is —NH[S(=O)$_2$R$^1$]; and
R$^1$ is difluoromethoxyphenyl.

8. The compound:
N-(6-(6-Chloro-5-(3-(difluoromethoxy)phenylsulfonamido)pyridin-3-yl)-3-(pyridin-4-yl)imidazo[1,2-b]pyridazin-2-acetamide;
N-(5-(2-amino-3-(pyridin-4-yl)imidazo[1,2-b]pyridazin-6-yl)-2-chloropyridin-3-yl) -3-(difluoromethoxy)benzenesulfonamide;
N-(6-(6-chloro-5-(3-(difluoromethoxy)phenylsulfonamido)pyridin-3-yl)-3-(2-methylpyridin-4-yl)imidazo[1,2-b]pyridazin-2-yl)acetamide;
N-(5-(2-amino-3-(2-methylpyridin-4-yl)imidazo[1,2-b]pyridazin-6-yl)-2-chloropyridin-3-yl)-3-(difluoromethoxy)benzenesulfonamide;
N-(6-(6-chloro-5-(3-(difluoromethoxy)phenylsulfonamido)pyridin-3-yl)-3-(pyridin-3-yl)imidazo[1,2-b]pyridazin-2-yl)acetamide;
N-(5-(2-amino-3-(pyridin-3-yl)imidazo[1,2-b]pyridazin-6-yl)-2-chloropyridin-3-yl)-3-(difluoromethoxy)benzenesulfonamide; or
N-(5-(2-amino-3-(1,2,3,6-tetrahydropyridin-4-yl)imidazo[1,2-b]pyridazin-6-yl)-2-chloropyridin-3-yl)-3-(difluoromethoxy)benzenesulfonamide, or a pharmaceutically acceptable salt thereof.

9. A pharmaceutical composition comprising:
A) a compound of Formula I

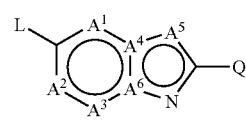

or a pharmaceutically acceptable salt thereof, wherein
Q is —NR$^1$R$^1$, or —NR$^1$C(=O)R$^1$;
each R$^1$ is independently hydrogen, C$_1$-C$_8$ alkyl, C$_3$-C$_8$cycloalkyl, substituted C$_3$-C$_8$cycloalkyl, heterocycloalkyl, substituted heterocycloalkyl, aryl, substituted aryl, heteroaryl or substituted heteroaryl;

L is

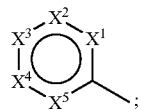;

$X^1$, $X^3$, $X^4$ and $X^5$ are CR or N;
$X^2$ is $CR^2$;
$R^2$ is —$NR^1[S(=O)_2R^1]$;
$A^1$ and $A^4$ are N;
$A^2$, $A^3$ and $A^5$ are CR;
$A^6$ is C; and
each R is independently halogen, hydrogen, $C_1$-$C_8$ alkyl, $C_3$-$C_8$cycloalkyl, substituted $C_3$-$C_8$cycloalkyl, heterocycloalkyl, substituted heterocycloalkyl, aryl, substituted aryl, heteroaryl or substituted heteroaryl; and B) a pharmaceutically acceptable excipient.

* * * * *